United States Patent
Seike et al.

(10) Patent No.: US 10,626,404 B2
(45) Date of Patent: Apr. 21, 2020

(54) MUTANT XYLOSE-METABOLIZING ENZYME AND USE THEREOF

(71) Applicant: National Institute of Advanced Industrial Science and Technology, Tokyo (JP)

(72) Inventors: Taisuke Seike, Ibaraki (JP); Kazuhiro Fujimori, Ibaraki (JP); Yosuke Kobayashi, Ibaraki (JP); Takehiko Sahara, Ibaraki (JP); Satoru Ohgiya, Hokkaido (JP); Yoichi Kamagata, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 16/087,201

(22) PCT Filed: Mar. 24, 2017

(86) PCT No.: PCT/JP2017/012104
§ 371 (c)(1),
(2) Date: Sep. 21, 2018

(87) PCT Pub. No.: WO2017/164388
PCT Pub. Date: Sep. 28, 2017

(65) Prior Publication Data
US 2019/0071684 A1 Mar. 7, 2019

(30) Foreign Application Priority Data

Mar. 25, 2016 (JP) .................. 2016-062838

(51) Int. Cl.
| | | |
|---|---|---|
| C12N 15/81 | (2006.01) | |
| C12N 15/09 | (2006.01) | |
| C12N 9/92 | (2006.01) | |
| C12P 7/06 | (2006.01) | |

(52) U.S. Cl.
CPC ............. *C12N 15/815* (2013.01); *C12N 9/92* (2013.01); *C12N 15/09* (2013.01); *C12P 7/06* (2013.01); *C12Y 503/01005* (2013.01)

(58) Field of Classification Search
None
See application file for complete search history.

(56) References Cited

U.S. PATENT DOCUMENTS

2011/0269180 A1   11/2011   Brat et al.

FOREIGN PATENT DOCUMENTS

| WO | 2010/000464 A1 | 1/2010 |
| WO | 2011/150313 A1 | 12/2011 |
| WO | 2014/156194 A1 | 10/2014 |

OTHER PUBLICATIONS

Aeling et al., "Co-fermentation of xylose and cellobiose by an engineered *Saccharomyces cerevisiae*," J Ind Microbiol Biotechnol, 2012, vol. 39, pp. 1597-1604.

Brat et al., "Functional Expression of a Bacterial Xylose Isomerase in *Saccharomyces cerevisiae*," Applied and Environmental Microbiology, Apr. 2009, vol. 75, No. 8, pp. 2304-2311.

De Figueiredo Vilela et al., "Functional expression of Burkholderia cenocepacia xylose isomerase in yeast increases ethanol production from a glucose-xylose blend," Bioresource Technology, 2013, vol. 128, pp. 792-796.

Demeke et al., "Development of a D-xylose fermenting and inhibitor tolerant industrial *Saccharomyces cerevisiae* strain with high performance in lignocellulose hydrolysates using metabolic and evolutionary engineering," Biotechnology for Biofuels, 2013, 6:89, 24 pages.

Harcus et al., "Comparative Xylose Metabolism among the Ascomycetes *C. albicans, S. stipitis* and *S. cerevisiae*," PLoS ONE, Nov. 2013, vol. 8, Issue 11, e80733. doi. 10.1371/journal.pone.0080733.

Hector et al., "Growth and fermentation of D-xylose by *Saccharomyces cerevisiae* expressing a novel D-xylose isomerase originating from the bacterium Prevotella ruminicola TC2-24," Biotechnology for Biofuels, 2013, 6:84, 12 pages.

Kuyper et al., High-level functional expression of a fungal xylose isomerase: the key to efficient ethanolic fermentation of xylose by *Saccharomyces cerevisiae*? FEMS Yeast Research, 2003, vol. 4, pp. 69-78.

Lee et al., "Directed Evolution of Xylose Isomerase for Improved Xylose Catabolism and Fermentation in the Yeast *Saccharomyces cerevisiae*," Applied and Environmental Microbiology, Aug. 2012, vol. 78, No. 16, pp. 5708-5716.

(Continued)

*Primary Examiner* — Suzanne M Noakes
(74) *Attorney, Agent, or Firm* — Kilpatrick Townsend & Stockton LLP

(57) ABSTRACT

The present invention provides information on a mutant xylose isomerase gene and a mutant protein with which it is possible to impart high xylose metabolic capacity to budding yeast. Also provided is a yeast strain having the mutant xylose isomerase gene. Additionally provided is an efficient method for producing a useful substance using the yeast strain. The present invention provides mutant *Clostridium-phytofermentans*-derived xylose isomerase (CpXI) having high xylose metabolic activity, the CpXI comprising an amino acid sequence corresponding to an amino acid sequence in which the number 63 threonine of SEQ ID NO: 11 of CpXI is substituted by isoleucine, leucine, glycine, or histidine and/or the number 162 valine is substituted by alanine. Also provided are: a transformed yeast having high ethanol productivity, the transformed yeast being obtained by transformation using a mutant CpXI gene that comprises a codon mutation corresponding to a codon mutation in which the number 63 threonine of SEQ ID NO: 11 in a CpXI gene optimized for the preferred codon of budding yeast is substituted by isoleucine, leucine, glycine, or histidine and/or the number 162 valine is substituted by alanine; and a method for producing ethanol using the transformed yeast.

10 Claims, 10 Drawing Sheets
Specification includes a Sequence Listing.

(56) References Cited

OTHER PUBLICATIONS

Tanino et al., "Construction of a xylose-metabolizing yeast by genome integration of xylose isomerase gene and investigation of the effect of xylitol on fermentation," Appl Microbiol Biotechnol. 2010, 88: pp. 1215-1221.
Waltman et al., "Engineering acidic Streptomyces rubiginosus D-xylose isomerase by rational enzyme design," Protein Engineering, Design & Selection, 2014, vol. 27, No. 2, pp. 59-64.
PCT/JP2017/012104, International Search Report, dated Jun. 20, 2017, 2 pages.

MUTANT XYLOSE-METABOLIZING ENZYME AND USE THEREOF

CROSS-REFERENCE TO RELATED APPLICATIONS

The present application is a National Phase entry of International Application No. PCT/JP2017/012104, filed Mar. 24, 2017, which claims priority to Japanese Patent Application No. 2016-062838, filed Mar. 25, 2016, the disclosures of which are hereby incorporated by reference in their entireties for all purposes.

REFERENCE TO SUBMISSION OF A SEQUENCE LISTING AS A TEXT FILE

The Sequence Listing written in file SequenceLisitng_093803-005400US-1105996.txt created on Sep. 20, 2018, 57,214 bytes, machine format IBM-PC, MS-Windows operating system, is hereby incorporated by reference in its entirety for all purposes.

FIELD

The present invention relates to a technique for producing ethanol by a fermentation method using yeast, and more specifically it relates to a mutant xylose isomerase with enhanced xylose metabolic capacity, and to a method of producing ethanol from a biomass saccharified solution by yeast into which the enzyme gene has been transferred.

BACKGROUND

The budding yeast *Saccharomyces cerevisiae* is a microorganism with high fermentation ability and high ethanol resistance, and it has long been used to generate ethanol mainly for production of alcoholic beverages, while also being utilized in recent years for fuel ethanol production. Moreover, ethanol is also known to be a renewable form of energy, as an alternative fuel to gasoline, and it is produced by fermentation methods using plant-derived biomass.

First generation bioethanol is fuel ethanol produced by fermentation using budding yeast or the like, with the starting material being glucose from sugarcane and the like, or glucose obtained by enzymolysis of starch from corn and the like. However, competition of these starting materials with foods and livestock feeds is considered to be a problem.

Second generation bioethanol, on the other hand, is ethanol produced from cellulosic biomass, which does not compete with foods or livestock feeds. Various problems are known to be associated with ethanol production from cellulosic biomass, depending on the combination of the type of starting material, pretreatment method, saccharification process and fermentation process, and solutions to these problems are desired.

Furthermore, while various resources may be considered for cellulosic biomass, ligneous materials are considered especially promising for use because they contain the largest amounts of cellulose, which serves as the starting material for glucose. Ligneous materials also comprise hemicellulose and lignin as main components in addition to cellulose, and the use of hemicellulose, as their second most abundant component after cellulose, has also been an important issue in ethanol production from cellulosic biomass. Hemicellulose is converted to xylose by decomposition with saccharifying enzymes, but since the genes for assimilation of xylose are essentially non-functioning in budding yeast, the issue of extremely low ethanol production efficiency from xylose has been a problem. Therefore, much research is being conducted into introducing xylose metabolizing enzymes of xylose-assimilating organisms into budding yeast, or imparting budding yeast with xylose-assimilating properties by forced expression of endogenous genes associated with xylose metabolism. The enzymes associated with xylose metabolism include xylose reductase, xylitol dehydrogenase, xylulose kinase, xylose isomerase and enzymes involved in the pentose phosphate pathway.

Two different pathways exist for conversion from xylose to xylulose, one being a reductive pathway which is catalyzed by an NADPH-dependent xylose reductase (XR) and a $NAD^+$-dependent xylitol dehydrogenase (XDH), and since the two enzymes have different coenzymes, their imbalance can result in accumulation of xylitol as by-product (NPL 1). In production of ethanol from xylose on an industrial scale, the problem of xylitol accumulation has been linked to reduced ethanol production efficiency, and it is therefore important to find a solution.

The other pathway is catalyzed by xylose isomerase (XI), and is advantageous in that the problem of accumulation of xylitol as a by-product does not occur. A known problem with yeast cells that express xylose isomerase genes is the slow ethanol production rate from xylose. In order to solve these problems, xylose isomerase genes have been cloned from numerous bacteria and fungi, and attempts have been made to express them in yeast cells. It has been so far demonstrated that xylose isomerase genes from *Piromyces* sp. E2 (NPL 2), *Orpinomyces* sp. ukk1 (NPL 3), *Clostridium phytofermentans* ISDg (NPL 4), *Ruminococcus flavefaciens* 17 (NPL 5), *Prevotella ruminicola* TC2-24 (NPL 6), *Burkholderia cenocepacia* J2315 (NPL 7), *Clostridium cellulolyticum* H10 (NPL 8) and *Streptomyces rubiginosus* (NPL 9) function in yeast cells and can impart xylose metabolic capacity to host budding yeast, albeit with poor efficiency.

In recent years, high activation of xylose isomerase from *Piromyces* sp. E2 using molecular evolutionary engineering methods has been reported (NPL 10). In this publication, it is shown that xylose isomerase from mutant *Piromyces* sp. E2 having mutations introduced at 6 sites (E15D, E114G, E129D, T142S, A177T and V433I) improves ethanol production by increasing the growth rate of budding yeast under aerobic conditions with xylose as the carbon source, as well as their consumption rate of xylose. It is indicated that the xylose isomerase from mutant *Piromyces* sp. E2 had a $V_{max}$ value that was 77% larger than the wild type, while the Km value was approximately twice as high. Among the 6 mutations, E15D and T142S were shown to be the important amino acid mutations for high activation.

It has also been reported that for xylose isomerase from *Ruminococcus flavefaciens* 17 as well, 5% improvement in activity was achieved by amino acid substitution (G179A) near the xylose bonding site, and 26.8% improvement in activity was achieved by replacing the N-terminal 10 amino acid sequence with the N-terminal 12 amino acid sequence of xylose isomerase from *Piromyces* sp. E2 (NPL 5).

In regard to xylose isomerase from *Streptomyces rubiginosus*, it has been reported that several mutant xylose isomerase genes were obtained which had acquired high affinity for xylose, under reaction conditions of pH 6 or lower (NPL 9).

Thus, while much research is being conducted on xylose isomerases for highly efficient bioethanol production from xylose in yeast, the xylose metabolic capacities of yeast in which the xylose isomerase genes have been transferred have each been evaluated under different conditions, and no published reports have dealt with determining which are the biologically-derived xylose isomerase genes for xylose isomerases capable of imparting the most efficient ability to produce bioethanol from xylose, or with comparative examination of different xylose isomerases in the same host strains and under the same expression conditions and culturing conditions. Moreover, while the fermentation conditions that allow the most efficient production of ethanol in budding yeast are anaerobic or microaerobic conditions, most of the reports to date deal with evaluating the functions of xylose isomerases with culturing under aerobic conditions, and not with comparative evaluation under fermentation conditions that allow highly efficient production of ethanol. In addition, even for mutant xylose isomerases that have been highly functionalized by introduction of mutations, it is still unknown whether they contribute to highly efficient bioethanol production under anaerobic or microaerobic conditions.

CITATION LIST

Patent Literature

[PTL 1] Japanese Unexamined Patent Publication No. 2015-33342
[PTL 2] Japanese Patent Publication No. 4332630

Non Patent Literature

[NPL 1] Matsushika A, et al., Applied and Environmental Microbiology, 2009, 75, p. 3818-3822.
[NPL 2] Kuyper M, et al., FEMS Yeast Research, 2003, 4, p. 69-78.
[NPL 3] Tanino T, et al., Applied Microbiology and Biotechnology, 2010, 88, p. 1215-1221.
[NPL 4] Demeke M M, et al., Biotechnology for Biofuels, 2013, 6, p. 89.
[NPL 5] Aeling K A, et al., Journal of Industrial Microbiology and Biotechnology, 2012, 39, p. 1597-1604.
[NPL 6] Hector R E, et al., Biotechnology for Biofuels, 2013, 6, p. 84.
[NPL 7] de Figueiredo Vilela L, et al., Bioresource Technology, 2013, 128, p. 792-796.
[NPL 8] Harcus D, et al., PloS One, 2013, 8, e80733.
[NPL 9] Waltman M J, et al., Protein Engineering, Design and Selection, 2014, 27, p. 59-64.
[NPL 10] Lee S M, et al., Applied and Environmental Microbiology, 2012, 78, p. 5708-5716.
[NPL 11] Abstracts from the 2016 Convention of the Japan Society for Bioscience, Biotechnology and Agrochemistry, (held Mar. 27-30, 2016), presentation numbers: 2A022, 2A023
[NPL 12] Akashi H., Genetics, 2003, 164, p. 1291-1303.
[NPL 13] Kuriyama H, et al., Journal of Fermentation Technology, 1985, 63, p. 59-165.

SUMMARY

Technical Problem

According to the invention there is provided information for optimal xylose isomerase genes, by using 8 types of xylose isomerase genes from different sources, carrying out codon optimization and cloning into the same expression vector of each xylose isomerase gene under the same conditions, creating practical ethanol-producing yeast strains in which plasmids are introduced that express the respective xylose isomerase genes, and evaluating their xylose assimilation under the same culturing conditions. There are also provided mutant xylose isomerase genes and mutant proteins able to impart high xylose metabolic capacity to budding yeast, by conducting artificial mutation transfer into optimal xylose isomerase genes and evaluating the xylose assimilation of yeast strains having the mutant xylose isomerase genes. There are also provided yeast strains having the mutant xylose isomerase genes. There is still further provided a method for efficiently producing useful substances utilizing the yeast strains.

Solution to Problem

As explained under "BACKGROUND", in order to efficiently produce ethanol from xylose in yeast it is necessary to introduce an exogenous xylose metabolizing enzyme gene with excellent xylose metabolic capacity into yeast cells, in a functional form. In the past, many xylose isomerase genes have been isolated and their expression in yeast has been attempted, but few reports exist of xylose isomerase genes that have been successfully expressed in yeast cells in a functional form. Moreover, evaluation of the xylose metabolic capacities of different xylose isomerases in yeast cells has been conducted under different fermentation conditions, and it has not been determined which xylose isomerase genes are suitably expressed in yeast cells, or whether or not the excellent xylose metabolic capacity can be imparted to the host yeast cells. In addition, much still remains unknown regarding whether these xylose isomerase genes effectively function during fermentation under anaerobic conditions or microaerobic conditions that allow highly efficient production of ethanol, and therefore in order to efficiently improve production of ethanol from xylose it is important to screen for optimal xylose isomerase genes.

The present inventors decided to screen for xylose isomerase genes capable of imparting the most excellent xylose metabolic capacity from among 8 types of xylose isomerase genes that had already been successfully expressed in functional form in budding yeast, and as the screening method, used a modified form of a screening method combining fermentation tests using high-concentration xylose medium wider aerobic conditions and synthetic saccharified solution (YPDX) medium under microaerobic conditions, which had been previously used by the present inventors to obtain yeast variants with improved xylose metabolic capacity (PTL 1).

Specifically, for the 8 types of xylose isomerase genes, different xylose isomerase gene-expressing plasmids were constructed using the same promoter and terminator, with the codons optimized in order to minimize the effects of translation efficiency, and these were introduced into the same practical ethanol-producing yeast strain to construct yeast strains expressing each of the xylose isomerase genes. The obtained yeast strains were used for evaluation of growth in medium using xylose as the carbon source, to examine the xylose assimilation of each yeast strain. Ethanol productivity was also evaluated by a batch fermentation test under microaerobic conditions using a synthetic saccharified solution ($YPD_{85}X_{35}$). Based on these evaluations, a *Clostridium phytofermentans* gene (CpXI gene) was screened out as the xylose isomerase gene capable of imparting the most excellent xylose metabolic capacity. Next, with the aim of improving the xylose metabolic capacity, a mutant xylose isomerase gene library was prepared having artificial mutations introduced by a molecular evolutionary engineering method into the screened xylose isomerase gene (CpXI gene), growth was carried out wider aerobic conditions in medium using xylose as the carbon source, and evaluation was conducted by a batch fermentation test under microaerobic conditions using a synthetic saccharified solution (YPD$_{85}$X$_{35}$) (NPL 11).

As a result, there were isolated several different mutant xylose isomerase genes having mutations introduced at different locations on the amino acid sequence level. In addition, a double mutant xylose isomerase gene was constructed which had combined mutations at two locations among the mutations in these mutant xylose isomerase genes, and evaluation was conducted in a batch fermentation test under microaerobic conditions using the synthetic saccharified solution (YPD$_{85}$X$_{35}$). As a result, it was found that two different mutant xylose isomerase genes, and particularly the double mutant xylose isomerase gene, can impart to host yeast strains more excellent xylose metabolic capacity than previously reported xylose isomerases, and the invention was completed upon this finding.

Specifically, the present invention encompasses the following inventions.

[1] A mutant xylose isomerase (mutant CpXI) comprising an amino acid sequence wherein at least one amino acid corresponding to the threonine at position 63 and the valine at position 162 of SEQ ID NO: 11 is substituted to another amino acid in the amino acid sequence of *Clostridium phytofermentans* xylose isomerase (CpXI), the mutant CpXI having higher xylose metabolic activity than the wild type xylose isomerase (CpXI).

[2] The mutant CpXI according to [1] above, wherein the substitution of the threonine at position 63 of SEQ ID NO: 11 to another amino acid is a substitution to isoleucine, leucine, glycine or histidine, and the substitution of the valine at position 162 to another amino acid is a substitution to alanine.

[3] The mutant CpXI according to [2] above, wherein the threonine at position 63 is substituted to isoleucine, leucine, glycine or histidine, and/or the valine at position 162 is substituted to alanine in the amino acid sequence of the xylose isomerase listed as SEQ ID NO: 11.

Particularly preferred is mutant CpXI comprising an amino acid sequence wherein the threonine at position 63 of SEQ ID NO: 11 is substituted to isoleucine and the valine at position 162 is substituted to alanine.

[4] A mutant xylose isomerase gene (mutant CpXI gene) comprising a nucleotide sequence wherein at least one codon of the codons corresponding to threonine at position 63 and valine at position 162 of SEQ ID NO: 11 of the encoded amino acid sequence is substituted to a codon corresponding to another amino acid in the nucleotide sequence of a *Clostridium phytofermentans* xylose isomerase (CpXI) gene, the mutant CpXI gene imparting to *Saccharomyces cerevisiae* hosts higher xylose metabolic capacity and higher ethanol productivity than the wild type CpXI gene.

[5] The mutant CpXI gene according to [4] above, comprising a nucleotide sequence having a codon mutation corresponding to a mutation in which the threonine at position 63 of the coded amino acid sequence is substituted to isoleucine, leucine, glycine or histidine and/or the valine at position 162 is substituted to alanine in the nucleotide sequence of the xylose isomerase gene (CpXI gene) listed as SEQ ID NO: 12.

Particularly preferred is a mutant CpXI gene comprising in SEQ ID NO: 12 a nucleotide sequence having a codon mutation corresponding to a mutation in which the threonine at position 63 of the coded amino acid sequence is substituted to isoleucine and the valine at position 162 is substituted to alanine.

[6] A transformed yeast that has been transformed by the mutant CpXI gene according to [4] or [5] above, the yeast having higher xylose metabolic capacity than the parent yeast.

[7] The transformed yeast according to [6] above, wherein the yeast is a yeast selected from the group consisting of *Saccharomyces, Kluyveromyces, Candida, Pichia, Schizosaccharomyces* and *Hansenula*.

[8] The transformed yeast according to [6] above, wherein the yeast is *Saccharomyces* yeast.

[9] A method of producing ethanol using a transformed yeast according to any one of [6] to [8] above, in the presence of xylose.

Advantageous Effects of Invention

According to the invention there are provided microorganisms with excellent xylose metabolic capacity. In addition, by utilizing a mutant gene or mutant protein coding for the mutant xylose isomerase discovered by the present invention, it is possible to create a microorganism having excellent xylose metabolic capacity, using gene recombinant technology or the like. In addition, by using a microorganism of the invention or a microorganism having a mutant gene discovered by the present invention, it is possible to efficiently produce a useful substance such as ethanol, utilizing xylose-containing medium.

DESCRIPTION OF EMBODIMENTS

Figure 1:
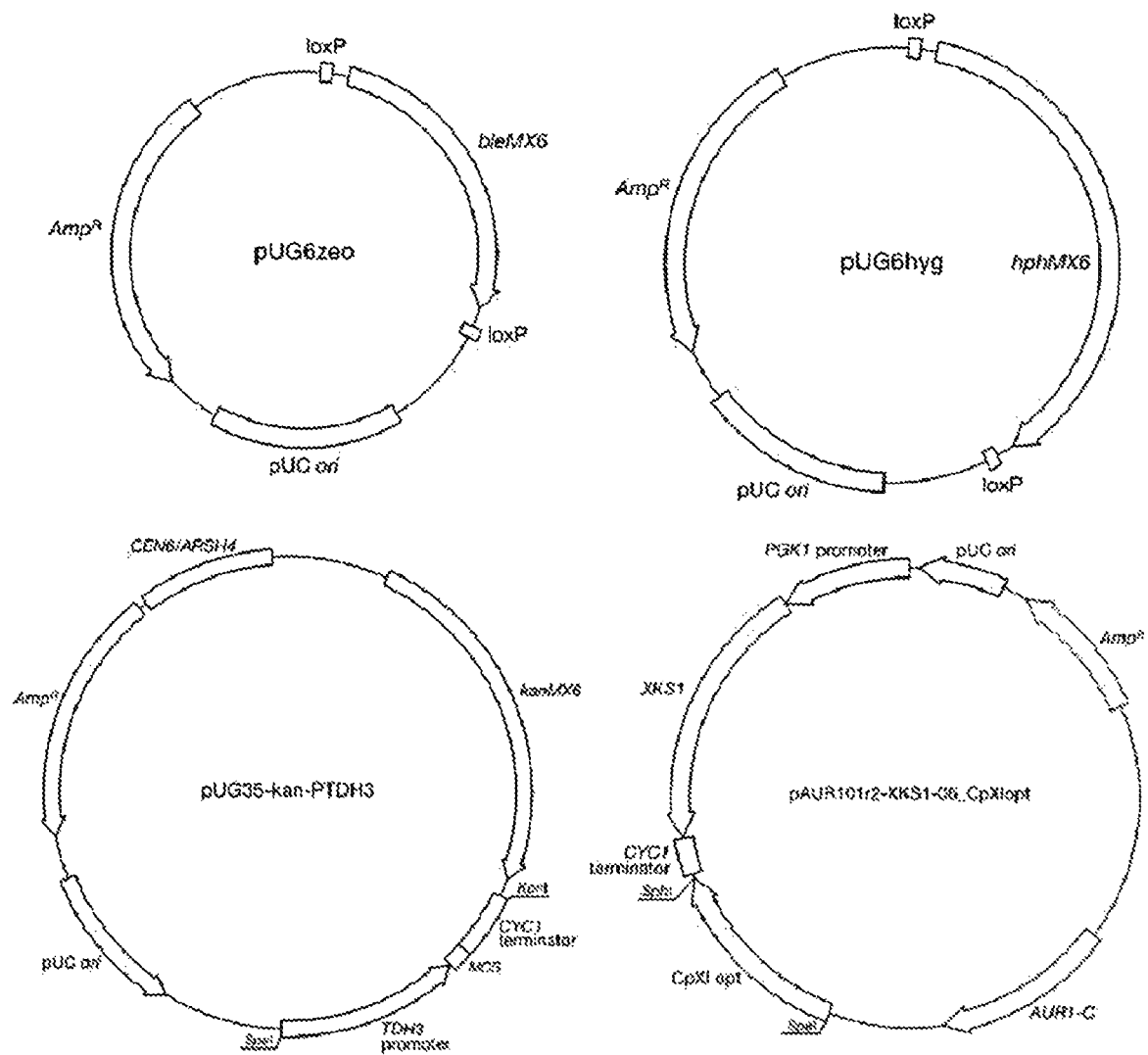
FIG. 1 is a physical map of plasmids: pUG6zeo is a plasmid having the Zeocin™ resistance gene (bleMX6), with loxP sites situated at both ends, introduced into a pUC-based vector skeleton. pUG6hyg is a plasmid having the hygromycin resistance gene (hphMX6), with loxP sites situated at both ends, introduced into a pUC-based vector skeleton. pUG35-kan-TDH3p is a plasmid having a yeast replication origin (CEN6/ARSH4), the Geneticin® resistance gene (kanMX6) and an expression unit for yeast (TDH3 promoter, multicloning site (MCS) and CYC1 terminator) introduced into a pUC-based vector skeleton. pAUR101r2-XKS1-06_CpXIopt is a plasmid having an XKS1 expression unit (PGK1 promoter, XKS1 gene and CYC1 terminator) and the CpXI gene introduced into pAUR101 (Takara Bio, Inc.).

The present invention relates to microorganisms having a xylose isomerase gene with a mutation (mutant CpXI gene), and the use thereof.

Data for the nucleotide sequence of the xylose isomerase gene may be found by sequence analysis using a database such as that of the National Center for Biotechnology Information (NCBI), based on the gene name, or by BLAST using the nucleotide sequence of the gene or the amino acid sequence encoded thereby as the search key. According to the invention, the xylose isomerase gene into which a mutation is to be introduced is a gene from *Clostridium phytofermentans* (also referred to as "CpXI gene"), and the CpXI gene may be either genomic or cDNA. For the Examples of the invention, the artificially synthesized CpXI gene (SEQ ID NO: 12) was used, which is the codon for CpXI (SEQ ID NO: 11) from *Clostridium phytofermentans* ISDg described in NPL 4, optimized for *Saccharomyces cerevisiae* hosts (optimal codon information described in NHL 12). When the host used is a host other than *Saccharomyces cerevisiae*, the optimization is preferably based on the optimal codon information for that host.

According to the invention, multiple mutant CpXI genes having more excellent xylose metabolic capacity than the original CpXI were obtained by applying a method of molecular evolution engineering to the CpXI gene of SEQ ID NO: 12, and of these mutation sites, it was found that mutant CpXI genes having mutations at sites corresponding to threonine at position 63 and valine at position 162 of SEQ ID NO: 11 were superior, and it was confirmed that a double mutant CpXI gene with a combination of the mutations at 2 sites can impart particularly excellent xylose metabolic capacity and ethanol productivity to *Saccharomyces cerevisiae* hosts.

Thus, a mutated protein of *Clostridium phytofermentans* xylose isomerase (CpXI) according to the invention, and a gene coding for it, may have a deletion, substitution or addition of one or more amino acids or nucleotides at any mutation site other than the two disclosed mutation sites, so long as it is functionally equivalent. In the case of a deletion, substitution or addition of several amino acids, this includes, but is not limited to, a deletion, substitution or addition of 2-20, 22, 44, 66, 88 or 132 amino acids, for example. In addition, as mutant proteins and genes coding for them, genes coding for amino acid sequences having at least 70% identity, at least 80% identity, at least 85% identity, at least 90% identity, at least 95% identity, at least 96% identity, at least 97% identity, at least 98% identity or at least 99% identity with respect to the full amino acid sequences, while conserving at least one of the disclosed mutation sites, and still exhibiting growth in the disclosed xylose-containing medium and production of ethanol from xylose, are also encompassed within the scope of the invention. Moreover, the invention also encompasses genes that hybridize with DNA comprising nucleotide sequences that are complementary to the disclosed nucleotide sequences, under stringent conditions, while conserving the codon mutation corresponding to at least one of the disclosed amino acid mutation sites in the genes coding for these mutant proteins. Stringent conditions are well-known in the relevant field, and being sequence-dependent, they differ depending on various conditions, but for example, they include rinsing conditions where rinsing is carried out in 2×SSC and 0.5% SDS for 5 minutes, in 2×SSC and 0.1% SDS for 15 minutes, in 0.1×SSC and 0.5% SDS at 37° C. for 30 to 60 minutes, and then in 0.1×SSC and 0.5% SDS at 68° C. for 30 to 60 minutes, at a temperature Tm of below 12° C. to 20° C., calculated for the hybrids. The mutations can be transferred using Error-prone PCR, or various mutagenic methods.

The promoters regulating expression of the mutant CpXI genes are not limited to HSP12 gene promoters. Specifically, promoters from other genes such as glyceraldehyde-3-phosphate dehydrogenase (TDH3) may be used. Moreover, the terminators are also not limited to CYC1 gene terminators, and terminators from other genes may be used. In addition, the promoters, mutant CpXI genes and terminators may be transferred into yeast in the form of plasmids, or they may be incorporated into the genomic DNA. Also, there is no limit to the number of copies, whether for insertion into plasmids or the genome. For incorporation into genomic DNA, introduction into the genome may be in a site-specific manner, or it may be introduction at random.

The host yeast for introduction of the mutant CpXI gene of the invention may have the genes present in the genome modified or unmodified, so long as they are functionally equivalent, but for metabolism from xylose to xylulose, in order to minimize active inhibition of xylose isomerase (CpXI) by xylitol produced by reverse reaction of endogenous xylose reductase (XR) or xylitol dehydrogenase (XDH), it preferably lacks one or both enzyme genes. Furthermore, in order to augment metabolism from xylulose to xylulose 5-phosphate, it preferably over-expresses endogenous xylulose kinase (XK). The promoter that regulates expression of the xylulose kinase gene is not limited to the PGK1 gene promoter, and other gene promoters may be used. The terminators are also not limited to CYC1 gene terminators, and terminators from other genes may be used. For overexpression of the xylulose kinase gene, the promoter, xylulose kinase gene and terminator may be introduced into yeast in the form of a plasmid, or they may be incorporated into the genomic DNA, in any number of copies. The xylulose kinase gene used may be a gene from any organism. Genes other than those mentioned above from any other organisms may also be introduced. There are no restrictions on the type of recombinant vector and transformation method used for creation of host yeast into which the mutant CpXI gene is to be introduced and introduction of the mutant CpXI gene. So long as it includes xylose, the culture solution may contain other carbon sources, and it is not limited in its constituent components so long as the yeast grow in it.

When a useful substance is to be produced, a culture solution containing at least xylose may be used for the production using yeast of the invention. In this case, the yeast may have, in addition to the mutant CpXI gene disclosed by the invention, also another introduced gene that is suited for production of the useful substance, or a mutant gene. Useful substances are not particularly restricted and include ethanol, xylulose, lactic acid, acetic acid, propanol, isobutanol, butanol, succinic acid and glycerol. Ethanol is particularly preferred to be obtained as the useful substance. Such substances may be substances produced in yeast by reaction of the metabolic enzymes originally in the yeast, or substances that can be produced by introducing enzyme genes necessary for their production into the yeast by gene recombinant technology, and more efficient production is possible by appropriately adjusting the expression levels of the enzymes with reference to a metabolic map. In research for production of such substances, a medium containing glucose as the carbon source is usually used to produce the substances, and by applying the results of the invention to such conventional technology it is possible to using xylose-containing carbon sources for production of these useful substances. That is, the results of the invention can be utilized not only for production of bioethanol but also for production of starting materials for various chemical products.

The yeast host to be transformed using the mutant CpXI gene of the invention may be *Saccharomyces*, *Kluyveromyces*, *Candida*, *Pichia*, *Schizosaccharomyces*, *Hansenula*, or the like. *Saccharomyces* yeast are particularly preferred, examples of which include *Saccharomyces cerevisiae*, *Saccharomyces bayanus* and *Saccharomyces boulardii*.

The type of culturing method is not restricted so long as the yeast grow in xylose-containing culture solution. The culture solution may be a pretreatment solution or saccharified solution containing xylose, obtained by treating a natural substance such as ligneous matter, or it may be an artificial preparation of xylose and other substances. It may also be a solution obtained by adding chemical substances to a solution obtained by treatment of a natural substance. The culturing conditions are not limited in terms of temperature, pH, aerated conditions, stirring speed, culturing time and the like, so long as the yeast grow and metabolize xylose to produce the useful substance. There are also no restrictions on the methods for controlling these conditions. In addition, there are no restrictions on whether or not pretreatment and saccharification treatment are used, or on whether fermentation is conducted simultaneously with saccharification treatment. Purifying treatment of the useful substance after fermentation is also not restricted. A suitable method may be used, according to the type of useful substance.

EXAMPLES

The present invention will now be explained in greater detail, with the understanding that these examples are in no way limitative on the invention.

The other terms and concepts relating to the invention are based on terms and concepts commonly used in the technical field, and the various techniques used for carrying out the invention may be carried out easily and reliably by a person skilled in the art based on the published literature, except for any techniques whose sources are specifically mentioned. The various analyses were conducted by the methods described in the instruction manuals and catalogs included with the analytical instruments or reagents and kits used.

The descriptions in the technical literature, published patent literature and patent application specifications cited throughout the present specification are incorporated as reference as part of the description of the invention.

(Culture Media Used for Examples)

The YPD medium used as yeast growth medium contained 10 g Bacto™ yeast extract (BD Biosciences, USA), 20 g Bacto™ peptone (BD Biosciences) and 20 g D-glucose (hereunder, "glucose", Sigma-Aldrich Co., USA) in 1 L of purified water. The $YPX_{50}$ medium contained 10 g Bacto™ yeast extract, 20 g Bacto™ peptone and 50 g D-xylose (hereunder, "xylose", Sigma-Aldrich Co.) in 1 L of purified water. The $YPX_{80}$ medium contained 10 g Bacto™ yeast extract, 20 g Bacto™ peptone and 80 g xylose in 1 L of purified water. The $YPD_{85}X_{35}$ medium contained 10 g Bacto™ yeast extract, 20 g Bacto™ peptone, 85 g glucose and 35 g xylose in 1 L of purified water. The plate medium was medium having the aforementioned composition with addition of 20 g Bacto™ agar (BD Biosciences) per 1 L of medium.

For construction of yeast strains by genetic engineering, the antibiotics mentioned below were added at different concentrations to the culture media having the aforementioned compositions. 200 μg/mL Geneticin® (Thermo Fisher Scientific, USA), 200 μg/mL Zeocin™ (Thermo Fisher Scientific), 200 μg/mL hygromycin B (Thermo Fisher Scientific), 0.5 μg/mL, aureobasidin A (Takara Bio, Inc.).

Difco™ LB, Miller medium (BD Biosciences) were used for liquid culturing of *E. coli* DH5α, and Difco™ LB Agar, Miller medium (BD Biosciences) were used for culturing in plate medium.

In genetic engineering using *E. coli* DH5α as the host, selective media prepared by adding 100 μg/mL ampicillin (Wako Pure Chemical Industries, Ltd.) to Difco™ LB, Miller medium or Difco™ LB Agar, Miller medium were used.

(Methods of DNA Extraction, PCR and Transformation in Examples)

Plasmid extraction from *E. coli* was carried out by extraction and purification using a QIAprep Spin Miniprep Kit (Qiagen Inc., Germany), according to the manufacturer's protocol. Genomic DNA extraction from yeast was carried out by extraction and purification using a Gen Torukun™ (for yeast) High Recovery (by Takara Bio, Inc., Japan), according to the manufacturer's protocol.

PCR reaction was carried out using KOD-Plus-Neo (Toyobo, Ltd.), preparing a composition of 1×PCR buffer for KOD-Plus-Neo, 0.2 mM dNTPs, 1.5 mM $MgSO_4$, 0.3 μM primer, Template DNA (1 ng), KOD-Plus-Neo DNA polymerase (1 U/μL) in a reaction mixture according to the manufacturer's protocol (50 μL reaction mixture), with 30 cycles of a 3-step cycle (pre-denaturation: 94° C., 2 minutes, denaturation: 98° C., 10 seconds, annealing: Tm temperature, 30 seconds, extension reaction: 68° C., 30 seconds/kb). The annealing temperature was the Tm temperature of the primer used. The extension reaction time was adjusted according to the length of the nucleotide sequence to be amplified. Construction of xylose isomerase gene-expressing plasmids using *E. coli* as the host was carried out using ECOS™ Competent *E. coli* DH5α (Nippon Gene Co., Ltd.), and the transformation method was according to the manufacturer's protocol. The budding yeast transformation was carried out by the lithium acetate method.

(Example 1) Artificial Synthesis of Xylose Isomerase Gene

Amino acid sequence information for 8 types of xylose isomerase genes reported to be able to impart xylose metabolic capacity to budding yeast (*Burkholderia cenocepacia* J2315 (BcXI, Table 1: SEQ ID NO: 1, NPL 7), *Prevotella ruminicola* TC2-24 (PrXI, Table 1: SEQ ID NO: 3, NPL 6), *Ruminococcus flavefaciens* 17 (RfXI, Table 1: SEQ ID NO: 5, NPL 5), *Orpinomyces* sp. ukk1 (OspXI, Table 1: SEQ ID NO: 7, NPL 3), *Piromyces* sp. strain E2 (PspXI, Table 1: SEQ ID NO: 9, NPL 2), *Clostridium phytofermentans* ISDg (CpXI, Table 1: SEQ ID NO: 11, NPL 4), *Clostridium cellulolyticum* H10 (CcXI, Table 1: SEQ ID NO: 13, NFL 8), *Streptomyces rubiginosus* (SrXI, Table 1: SEQ ID NO: 15, NPL 9)) was obtained from the database at the National Center for Biotechnology Information (NCBI).

The codon in each xylose isomerase gene was optimized using an optimized codon table prepared based on a gene group having high gene expression levels in budding yeast (NPL 12) for the amino acid sequence of each xylose isomerase. The obtained nucleotide sequences were a BcXI gene (SEQ ID NO: 2), PrXI gene (SEQ ID NO: 4), RfXI gene (SEQ ID NO: 6), OspXI gene (SEQ ID NO: 8), PspXI gene (SEQ ID NO: 10), CpXI gene (SEQ ID NO: 12), CcXI gene (SEQ ID NO: 14) and SrXI gene (SEQ ID NO: 16), respectively. Artificial synthesis based on these nucleotide sequences was entrusted to Thermo Fisher Scientific, and the respective xylose isomerase genes were obtained.

The xylose isomerase genes used for the research are listed below in Table 1, "Amino acid sequences and nucleotide sequences of xylose isomerase genes used in research", showing their source organism names, the gene names assigned for the research, and their amino acid sequences, GenBank Accession No. and nucleotide sequences after codon optimization.

TABLE 1

| Xylose isomerase gene No. | Source | Name of gene used | SEQ ID NO | GenBank Accession No. | SEQ ID NO |
|---|---|---|---|---|---|
| 1 | *Burkholderia cenocepacia* J2315 | BcXI | SEQ ID NO 1 | CAR57287 | SEQ ID NO 2 |
| 2 | *Prevotella ruminicola* strain TC2-24 | PrXI | SEQ ID NO 3 | KC847096 | SEQ ID NO 4 |
| 3 | *Ruminococcus flavefaciens* 17 | RfXI | SEQ ID NO 5 | CAB51938 | SEQ ID NO 6 |
| 4 | *Orpinomyces* sp. ukk1 | OspXI | SEQ ID NO 7 | ACA65427 | SEQ ID NO 8 |
| 5 | *Piromyces* sp. E2 | PspXI | SEQ ID NO 9 | CAB76571 | SEQ ID NO 10 |
| 6 | *Clostridium phytofermentans* ISDg | CpXI | SEQ ID NO 11 | YP_001558336 | SEQ ID NO 12 |
| 7 | *Clostridium cellulolyticum* H10 | CcXI | SEQ ID NO 13 | YP_002507697 | SEQ ID NO 14 |
| 8 | *Streptomyces rubiginosus* | SrXI | SEQ ID NO 15 | AAA26838 | SEQ ID NO 16 |

(Example 2) Preparation of Host Yeast Strains

As the yeast for evaluation of the xylose metabolism performance of each xylose isomerase, a haploid IR-2 strain was constructed from the diploid practical ethanol-producing yeast strain IR-2 (Table 4, NPL 13).

The specific procedure was as follows. First, the HO gene was disrupted in order to minimize mating-type conversion in the isolated haploid strain. PCR reaction was carried out using pUG6zeo (FIG. 1) as template, and a primer set (Table 2: SEQ ID NO: 17 and 18) having sequences homologous with the promoter region or terminator region of the HO gene at the 5'-ends, to create a DNA fragment having sequences homologous with the promoter region or terminator region of the HO gene added at both ends of the Zeocin resistance gene. Next, using this DNA fragment as template, with a primer set (Table 2: SEQ ID NO: 19 and 20), PCR reaction was conducted in order to further extend the homologous sequences at both ends, to create fragment HO-bleMX6. This fragment was used for transformation of strain IR-2 by homologous recombination, and culturing was carried out for 3 days in Zeocin-added YPD plate medium.

The obtained transformants were cultured overnight with Zeocin-added YPD medium, and then the genomic DNA was extracted from the yeast cells. In order to confirm disruption of the HO gene, a confirmation primer set (Table 2: SEQ ID NO: 21 and 22) was used for PCR reaction with genomic DNA obtained from the transformants as template, to obtain an approximately 1.6 kb DNA fragment. Nucleotide sequence analysis of the obtained fragment allowed discrimination of transformants in which the HO gene had been disrupted. The obtained transformants were sporulated by culturing in sporulation plate medium (10 g potassium acetate and 20 g Bacto™ agar in 1 L of purified water), and the tetrad spores were isolated with a micromanipulator (MSM System series 400, Singer Instruments, UK). The obtained spores were cultured in YPD plate medium, and a haploid strain 2a-3-34A exhibiting the same properties as the parent strain IR-2 (Table 4) was obtained.

Also, in order to minimize catalyst reaction from xylose to xylitol by the xylose reductase gene of the host yeast, the GRE3 gene (xylose reductase gene) was disrupted. PCR reaction was conducted using pUG6hyg (FIG. 1) as template, and using a primer set (SEQ ID NO: 23 and 24) having a sequence homologous with the promoter region or terminator region of the GRE3 gene at the 5'-end, to create a DNA fragment having sequences homologous to the promoter region or terminator region of the GRE3 gene added at both ends of the hygromycin resistance gene, and this DNA fragment was then used as template for PCR reaction using a primer set (Table 2: SEQ ID NO: 25 and 26) to further extend the homologous sequences at both ends, to create fragment GRE3-hphMX6.

This DNA fragment was used for transformation of strain 2a-3-34A by homologous recombination, and culturing was carried out for 3 days in hygromycin B-added YPD plate medium. The obtained transformants were cultured overnight with hygromycin B-added YPD medium, and then the genomic DNA was extracted from the transformant cells. In order to confirm disruption of the GRE3 gene, a GRE3 disruption confirmation primer set (SEQ ID NO: 27 and 28) was used for PCR reaction with genomic DNA obtained from the transformants as template, to obtain an approximately 2 kb DNA fragment. Nucleotide sequence analysis of the obtained fragment allowed discrimination of a transformant with the GRE3 gene disrupted, and the obtained transformant was designated as host yeast strain SS29 (Table 4), for use in the following examples.

The nucleotide sequences of the primers used in this research are shown below in Table 2.

TABLE 2

| Primer No. | Primer name | SEQ ID NO | Base sequence |
|---|---|---|---|
| 1 | IR2_dHO_F1 | SEQ ID NO17 | CAGCAATCAATTCCATCTATACTTTAAACAGCTGAAGCTTCGTACG |
| 2 | IR2_dHO_R1 | SEQ ID NO18 | ACAACTTTTTAAACTAATATACACATTGCATAGGCCACTAGTGGATCT |
| 3 | TS_KO_HO_F2 | SEQ ID NO19 | TCTAAATCCATATCCTTATAAGCAGCAATCAATTCCATCTATACTTTA |
| 4 | TS_KO_HO_R2 | SEQ ID NO20 | TTAAATTTTACTTTTATTACATACAACTTTTTTAAACTAATATACACAT |
| 5 | TS_IR-2_dHO_checkF2 | SEQ ID NO21 | ATTAGGTGTGAAACCACGAAAAA |
| 6 | TS_IR-2_dHO_checkR2 | SEQ ID NO22 | AGGAAAGTTGATCAAGACCCAAT |
| 7 | KO13_IR-2_GRE3_KO_F1 | SEQ ID NO23 | CTTCAAGACGATTGGGAAAATACTCAGCTGAAGCTTCGTACGCT |
| 8 | KO15_IR-2_GRE3_KO_R1 | SEQ ID NO24 | CTCCGTTAAAGTGAACTTTTTTTCGAGCATAGGCCACTAGTGGATCTG |
| 9 | KO14_IR-2_GRE3_KO_F2 | SEQ ID NO25 | GAAGCAAATAGTTGTCAGTGCAATCCTTCAAGACGATTGGGAAAATACT |
| 10 | KO16_IR-2_GRE3_KO_R2 | SEQ ID NO26 | GTGCCAGAAATATCCTTCAATTCTTGCTCCGTTAAAGTGAACTTTTTTCGA |
| 11 | PK47_Check_GRE3_F | SEQ ID NO27 | ACATGCGGAAGAATTTTATGGAAA |
| 12 | PK48_Check_GRE3_R | SEQ ID NO28 | AACCAGGTCCATGGATCATTAAAT |
| 13 | 01_BcXIopt_F1 | SEQ ID NO29 | ATGTCTTACTTCGAACACATCGC |
| 14 | 01_BcXIopt_F1 | SEQ ID NO30 | GCGCCTCGAGACGCAAACCGTAGATAGCTTG |
| 15 | 02_PrXIopt_F1 | SEQ ID NO31 | ATGGCTAAGGAATACTTCCCA |
| 16 | 02_PrXIopt_F1 | SEQ ID NO32 | GCCTCGAGCTTACAGTACAAAGCGACAGTAGTTTC |
| 17 | 03_RfXIopt_F1 | SEQ ID NO33 | ATGGAATTCTTCTCTAACATGGG |
| 18 | 03_RfXIopt_F1 | SEQ ID NO34 | GCGCCTCGAGCAAAGAGAACAAGACGTTGTTGAC |

TABLE 2-continued

| Primer No. | Primer name | SEQ ID NO | Base sequence |
|---|---|---|---|
| 19 | 04_OspXIopt_F1 | SEQ ID NO35 | ATGACTAAGGAATACTTCCCAACTAT |
| 20 | 04_OspXIopt_F1 | SEQ ID NO36 | GCGCCTCGAGTTGGTACATAGCGACGATAGCTT |
| 21 | 05_PspXIopt_F1 | SEQ ID NO37 | ATGGCTAAGGAATACTTCGCAC |
| 22 | 05_PspXIopt_F1 | SEQ ID NO38 | GCGCCTCGAGTTGGTACATAGCGACGATAGCTT |
| 23 | 06_CpXIopt_F1 | SEQ ID NO39 | ATGAAGAACTACTTCCCAAACGTGC |
| 24 | 06_CpXIopt_F1 | SEQ ID NO40 | GCGCCTCGAGTCTGAACAAGATGTTGTTGACGA |
| 25 | 07_CoXIopt_F1 | SEQ ID NO41 | ATGTCTGAAGTCTTCTCTGGTATCTC |
| 26 | 07_CoXIopt_F1 | SEQ ID NO42 | GCGCCTCGAGCTTAGTTTCCAAGATGTATTGGTTC |
| 27 | 08_SrXIopt_F1 | SEQ ID NO43 | ATGAACTACCAACCAACTCCAGA |
| 28 | 08_SrXIopt_F1 | SEQ ID NO44 | GCGCCTCGAGACCTCTAGCACCCAACAAGTG |
| 29 | TCYC1-PPGK1_F | SEQ ID NO45 | TTTGCGGCCGGTACCACTAGTACTGTAATTGCTTT |
| 30 | pUG35-TCYC1R | SEQ ID NO46 | TCGAGAACCCTTAATGGTACCGGCCGCAAATTAAA |
| 31 | oSS62_XI-R_HSP12s | SEQ ID NO47 | ACTCAAAACAAAAAAAACTAAATACAACACCCAT |
| 32 | oSS74_XI-Rc | SEQ ID NO48 | TTGGGAATTGGTCAGTGTCCCAAC |
| 33 | oSS63_XI-R_HSP12as | SEQ ID NO49 | AGTTTTTTTTGTTTTGAGTTGTTTGTTTGAGATT |
| 34 | oSS83_06_CpXI_Fc | SEQ ID NO50 | CTGACCAATTCCCAACTGACGTC |
| 35 | 06_CpXIopt_Seq_F1 | SEQ ID NO51 | TTGGCTTTCTTGAGAAAG |
| 36 | 06_CpXIopt_Seq_R1 | SEQ ID NO52 | TAGCGTGGTTAGCTTCGA |
| 37 | oSS106_06_CpXI_V162A | SEQ ID NO53 | TGTAACGCTGACGCTTTCGCTTACGCT |
| 38 | oSS107_06_CpXI_V162Aas | SEQ ID NO54 | AGAAGTAGAAGCACCGTGCATGAATCTTGG |
| 39 | oSS108_06_CpXI_N303T | SEQ ID NO55 | CAAGGTGACCCAACTTTGGGTTGGGAC |
| 40 | oSS109_06_CpXI_N303Tas | SEQ ID NO56 | GTTAGCGTCGACAGAACCGAAAGCACC |
| 41 | RfXI(Opt)(G179A) | SEQ ID NO57 | GTCAAGTTGGGTGCTAACGGTTACGTCTTC |
| 42 | RfXI(Opt)(G179A)as | SEQ ID NO58 | AGTAGATTGCAAAGCGTTCTTGATT |
| 43 | PspXI(Opt)(E15D) | SEQ ID NO59 | AAGATCAAGTTCGACGGTAAGGACTCTAAG |
| 44 | PspXI(Opt)(E15D)as | SEQ ID NO60 | TTGGATTTGTGGGAAGTATTCCTTA |
| 45 | PspXI(Opt)(T142S) | SEQ ID NO61 | GTTGTTGTGGTCTTCTGCTAACGTCTTGGG |
| 46 | PspXI(Opt)(T142S)as | SEQ ID NO62 | TTGATACGAGTTTCCTTGTGCTTTT |

(Example 3) Construction of Xylose Isomerase Gene Expression System and Introduction into Yeast Strain Using the budding yeast host prepared in Example 2 (strain SS29), it was attempted to express each xylose isomerase by subcloning in the yeast expression vector pLTex321sV5H (Table 3: plasmid No. 3, PTL 2). The subcloning was carried out, specifically, as follows.

Each xylose isomerase gene prepared in Example 1 was amplified by PCR using a corresponding primer set (Table 2: SEQ ID NO: 29 to 44). The reverse primer used for amplification had the XhoI site introduced, and the approximately 1.3 kb amplified DNA fragment was cleaved with XhoI. Simultaneously, a fragment (approximately 7.4 kb) of yeast expression vector pLTex321sV5H cleaved with SmaI and XhoI and an amplified DNA fragment coding for each xylose isomerase were subjected to ligation reaction using TaKaRa Ligation Kit Mighty Mix (Takara Bio, Inc.), according to the manufacturer's protocol. Upon completion of the reaction, each ligation reaction solution was used for transformation of E. coli DH5α, which was cultured overnight in ampicillin-added LB plate medium. The obtained transformants were cultured overnight with ampicillin-added LB medium, the plasmids were extracted, and transformants possessing the target plasmids were discriminated based on restriction enzyme cleavage pattern and nucleotide sequence analysis.

The obtained plasmids containing each of the xylose isomerase genes were cleaved with SpeI and KpnI, and an approximately 2.2 kb fragment comprising the HSP12 promoter, each xylose isomerase gene and the CYC1 terminator was obtained, and ligated in the same manner with a fragment of the yeast expression vector pUG35-kan-PTDH3 cleaved with SpeI and KpnI (FIG. 1, Table 3: plasmid No. 4) (approximately 4.6 kb). Upon completion of the ligation reaction, each ligation reaction solution was used for transformation of E. coli DH5α, which was cultured overnight in ampicillin-added LB plate medium. The obtained transformants were cultured overnight with ampicillin-added LB medium, the plasmids were extracted, and transformants possessing the target plasmid were discriminated based on the restriction enzyme cleavage pattern and nucleotide sequence analysis. The plasmids were extracted from the obtained transformants, to obtain expression plasmids containing each of the xylose isomerase gene expression units.

Also, for overexpression of the xylulose kinase gene (XKS1) that catalyzes reaction from xylulose to xylulose 5-phosphate, the XKS1 gene expression unit was introduced into each of the expression plasmids. The method of introduction was as follows. For amplification of a DNA fragment containing an XKS1 overexpression unit comprising the PGK1 promoter, XKS1 gene and CYC1 terminator, with plasmid pAUR-XRXDHXK (Table 3: plasmid No. 5) which contained the XKS1 gene expression unit as template, amplification was carried out by PCR using an XKS1 overexpression unit primer set (Table 2: SEQ ID NO: 45 and 46). The approximately 2.9 kb amplified DNA fragment and the aforementioned expression plasmid fragment cleaved with KpnI were subjected to In-Fusion reaction using an In-Fusion® HD Cloning Kit (Takara Bio, Inc.), according to the manufacturer's protocol. Upon completion of the reaction, the In-Fusion reaction mixture was used for transformation of E. coli DH5α, which was cultured overnight in ampicillin-added LB plate medium. The obtained transformants were cultured overnight with ampicillin-added LB medium, the plasmids were extracted, and a transformant possessing the target plasmid was obtained based on the restriction enzyme cleavage pattern and nucleotide sequence analysis. The plasmids were extracted from the obtained transformants, to obtain plasmids (Table 3: plasmid No. 7 to 14) containing each of the xylose isomerase gene expression units and the xylulose kinase gene expression unit. Plasmids with the expression unit alone containing no XI were also created by the same method (Table 3: plasmid No. 6).

The obtained plasmids were used for transformation of strain SS29. Transformation of strain SS29 was carried out by the lithium acetate method, and culturing was carried out for 3 days with Geneticin®-added YPD plate medium to obtain transformants of strain SS29 possessing plasmids containing each xylose isomerase gene expression unit and the xylulose kinase gene expression unit. The obtained transformants were designated as strains SS36 to SS44, respectively (Table 4: strain Nos. 4 to 12).

Below, the plasmids used for the research are shown in Table 3 and the genotypes of the yeast strains used for the research are shown in Table 4.

TABLE 3

| Plasmid No. | Plasmid name |
| --- | --- |
| 1 | pUG8zeo |
| 2 | pUG6hyg |
| 3 | pLTex32IsV5H |
| 4 | pUG35-kan-PTDH3p |
| 5 | pAUR-XRXDHXK |
| 6 | pUG35-kan-HSP12p-CYC1t-PGK1p-XKS1-CYC1t |
| 7 | pUG35-kan-HSP12p-BcXI-CYC1t-PGK1p-XKS1-CYC1t |
| 8 | pUG35-kan-HSP12p-PrXI-CYC1t-PGK1p-XKS1-CYC1t |
| 9 | pUG35-kan-HSP12p-RfXI-CYC1t-PGK1p-XKS1-CYC1t |
| 10 | pUG35-kan-HSP12p-OspXI-CYC1t-PGK1p-XKS1-CYC1t |
| 11 | pUG35-kan-HSP12p-PspXI-CYC1t-PGK1p-XKS1-CYC1t |
| 12 | pUG35-kan-HSP12p-CpXI-CYC1t-PGK1p-XKS1-CYC1t |
| 13 | pUG35-kan-HSP12p-CcXI-CYC1t-PGK1p-XKS1-CYC1t |
| 14 | pUG35-kan-HSP12p-SrXI-CYC1t-PGK1p-XKS1-CYC1t |
| 15 | pUG35-kan-HSP12p-RfXI(G179A)-CYC1t-PGK1p-XKS1-CYC1t |
| 16 | pUG35-kan-HSP12p-PspXI(E15D)-CYC1t-PGK1p-XKS1-CYC1t |
| 17 | pUG35-kan-HSP12p-PspXI(T142S)-CYC1t-PGK1p-XKS1-CYC1t |
| 18 | pUG35-kan-HSP12p-PspXI(E15D, T142S)-CYC1t-PGK1p-XKS1-CYC1t |
| 19 | pAUR-kanMX6-HSP12p-CpXI-CYC1t-PGK1p-XKS1-CYC1t |
| 20 | pAUR-kanMX6-HSP12p-CpXI(T63I)-CYC1t-PGK1p-XKS1-CYC1t |
| 21 | pAUR-kanMX6-HSP12p-CpXI(K136T, A176T)-CYC1t-PGK1p-XKS1-CYC1t |
| 22 | pAUR-kanMX6-HSP12p-CpXI(Y13H, D228V)-CYC1t-PGK1p-XKS1-CYC1t |
| 23 | pAUR-kanMX6-HSP12p-CpXI(T273A)-CYC1t-PGK1p-XKS1-CYC1t |
| 24 | pAUR-kanMX6-HSP12p-CpXI(D207G)-CYC1t-PGK1p-XKS1-CYC1t |
| 25 | pAUR-kanMX6-HSP12p-CpXI(N223I)-CYC1t-PGK1p-XKS1-CYC1t |
| 26 | pAUR-kanMX6-HSP12p-CpXI(L78S)-CYC1t-PGK1p-XKS1-CYC1t |
| 27 | pAUR-kanMX6-HSP12p-CpXI(E114G)-CYC1t-PGK1p-XKS1-CYC1t |
| 28 | pAUR-kanMX6-HSP12p-CpXI(V162A, N303T)-CYC1t-PGK1p-XKS1-CYC1t |
| 29 | pAUR-kanMX6-HSP12p-CpXI(R191K, E192K)-CYC1t-PGK1p-XKS1-CYC1t |
| 30 | pAUR-kanMX6-HSP12p-CpXI(L304S)-CYC1t-PGK1p-XKS1-CYC1t |
| 31 | pAUR-kanMX6-HSP12p-CpXI(V162A)-CYC1t-PGK1p-XKS1-CYC1t |
| 32 | pAUR-kanMX6-HSP12p-CpXI(N303T)-CYC1t-PGK1p-XKS1-CYC1t |
| 33 | pAUR-kanMX6-HSP12p-CpXI(T63I, V162A)-CYC1t-PGK1p-XKS1-CYC1t |

TABLE 4

| Strain No: | Strain name | Genotype |
|---|---|---|
| 1 | IR-2 | MATa/α, Industrial bioethanol production strain |
| 2 | 2a-3-34A | MATα ho::bleMX6, Haploid strain derived from IR-2 |
| 3 | SS29 | 2a-3-34A gro3::hphMX6 |
| 4 | SS36 | SS29 [pUG35-kan-PHSP12p-CYC1t-PGK1p-XKS1-CYC1t] |
| 5 | SS37 | SS29 [pUG35-kan-HSP12p-BcXI-CYC1t-PGK1p-XKS1-CYC1t] |
| 6 | SS38 | SS29 [pUG35-kan-HSP12p-PrXI-CYC1t-PGK1p-XKS1-CYC1t] |
| 7 | SS39 | SS29 [pUG35-kan-HSP12p-RfXI-CYC1t-PGK1p-XKS1-CYC1t] |
| 8 | SS40 | SS29 [pUG35-kan-HSP12p-OspXI-CYC1t-PGK1p-XKS1-CYC1t] |
| 9 | SS41 | SS29 [pUG35-kan-HSP12p-PspXI-CYC1t-PGK1p-XKS1-CYC1t] |
| 10 | SS42 | SS29 [pUG35-kan-HSP12p-CpXI-CYC1t-PGK1p-XKS1-CYC1t] |
| 11 | SS43 | SS29 [pUG35-kan-HSP12p-CcXI-CYC1t-PGK1p-XKS1-CYC1t] |
| 12 | SS44 | SS29 [pUG35-kan-HSP12p-SrXI-CYC1t-PGK1p-XKS1-CYC1t] |
| 13 | SS45 | SS29 [pUG35-kan-HSP12p-RfXI(G179A)-CYC1t-PGK1p-XKS1-CYC1t] |
| 14 | SS46 | SS29 [pUG35-kan-HSP12p-PspXI(E15D)-CYC1t-PGK1p-XKS1-CYC1t] |
| 15 | SS48 | SS29 [pUG35-kan-HSP12p-PspXI(T142S)-CYC1t-PGK1p-XKS1-CYC1t] |
| 16 | SS51 | SS29 [pUG35-kan-HSP12p-PspXI(E15D, T142S)-CYC1t-PGK1p-XKS1-CYC1t] |
| 17 | SS81 | SS29 AUR1::kanMX6-HSP12p-CpXI-CYC1t-PGK1p-XKS1-CYC1t |
| 18 | SS82 | SS29 AUR1::kanMX6-HSP12p-CpXI(T63I)-CYC1t-PGK1p-XKS1-CYC1t |
| 19 | SS84 | SS29 AUR1::kanMX6-HSP12p-CpXI(K136E, A176T)-CYC1t-PGK1p-XKS1-CYC1t |
| 20 | SS85 | SS29 AUR1::kanMX6-HSP12p-CpXI(Y13H, D228V)-CYC1t-PGK1p-XKS1-CYC1t |
| 21 | SS86 | SS29 AUR1::kanMX6-HSP12p-CpXI(T273A)-CYC1t-PGK1p-XKS1-CYC1t |
| 22 | SS87 | SS29 AUR1::kanMX6-HSP12p-CpXI(D207G)-CYC1t-PGK1p-XKS1-CYC1t |
| 23 | SS88 | SS29 AUR1::kanMX6-HSP12p-CpXI(N223I)-CYC1t-PGK1p-XKS1-CYC1t |
| 24 | SS89 | SS29 AUR1::kanMX6-HSP12p-CpXI(L78S)-CYC1t-PGK1p-XKS1-CYC1t |
| 25 | SS91 | SS29 AUR1::kanMX6-HSP12p-CpXI(E114G)-CYC1t-PGK1p-XKS1-CYC1t |
| 26 | SS92 | SS29 AUR1::kanMX6-HSP12p-CpXI(V162A, N303T)-CYC1t-PGK1p-XKS1-CYC1t |
| 27 | SS93 | SS29 AUR1::kanMX6-HSP12p-CpXI(R191K, E192K)-CYC1t-PGK1p-XKS1-CYC1t |
| 28 | SS94 | SS29 AUR1::kanMX6-HSP12p-CpXI(L304S)-CYC1t-PGK1p-XKS1-CYC1t |
| 29 | SS104 | SS29 AUR1::kanMX6-HSP12p-CpXI(V162A)-CYC1t-PGK1p-XKS1-CYC1t |
| 30 | SS105 | SS29 AUR1::kanMX6-HSP12p-CpXI(N303T)-CYC1t-PGK1p-XKS1-CYC1t |
| 31 | SS120 | SS29 AUR1::kanMX6-HSP12p-CpXI(T63I, V162A)-CYC1t-PGK1p-XKS1-CYC1t |

(Example 4) Growth Test Under Aerobic Conditions

Figure 2:
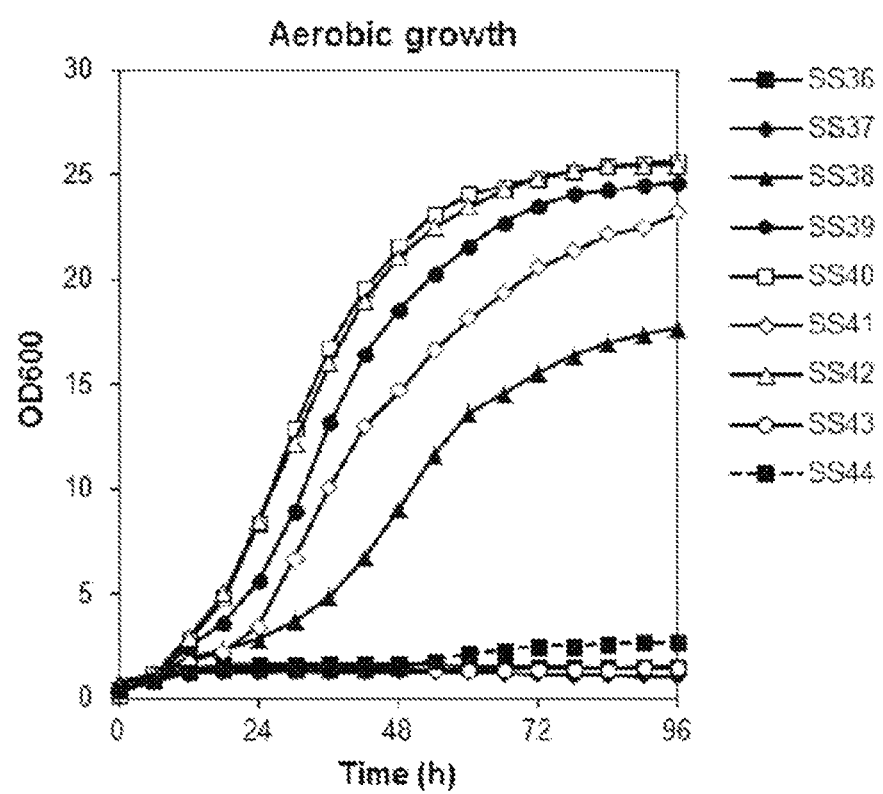
FIG. 2 shows growth of xylose isomerase gene-introduced strains in xylose medium under aerobic conditions: Growth curves for yeast strains having 8 types of xylose isomerase genes introduced (SS37-SS44) and a yeast strain having only an expression vector introduced (SS36), under aerobic conditions using YPX$_{50}$ medium with xylose as the sole carbon source. The data are mean values for three experiments.

In order to evaluate the xylose metabolic capacity due to the xylose isomerases introduced into the yeast strains, a growth test was conducted in $YPX_{50}$ medium. Each of the transformant strains SS36 to SS44 was precultured to the stationary phase in Geneticin®-added YPD medium, the main culture solution was centrifuged to collect the transformant cells, and the cells were rinsed with sterilized water. After dispensing 100 μL of $YPX_{50}$ medium into each well of a 96-well transparent plate, the rinsed transformant cells were inoculated at $OD_{600}$=0.1. Growth of each of the transformants in $YPX_{50}$ medium was carried out by shake culturing at 30° C. using a microplate reader (Infinite® 200 PRO, Tecan Co., Switzerland), with periodic absorbance measurement ($OD_{600}$) during a period of 4 days. The obtained OD value was converted to absorbance in a 1 cm optical path, to obtain a growth curve for each transformant. The results are shown in FIG. 2 and Table 5. Based on the results, strain SS40 containing the OspXI gene exhibited the fastest growth rate, followed by strain SS42 containing the CpXI gene, which exhibited about the same growth rate. On the other hand, the strains containing the BcXI gene, CcXI gene and SrXI gene did not grow in high-concentration xylose medium.

The growth rates in the exponential growth phase, for the strains having 8 types of xylose isomerase genes introduced (SS37-SS44) and a yeast strain having only an expression vector introduced (SS36), under aerobic conditions using $YPX_{50}$ medium with xylose as the sole carbon source, are shown below in Table 5 "Growth rates of xylose isomerase-expressing strains under aerobic conditions". The data are mean values and standard deviations for three experiments. The notation "n.d." indicates that growth was not possible.

TABLE 5

| Strain name | Growth rate (μ)(h−1) |
|---|---|
| SS36 | n.d. |
| SS37 | n.d. |
| SS38 | 0.39 ± 0.05 |
| SS39 | 0.58 ± 0.03 |
| SS40 | 0.71 ± 0.07 |
| SS41 | 0.51 ± 0.10 |
| SS42 | 0.62 ± 0.09 |
| SS43 | n.d. |
| SS44 | 0.03 ± 0.01 |

(Example 5) Fermentation Test Under Microaerobic Conditions

Each of the transformed yeast strains (strains SS36 to SS44) were inoculated into 5 mL of YPD medium (14 mL test tube), and shake cultured for 1 days at 30° C., 150 rpm (preliminary culturing). The total amount of the preliminary culturing solution was inoculated into 50 mL of YPD medium (100 mL baffle-equipped flask), and shake culturing was carried out for 2 days (30° C., 135 rpm) (preculturing). The turbidity of the preculturing solution was approximately $OD_{600}$=20 for all of the strains. The total amount of the preculturing solution was used for collection of the yeast cells by centrifugal separation (3,000 rpm, 5 minutes, 4° C.), and after resuspension in 10 mL of a synthetic saccharified solution ($YPD_{85}X_{35}$ medium: 85 g/L glucose, 35 g/L xylose, 10 g/L yeast extract, 20 g/L peptone), the cells were again collected by centrifugal separation. After rinsing the cells with synthetic saccharified solution, the yeast cells were resuspended in synthetic saccharified solution to a total amount of 10 mL. A 60 mL portion of the synthetic saccharified solution was added to a 100 mL flask, and 10 mL of the cell suspension was inoculated (total: 70 mL). In order to maintain microaerobic conditions during the fermentation, the flask was sealed with a silicon plug which had been penetrated with an injection needle for discharge of carbon dioxide generated during fermentation and an injection needle for sampling of the culture solution. A three-way stopcock was connected to the injection needle for sampling, and was closed during non-sampling periods. The flask was shake cultured at 30° C., 135 rpm for 72 hours. At 0, 1, 3, 6, 12, 24, 36, 48, 60 and 72 hours after the start of culturing, a 2.5 mL syringe was used for periodic sampling of 500 µL of culture solution through the injection needle for sampling.

The sampled culture solution was centrifuged at 15,000 rpm, 4° C. for 5 minutes and 400 µL of the supernatant was cryopreserved at −80° C.

Figure 3:
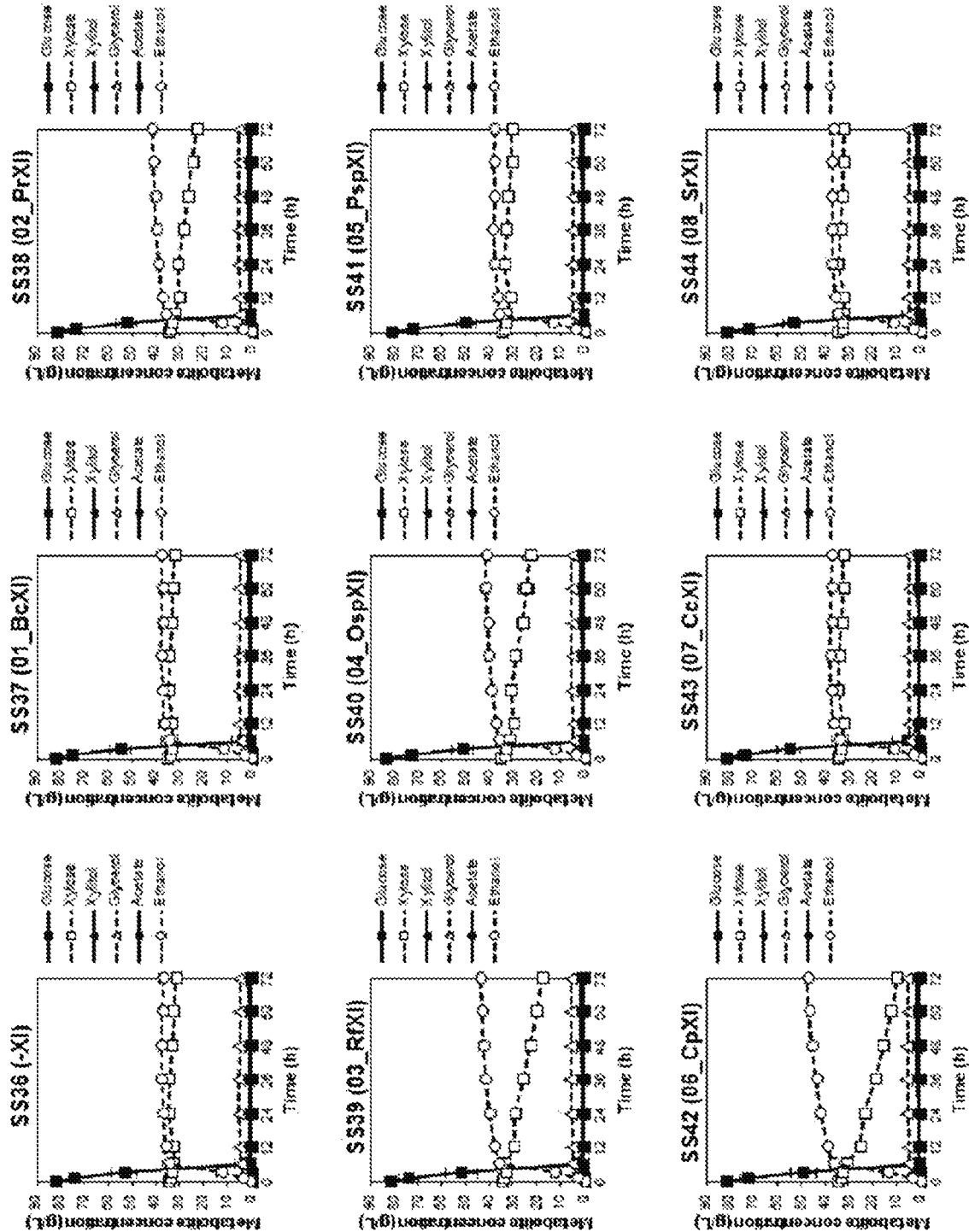
FIG. 3 shows fermentation tests of xylose isomerase gene-introduced strains using a synthetic saccharified solution under microaerobic conditions: Fermentation test results for yeast strains having 8 types of xylose isomerase genes introduced (SS37-SS44) and a yeast strain having only an expression vector introduced (SS36), under microaerobic conditions using a synthetic saccharified solution (YPD$_{85}$X$_{35}$) containing glucose and xylose as carbon sources. During the fermentation tests, the culture supernatants were periodically sampled and the glucose, xylose, xylitol, glycerol, acetic acid and ethanol contents in the culture supernatants were measured by HPLC. The data are mean values for three experiments.

(Example 6) Quantitation of Sugars and Alcohols in Culture Solution of Each Transformed Yeast by HPLC The following measuring method was used for quantitation of the glucose, xylose, xylitol, glycerol, acetic acid and ethanol in the sampled culture solution by high-performance liquid chromatography (HPLC). An HPLC LC-2000 Plus Series (JASCO Corp.) equipped with an Aminex HPX-87C column (Bio-Rad Laboratories, Inc.) and a Cation Refill Guard column (Bio-Rad Laboratories, Inc.) was used for measurement, with 5 mM $H_2SO_4$ as the mobile phase and separation under 65° C. conditions with a flow rate of 0.6 mL/min. A differential refractometer (JASCO Corp.) was used for detection of the substances separated by the column. A 25 µL portion of sample obtained by diluting the sampled culture solution 5-fold with distilled water was analyzed with the HPLC apparatus under the conditions described above. For drawing of a standard curve for quantitation, a standard substance solution comprising a mixture of glucose, xylose, xylitol, glycerol, acetic acid and ethanol at a concentration of 2% (w/v) each, and the test solution serially diluted to 1%, 0.1% and 0.01%, were measured with the HPLC apparatus, a standard curve for quantitation was drawn, and the concentration of each substance in the culture solution sample was quantified. As a result of fermentation testing of each transformed yeast strain (SS36 to SS44) under the conditions described above, strain SS42 (Table 4: strain No. 10) was demonstrated to have the highest xylose metabolic capacity (FIG. 3).

This indicates that the CpXI gene can confer the highest xylose metabolic capacity to the host yeast strain.

(Example 7) Construction of Known Mutant Xylose Isomerase Gene-Introduced Strains and Evaluation of Fermentation Performance (7-1) Construction of Known Mutant Xylose Isomerase Gene-Introduced Strains Strains were prepared having mutant xylose isomerase genes with increased xylose metabolic capacity introduced, as described in NPLs 5 and 10, and their fermentation performance was evaluated.

A mutant RfXI(G179A) gene expression plasmid was prepared by Inverse PCR using the wild type RfXI expression plasmid pUG35-kan-HSP12p-RfXI-CYC1t-PGK1p-XKSI-CYC1t (Table 3: plasmid No. 9) as template, and a primer set (Table 2: RfXI(Opt)(G179A) [SEQ ID NO: 57] and RfXI(Opt)(G179A) as [SEQ ID NO: 58]). The composition of the reaction mixture was prepared as follows, according to the manufacturer's protocol. The composition was 13.4 µL of PCR grade deionized water, 2 µL of 10×PCR Buffer for KOD-Plus-Neo, 2 µL of 2 mM dNTP Mix, 1.2 µL of 25 mM $MgSO_4$, 0.6 µL of 10 µM primer set, 0.4 µL of 1 ng/µL template DNA and 0.4 µL of 1 U/µL KOD-Plus-Neo DNA Polymerase, and 10 cycles of a reaction cycle of predenaturation at 94° C. for 2 minutes followed by denaturation at 98° C. for 10 seconds, annealing at 58° C. for 30 seconds and extension reaction at 68° C. for 5 minutes were carried out, after which a final extension reaction was carried out at 68° C. for 5 minutes. After adding 1.2 µL of DpnI to the obtained PCR product, the mixture was treated at 37° C. for 2 hours. The blunt ends of the obtained linear vector fragments were ligated. The ligation reaction was conducted using T4 DNA Ligase (Takara Bio, Inc.), and the composition of the reaction mixture was adjusted as follows according to the manufacturer's protocol. The composition was 14 µL of distilled water, 2 µL of 10× Ligation Buffer, 1 µL of T4 DNA ligase, 1 µL of T4 Polynucleotide Kinase and 2 µL of linear DNA, and reaction was conducted at room temperature for 1 hour. The reaction mixture was used for transformation of *E. coli* DH5α, which was cultured overnight in ampicillin-added LB plate medium. Several of the obtained transformants were selected, and after culturing each overnight with ampicillin-added LB medium, the plasmids were extracted and nucleotide sequence analysis was performed to obtain plasmid pUG35-kan-HSP12p-RfXI (G179A)-CYC1t-PGK1p-XKS1-CYC1t (Table 3: plasmid No. 15) having the target mutation.

A mutant PspXI(E15D) gene expression plasmid was constructed in the same manner using the wild type PspXI expression plasmid pUG35-kan-HSP12p-PspXI-CYC1t-PGK1p-XKS1-CYC1t (Table 3: plasmid No. 11) as template, and a primer set (PspXI(Opt)(E15D) [SEQ ID NO: 59] and PspXI(Opt)(E15D) as [SEQ ID NO: 60]), to obtain plasmid HSP12p-PspXI(E15D)-CYC1t-PGK1p-XKS1-CYC1t (Table 3: plasmid No. 16) having the target mutation.

A mutant PspXI(T142S) gene expression plasmid was constructed in the same manner using the wild type PspXI expression plasmid pUG35-kan-HSP12p-PspXI-CYC1t-PGK1p-XKS1-CYC1t (Table 3: plasmid No. 11) as template, and a primer set (PspXI(Opt)(T142S) [SEQ ID NO: 61] and PspXI(Opt)(T142S) as [SEQ ID NO: 62]), to obtain plasmid pUG35-kan-HSP12p-PspXI(T142S)-CYC1t-PGK1p-XKS1-CYC1t (Table 3: plasmid No. 17) having the target mutation.

A mutant PspXI(E15D, T142S) gene expression plasmid was constructed in the same manner using pUG35-kan-HSP12p-PspXI(E15D)-CYC1t-PGK1p-XKS1-CYC1t (Table 3: plasmid No. 16) as template, and a primer set (PspXI(Opt)(T142S) [SEQ ID NO: 61] and PspXI(Opt) (T142S)as [SEQ ID NO: 62]), to obtain plasmid pUG35-kan-HSP12p-PspXI(E15D, T142S)-CYC1t-PGK1p-XKS1-CYC1t (Table 3: plasmid No. 18) having the target mutation.

(7-2) Evaluation of Xylose Metabolic Capacity

Figure 7:
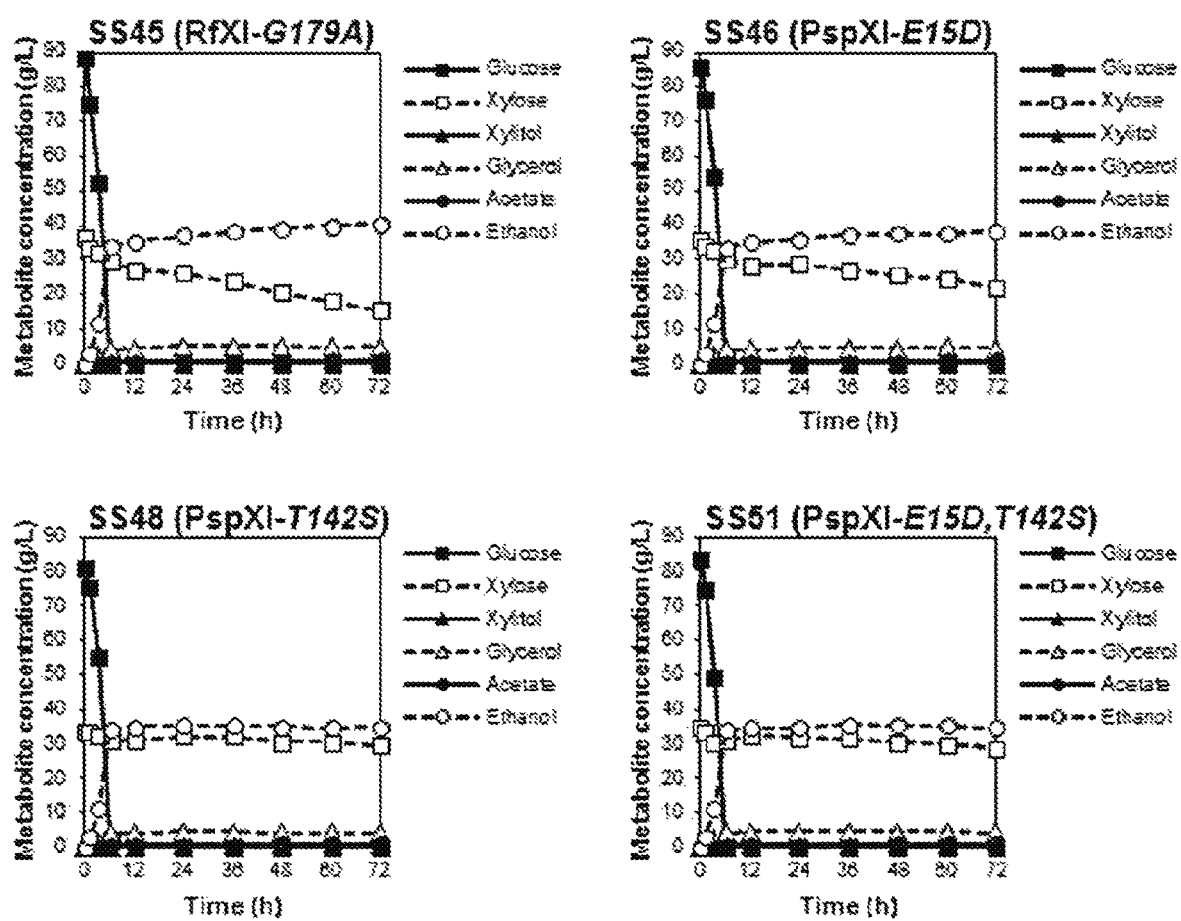
FIG. 7 shows fermentation test results for mutant xylose isomerase gene-introduced strains using a synthetic saccharified solution under microaerobic conditions: There were created a strain (SS45) obtained by introducing into strain SS29 a gene expression plasmid for a mutant RfXI gene (RfXI-G179A) having mutations associated with improved xylose metabolism introduced in RfXI and PspXI described in NPLs 5 and 10, and strains having expression plasmids for mutant PspXI genes (PspXI-E15D, PspXI-T142S and PspXI-E15D, T142S) introduced (SS46, SS48 and SS51, respectively). The fermentation test results shown are for the obtained strains using a synthetic saccharified solution ($YPD_{85}X_{35}$) under microaerobic conditions. During the fermentation test, the culture supernatants were periodically sampled and the glucose, xylose, xylitol, glycerol, acetic acid and ethanol contents were measured by HPLC. The data are mean values for three experiments.

Strain SS29 was transformed using the constructed RfXI (G179A) gene expression plasmid (Table 3: plasmid No. 15), PspXI(E15D) gene expression plasmid (Table 3: plasmid No. 16), PspXI(T142S) gene expression plasmid (Table 3: plasmid No. 17) and PspXI(E15D, T142S) gene expression plasmid (Table 3: plasmid No. 18), to obtain strains SS45 (Table 4: strain No. 13), SS46 (Table 4: strain No. 14), SS48 (Table 4: strain No. 15) and SS51 (Table 4: strain No. 16). For evaluation of the xylose metabolic capacity of these strains, a fermentation test was conducted under microaerobic conditions using a $YPD_{85}X_{35}$ synthetic saccharified solution similar to the one used for Example 5. The culture solutions were periodically sampled in the same manner as Example 5, and the glucose, xylose, xylitol, glycerol, acetic acid and ethanol in the culture solutions were quantified by HPLC. The results are shown in FIG. 7. Upon comparing the fermentation test results for the mutant RfXI gene-expressing strain SS45 and the wild type RfXI gene-expressing strain SS39 (FIG. 3), and comparing the fermentation test results for the mutant PspXI gene-expressing strains SS46, SS48 and SS51 and the wild type PspXI gene-expressing strain SS41 (FIG. 3), no notable increase in xylose metabolic capacity was observed by introduction of the mutations. These results also indicate that the CpXI gene can confer the highest xylose metabolic capacity to the host yeast strain.

(Example 8) Creation of Mutant CpXI Library by Mutagenic PCR

The CpXI gene, which was shown to be able to confer the highest xylose metabolic capacity to host yeast strains based on the fermentation test results of Example 6, was further modified by a molecular evolutionary engineering method, and a mutant CpXI library was created by random mutagenic PCR.

The specific procedure was as follows.

Random mutagenic PCR was conducted with a Diversify PCR Random Mutagenesis Kit (Takara Bio, Inc.), using a CpXI gene-introduced expression plasmid (pUG35-kan-HSP12p-CpXI-CYC1t-PGK1p-XKS1-CYCt, Table 3: plasmid No. 12) as template, and using a primer set having homology with both ends of the mutated sites at regions of approximately 1 kb at the 5'-ends of the CpXI gene (Table 2: oSS62 XI-F_HSP12s [SEQ ID NO: 47] and oSS74 XI-Rc [SEQ ID NO: 48]). The conditions for random mutagenic PCR were set for introduction of mutations at 2.7 locations per 1 kb, according to the manufacturer's protocol. The composition of the random mutagenic PCR reaction mixture was 38 μL of PCR grade deionized water, 5 μL of 10× TITANIUM Taq buffer, 2 μL of 8 mM MnSO$_4$, 1 μL of 2 mM dGTP, 1 μL of 50× Diversify dNTP Mix, 1 μL of 0.02 mM primer set, 1 μL of 1 ng/μL template DNA and 1 μL of TITANIUM Taq Polymerase, and 25 cycles of a reaction cycle of predenaturation at 94° C. for 30 seconds followed by denaturation at 94° C. for 30 seconds and extension reaction at 68° C. for 1 minute were carried out, after which a final extension reaction was carried out at 68° C. for 1 minutes.

The method for the linear vector fragment was as follows. Inverse PCR was conducted using pUG35-kan-HSP12p-CpXI-CYC1t-PGK1p-XKS1-CYC1t as template and a primer set (Table 2: oSS63 XI-R_HSP12as [SEQ ID NO: 49] and oSS83 06_CpXI-Fc [SEQ ID NO: 50]) and KOD-Plus-Neo (Toyobo, Ltd.).

The composition of the reaction mixture was prepared as follows, according to the manufacturer's protocol. The composition was 33.5 μL of PCR grade deionized water, 5 μL of 10×PCR Buffer for KOD-Plus-Neo, 5 μL of 2 mM dNTP Mix, 3 μL of 25 mM MgSO$_4$, 1.5 μL of 10 μM primer set, 1 μL of 1 ng/μL template DNA and 1 μL of 1 U/μL KOD-Plus-Neo DNA Polymerase, and 25 cycles of a reaction cycle of predenaturation at 94° C. for 2 minutes followed by denaturation at 98° C. for 10 seconds, annealing at 58° C. for 30 seconds and extension reaction at 68° C. for 4 minutes were carried out, after which a final extension reaction was carried out at 68° C. for 5 minutes. The obtained mutation CpXI gene fragment and linear vector fragment was subjected to In-Fusion reaction using an In-Fusion® HD Cloning Kit, manufacturer's protocol. The reaction mixture was used for transformation of an *E. coli* DH5α strain (Giga Competent Cell (DH5α), BioDynamics Laboratory, Inc.), and a mutant CpXI library composed of ≥1×10$^4$ DH5α transformants was constructed. In order to confirm the mutation frequency, plasmids were prepared from several of the DH5α transformants and the nucleotide sequence of the CpXI gene was analyzed, confirming that mutations had been introduced at an average of 2 locations, in the CpXI genes of at least 90% of the plasmids. Since these mutations had been introduced independently and throughout the genes, the library was judged to be of extremely high quality.

(Example 9) Screening of Mutant CpXI Genes with Increased Xylose Metabolic Capacity The conditions were examined for screening of mutant CpXI genes with increased xylose metabolic capacity from among the mutant CpXI library constructed in Example 8. A growth test for strain SS42 was conducted using yeast strain SS42 having a wild type CpXI gene expression plasmid (pUG35-kan-HSP12p-CpXI-CYC1t-PGK1p-XKS1-CYC1t, Table 3: plasmid No. 12) introduced, in YPX plate medium with the xylose concentration varied from 50 g/L to 90 g/L (with Geneticin® added to conserve the expression plasmids). Strain SS42 was inoculated into 5 mL of YPD medium and shake cultured at 30° C. (150 rpm). The cells were collected from the culture solution and the cells were rinsed with sterilized water, and then resuspended in sterilized water to OD$_{600}$=1.0×10$^{-4}$. After inoculation of 50 μL of the cell solution into YPX plate medium containing xylose at concentrations of 50 g/L, 60 g/L, 70 g/L, 80 g/L and 90 g/L (YPX$_{50}$, YPX$_{60}$, YPX$_{70}$, YPX$_{80}$ and YPX$_{90}$, respectively), culturing was carried out at 30° C. for 4 days. As a result, colony formation of strain SS42 was observed in the YPX$_{50}$, YPX$_{60}$ and YPX$_{70}$ plate media, but no colony formation was observed in the YPX$_{80}$ and YPX$_{90}$ plate media that contained xylose at 80 g/L or higher.

Considering these results, screening was conducted with xylose-containing medium having a high concentration of ≥80 g/L, in order to screen for mutant CpXI genes with increased xylose metabolic capacity from among the mutant CpXI gene library with strain SS29 as the host.

Expression plasmids containing the mutant CpXI genes were extracted from a mutant CpXI library constructed for *E. coli* DH5α, and the obtained plasmids were used for transformation of strain SS29. The obtained strain SS29 transformants (approximately 2.4×10$^5$ colonies) were inoculated into Geneticin®-added YPX$_{80}$ plate medium and culturing was conducted at 30° C. for 4 days. As a result of screening using the YPX$_{80}$ plate medium, 24 growth-capable strains were obtained that were able to form colonies even in YPX$_{80}$ plate medium.

(Example 10) Second Screening of Mutant CpXI Genes with Increased Xylose Metabolic Capacity It was assumed that the 24 colonies obtained by screening with the high-concentration xylose medium (YPX$_{80}$ plate medium) of Example 9 included not only SS29 transformants with increased xylose metabolic capacity due to mutations in CpXI, but also false-positive strains that had gained the ability to grow in high-concentration xylose medium as well as a result of mutations in the genomic DNA by natural mutation. Therefore, the mutant CpXI expression plasmids were extracted from the SS29 transformants derived from the obtained 24 colonies using an Easy Yeast Plasmid isolation Kit (Takara Bio, Inc.), according to the manufacturer's protocol. Each of the obtained expression plasmids was used for transformation of *E. coli* DH5α (ECOS™ Competent *E. coli* DH5α), and each of the expression plasmids was amplified. As a result of nucleotide sequence analysis of each of the CpXI gene regions from the plasmids obtained from multiple *E. coli* colonies, using primers (Table 2: 06_CpXIopt_F1 [SEQ ID NO: 39], 06_CpXIopt_R1 [SEQ ID NO: 40], 06_CpXIopt_Seq_F1 [SEQ ID NO: 51] and 06_CpXIopt_Seq_R1 [SEQ ID NO: 52]), 18 of the mutant CpXI genes were found to have mutations associated with amino acid substitutions.

The obtained mutant CpXI expression plasmids were then used for repeated transformation of strain SS29. The obtained SS29 transformants were again inoculated into YPX$_{80}$ plate medium and their growth was confirmed, and as a result, growth of 11 SS29 transformants in YPX$_{80}$ plate medium was confirmed. Table 6 below shows amino acid mutations in the mutant CpXI enzymes of the 11 strains.

TABLE 6

| Strain name | Mutated amino acid |
| --- | --- |
| M6-2 | T63I |
| M6-6 | K136T, A176T |
| M6-7 | Y13H, D228V |
| M6-10 | T273A |
| M6-11 | D207G |
| M6-13 | N223I |
| M6-15 | L78S |
| M6-19 | E114G |
| M6-20 | V162A, N303T |
| M6-21 | R191K, E192K |
| M6-22 | L304S |

(Example 11) Third Screening of SS29 Transformants Expressing Mutant CpXI Genes

It was confirmed that the increased xylose metabolic capacity of the 11 SS29 transformants obtained by the second screening in Example 10 was due to the mutated CpXI genes.

Figure 4:
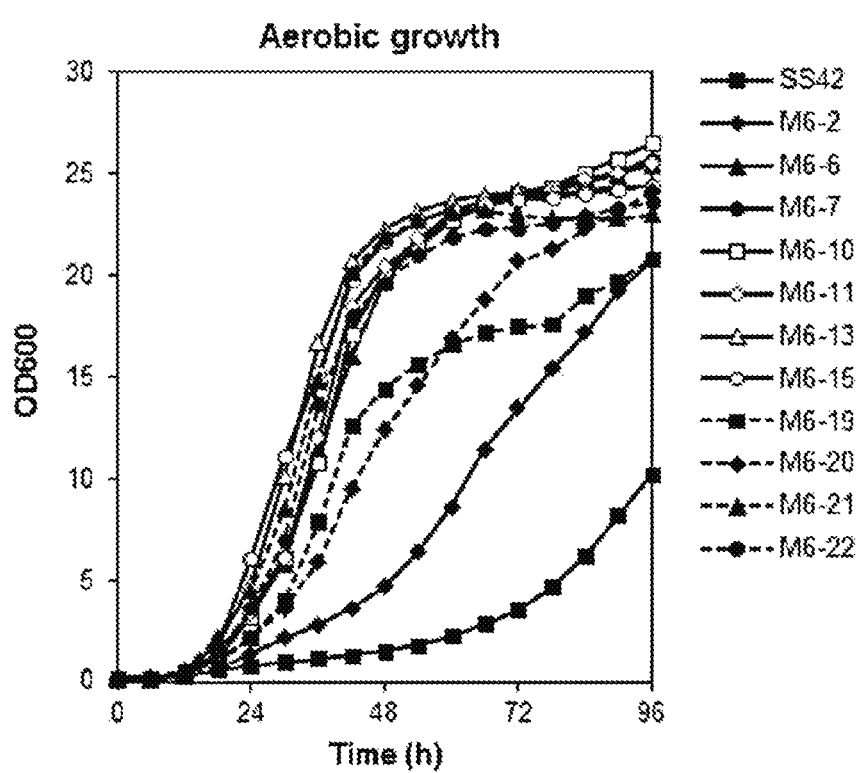
FIG. 4 shows growth of mutant CpXI gene-expressing strains in xylose medium under aerobic conditions: Growth curves for 11 strains M6-2, M6-6, M6-7, M6-10, M6-11, M6-13, M6-15, M6-19, M6-20, M6-21 and M6-22), obtained by introducing mutations into CpXI gene by a molecular evolutionary engineering method, and screening of a mutant CpXI gene library, and for a wild type CpXI-expressing strain (SS42), using $YPX_{80}$ medium under aerobic conditions. The data are mean values for three experiments.
Figure 5:
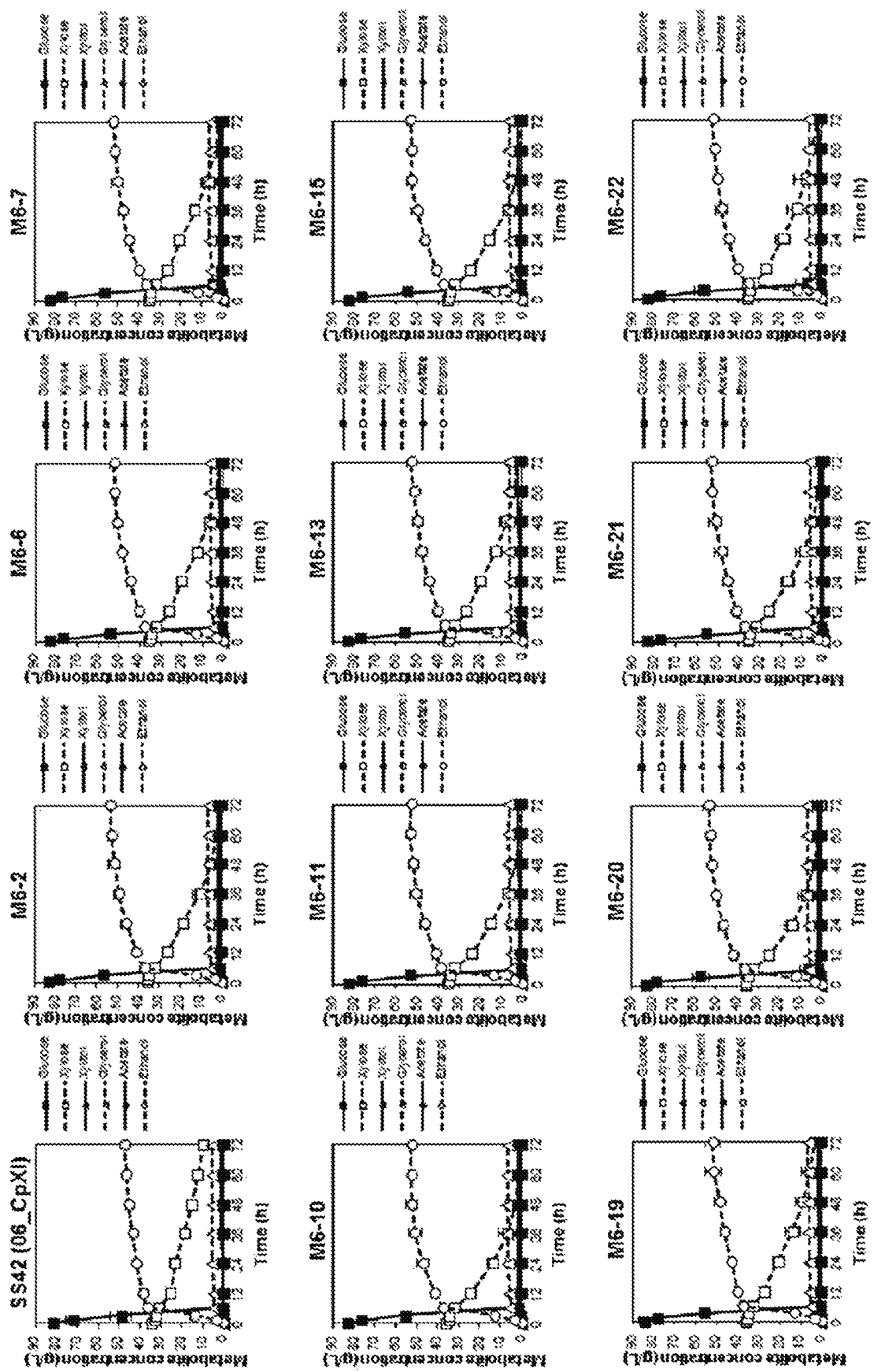
FIG. 5 shows fermentation test results for mutant CpXI gene-expressing strains using a synthetic saccharified solution under microaerobic conditions: Fermentation of 11 strains (M6-2, M6-6, M6-7, M6-10, M6-11, M6-13, M6-15, M6-19, M6-20, M6-21 and M6-22), obtained by introducing mutations into the CpXI gene by a molecular evolutionary engineering method and screening of a mutant CpXI gene library, using a synthetic saccharified solution ($YPD_{85}X_{35}$) under microaerobic conditions. During the fermentation test, the culture supernatants were periodically sampled and the glucose, xylose, xylitol, glycerol, acetic acid and ethanol contents were measured by HPLC. The data are mean values for three experiments.

For additional confirmation of effectiveness, a growth test was conducted in YPX$_{80}$ liquid medium under aerobic conditions, by a method using the aforementioned 96-well microplate. As a result, all of the 11 isolated transformants were observed to have more rapid growth than strain SS42 which expressed the wild type CpXI. The results are shown in FIG. 4 and Table 7. In addition, as a result of a fermentation test using a synthetic saccharified solution (YPD$_{85}$X$_{35}$ medium) conducted by the method described above, it was demonstrated that all of the 11 obtained strains had higher xylose metabolic capacity than the strain SS42 expressing the wild type CpXI, under the fermentation test conditions (FIG. 5).

Shown below in Table 7, "Growth rates of mutant CpXI enzyme gene-introduced strains in xylose medium under aerobic conditions" are the specific growth rates of 11 strains that were obtained by screening of a mutant CpXI gene library, in the exponential growth phase using YPX$_{80}$ medium with xylose as the sole carbon source, under aerobic conditions, and the relative growth rates with respect to the wild type CpXI gene-introduced strain (SS42). The data are mean values for three experiments. The standard deviations of the growth rates are also shown.

TABLE 7

| Clones | Specific growth rate (μ)(h−1) | Relative growth rate (μ/μ0) |
| --- | --- | --- |
| WT (SS42) | 0.27 ± 0.00 | — |
| M6-2 | 0.30 ± 0.03 | 1.13 |
| M6-6 | 0.82 ± 0.31 | 3.04 |
| M6-7 | 0.86 ± 0.16 | 3.20 |
| M6-10 | 0.82 ± 0.07 | 3.06 |
| M6-11 | 0.98 ± 0.12 | 3.63 |
| M6-13 | 1.07 ± 0.06 | 3.97 |
| M6-15 | 0.92 ± 0.18 | 3.43 |
| M6-19 | 0.75 ± 0.08 | 2.80 |
| M6-20 | 0.49 ± 0.03 | 1.81 |
| M6-21 | 0.95 ± 0.11 | 3.54 |
| M6-22 | 0.93 ± 0.09 | 3.44 |

(Example 12) Introduction of Mutant CpXI Genes into Genome

In the screening of Example 9, the expression vectors used were those conserved with low copy numbers in the yeast cells, and it was assumed that the effect of the number of copies of mutant CpXI expression plasmids in the yeast cells may possibly contribute to the increased xylose metabolic capacity of the host yeast cells. Therefore, strains having the 11 screened mutant CpXI gene expression units introduced into the host yeast strain genome were constructed and their fermentation performance was evaluated. The 11 mutant CpXI gene expression plasmids were cleaved with SpeI and SphI to obtain fragments containing HSP12p-CpXI (approximately 2 kb). Separately, pAUR101r2-XKS1-06_CpXIopt (FIG. 1), as a vector having the XKS1 gene expression unit and wild type CpXI gene introduced into the yeast genome introduction vector pAUR101 (Takara Bio. Inc.), was cleaved in the same manner with SpeI and SphI to obtain an approximately 8.3 kb vector fragment. Both DNA fragments were subjected to ligation reaction using TaKaRa DNA Ligation Kit Mighty Mix (Takara Bio, Inc.), according to the manufacturer's protocol. The ligation reaction solution was used for transformation of *E. coli* DH5α (ECOS™ Competent *E. coli* DH5α, Nippon Gene Co., Ltd.), which was inoculated into ampicillin-added LB plate medium and cultured overnight at 37° C. to obtain transformants. The obtained transformants were cultured overnight with ampicillin-added LB medium, the plasmids were extracted, and transformants possessing the target plasmid were discriminated based on the restriction enzyme cleavage pattern and nucleotide sequence analysis. The obtained 11 mutant CpXI gene expression plasmids (Table 3: plasmid Nos. 20 to 30) were cleaved with BsiWI, and the DNA fragment was used for transformation of strain SS29. The transformation reaction mixture was coated onto aureobasidin A-added YPD plate medium, and stationary culturing was carried out at 30° C. for 3 days. This procedure yielded yeast strains having each mutant CpXI expression unit introduced at the AUR1 gene locus of the host strain SS29 (SS82, SS84, SS85, SS86, SS87, SS88, SS89, SS91, SS92, SS93 and SS94 [Table 4: strain Nos. 18 to 28]). As a control, a wild type CpXI expression plasmid (pAUR-kanMX6-HSP12p-CpXI-CYC1t-PGK1p-XKS1-CYC1t [Table 3: plasmid No. 19]) was constructed in the same manner, and used for transformation of strain SS29. The obtained control strain was designated as strain SS81 (Table 4: strain No. 17).

Figure 6A:
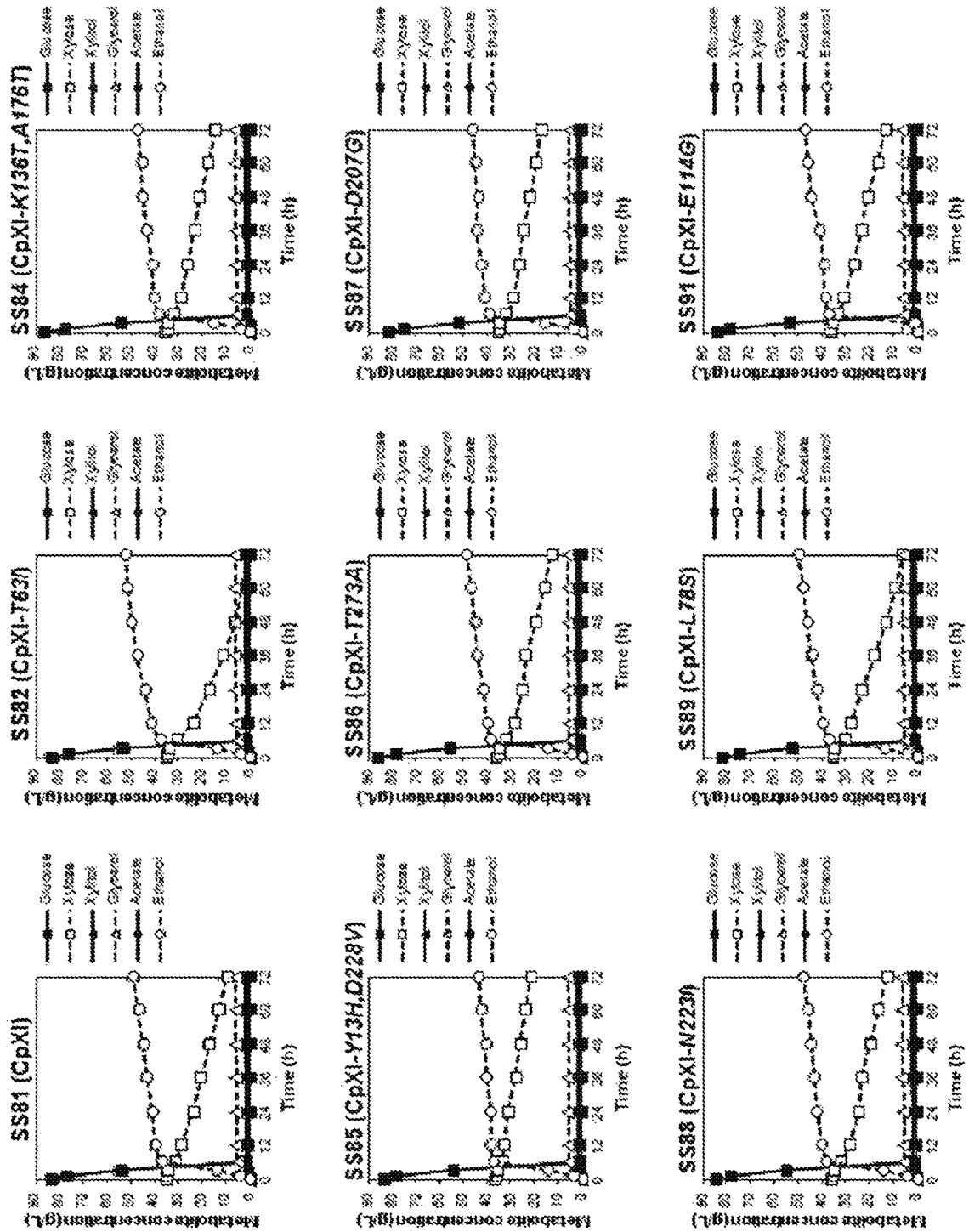
FIG. 6A shows fermentation test results for mutant CpXI gene genome-introduced strains using a synthetic saccharified solution under microaerobic conditions: Fermentation of 8 different strains (SS82 [CpXI-T63I], SS84 [CpXI-K136T, A176T], SS85 [CpXI-Y13H, D228 V], SS86 [CpXI-T273A], SS87 [CpXI-D207G], SS88 [CpXI-N223I], S89 [CpXI-L78S] and SS91 [CpXI-E114G]) among strains obtained by introducing a mutant CpXI gene expression unit into a host yeast strain (SS29), and a strain (SS81) obtained by introducing a wild type CpXI gene expression unit into strain SS29, using a synthetic saccharified solution ($YPD_{85}X_{35}$) under microaerobic conditions. During the fermentation tests (of FIGS. 6A and B), the culture supernatants were periodically sampled and the glucose, xylose, xylitol, glycerol, acetic acid and ethanol contents were measured by HPLC. The data are mean values for three experiments.
Figure 6B:
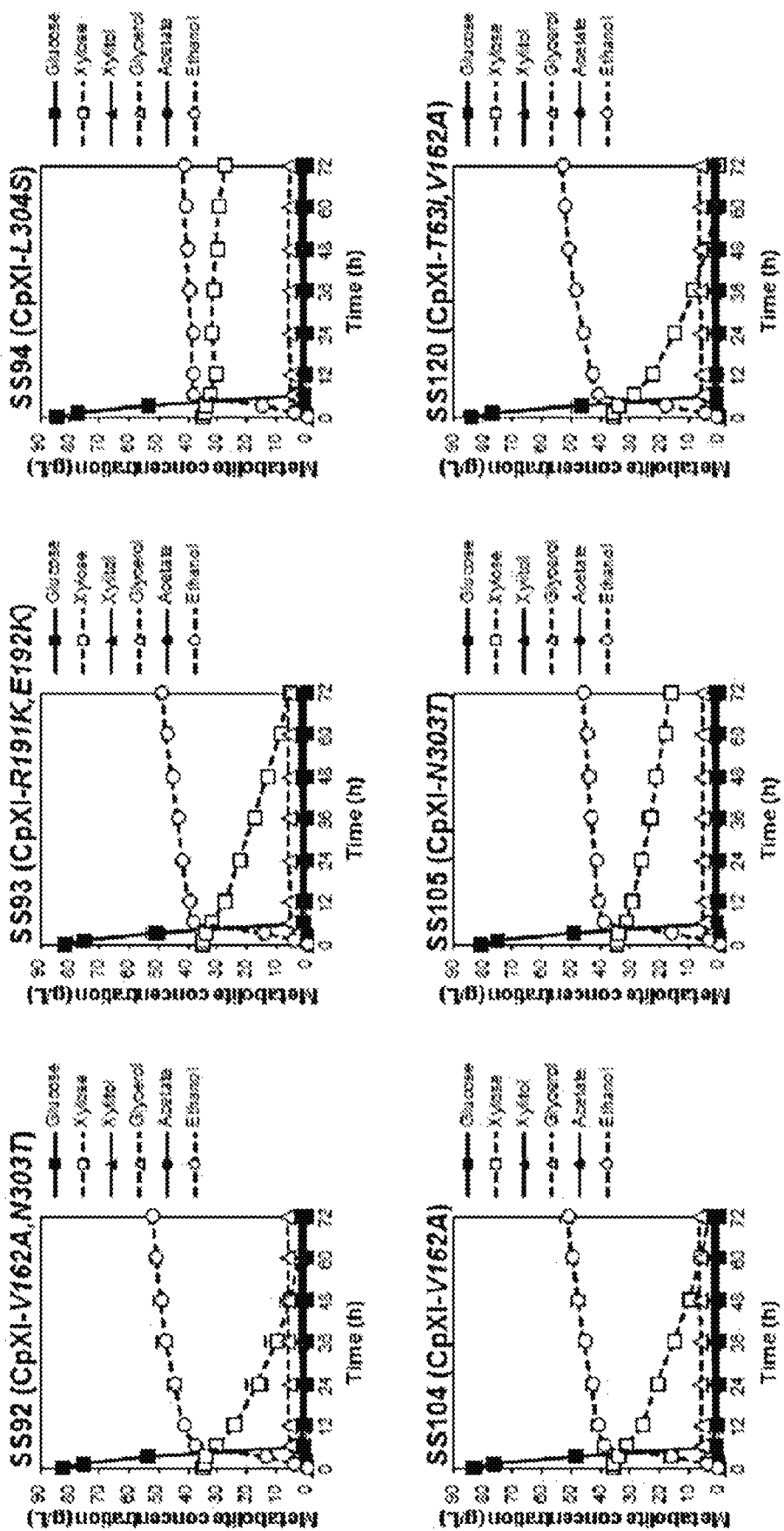
FIG. 6B shows fermentation test results for mutant CpXI gene genome-introduced strains using a synthetic saccharified solution under microaerobic conditions: Fermentation of 3 different strains (SS92 [V162A, N303T], SS93 [CpXI-R191K, E192K] and SS94 [CpXI-L304S]) among strains obtained by introducing a mutant CpXI gene expression unit into a host yeast strain (SS29), strains (SS104 [CpXI-V162A] and SS105 [CpXI-N303T]) having mutations at 2 sites present in the mutant CpXI gene of strain SS92 (V162A and N303T) each introduced into the isolated mutant CpXI gene, and a strain (SS120 [CpXI-T63I, V162A]) having a mutant CpXI gene introduced in which mutations (T63I and V162A) present in the mutant CpXI genes of SS82 [CpXI-T63I] and SS104 [CpXI-V162A] were combined, using a synthetic saccharified solution ($YPD_{85}X_{35}$) under microaerobic conditions.

(Example 13) Fermentation Test in Synthetic Saccharified Solution Under Microaerobic Conditions For evaluation of the xylose metabolic capacity of the 12 SS29 transformants prepared in Example 12 (SS81, SS82, SS84, SS85, SS86, SS87, SS88, SS89, SS91, SS92, SS93 and SS94), a fermentation test was conducted under microaerobic conditions using a $YPD_{85}X_{35}$ synthetic saccharified solution similar to the one used for Example 5. The culture solutions were periodically sampled in the same manner as Example 5, and the glucose, xylose, xylitol, glycerol, acetic acid and ethanol in the culture solutions were quantified by HPLC. The results are shown in FIG. 6. As a result of the fermentation test, 2 strains were selected exhibiting significantly superior xylose metabolic capacity to the strain SS81 expressing the wild type CpXI (strain SS82 and strain SS92).

(Example 14) Xylose Isomerase Activity Measurement

The activities of the xylose isomerases of the two mutant CpXI-expressing strains selected in Example 13, expressed in yeast cells under microaerobic fermentation conditions, were measured by the following method. The culture solution was sampled 24 hours after start of the fermentation test in $YPD_{85}X_{35}$ medium under microaerobic conditions, and the yeast cells were collected by centrifugal separation. The yeast cells were suspended in CelLytic™ Y Cell Lysis Reagent yeast disrupting solution (Sigma Aldrich Japan, KK.) and Protease Inhibitor Cocktail for use with fungal and yeast extracts (Sigma Aldrich Japan, KK.) and 0.5 mm zirconia beads were used for disruption of the cells. After the cell disruption procedure, a supernatant with the zirconia beads and cell insoluble matter removed was obtained by centrifugal separation. A Pierce™ 660 nm Protein Assay Reagent (Thermo Fisher Scientific) was used for protein concentration measurement of the cell disruption solution, quantifying the protein concentration according to the manufacturer's protocol. The xylose isomerase activity in the cell disruption solution was measured by the following method. The composition in 100 µL of reaction mixture was as follows. The compositions were prepared to 100 mM Tris-HCl buffer (pH 8.0), 10 mM $MgCl_2$, 0.3 mM β-NADH (Oriental Yeast Co., Ltd.), 2 U Sorbitol dehydrogenase (Sigma Aldrich Japan, KK.), 1 mg/ml of each cell disruptate, and different concentrations of xylose (10, 50, 100 or 500 mM). The reaction was initiated by addition of the xylose solution, and the change in absorbance at 340 nm at 30° C. was periodically measured using an Infinite® 200 PRO microplate reader. The specific activity was calculated, with 6.25 $mM^{-1}$ $cm^{-1}$ as the molecular absorption coefficient of NADH at 340 nm. The activity measurement results are shown below in Table 8. As a result, high xylose isomerase activity was observed with the mutant CpXI-expressing strains compared to the wild type CpXI-expressing strain. These results matched the fermentation test results for each mutant CpXI-expressing strain under microaerobic conditions. In particular, CpXI-T63I had 38% higher metabolic activity ($V_{max}$) than the wild type, with a Km value of 29.2 mM. Also, CpXI-V162A, N303T had a $V_{max}$ value equivalent to the wild type, but the Km value was 28.4 mM, which was the lowest value for the mutant CpXI.

Table 8 below shows "Kinetic parameters for mutant CpXI enzymes". The table shows the $V_{max}$ values and Km values for xylose isomerase activity in the cell disruption solutions 24 hours after start of culturing, in fermentation testing under microaerobic conditions using the wild type CpXI gene genome-introduced strain (SS81) and the mutant CpXI gene genome-introduced strains (SS82, SS92, SS104, SS105 and SS120). The data are mean values for three experiments. The standard deviations for the $V_{max}$ values are also shown.

TABLE 8

| Stain name | Mutated amino acid | Vmax value (µmol mg protein$^{-1}$ min$^{-1}$) | Km value (mM) |
|---|---|---|---|
| SS81 | WT | 0.066 ± 0.004 | 46.9 |
| SS82 | T63I | 0.091 ± 0.001 | 29.2 |
| SS92 | V162A, N303T | 0.066 ± 0.001 | 28.4 |
| SS104 | V162A | 0.063 ± 0.002 | 29.5 |
| SS105 | N303T | 0.030 ± 0.001 | 19.1 |
| SS120 | T63I, V162A | 0.104 ± 0.003 | 34.4 |

(Example 15) Modification of CpXI by Site-Specific Mutagenesis

In order to examine the respective contributions that the mutations at 2 sites of CpXI-V162A, N303T, among the mutant CpXI genes examined in Example 14, make to increased xylose metabolic capacity, the isolated mutations CpXI-V162A and CpXI-N303T were created by site-specific mutagenesis. The particular site-specific mutagenesis method used was as follows.

Inverse PCR was carried out using the wild type CpXI expression plasmid pAUR-kanMX6-HSP12p-CpXI-CYC1t-PGK1p-XKS1-CYC1t (Table 3: plasmid No. 19) as template and a primer set (Table 2: oSS106 06_CpXI_V162A [SEQ ID NO: 53] and oSS107 06_CpXI_V162Aas [SEQ ID NO: 54]). The composition of the reaction mixture was prepared as follows, according to the manufacturer's protocol. The composition was 13.4 µL of PCR grade deionized water, 2 µL of 10×PCR Buffer for KOD-Plus-Neo, 2 µL of 2 mM dNTP Mix, 1.2 µL of 25 mM $MgSO_4$, 0.6 µL of 10 µM primer set, 0.4 µL of 1 ng/µL template DNA and 0.4 µL of 1 U/µL KOD-Plus-Neo DNA Polymerase, and 10 cycles of a reaction cycle of predenaturation at 94° C. for 2 minutes followed by denaturation at 98° C. for 10 seconds, annealing at 58° C. for 30 seconds and extension reaction at 68° C. for 5 minutes were carried out, after which a final extension reaction was carried out at 68° C. for 5 minutes. After adding 1.2 µL of DpnI to the obtained PCR product, the mixture was treated at 37° C. for 2 hours. The blunt ends of the obtained linear vector fragments were ligated. The ligation reaction was conducted using T4 DNA Ligase (Takara Bio, Inc.), and the composition of the reaction mixture was adjusted as follows according to the manufacturer's protocol. The composition was 14 µL of distilled water, 2 µL of 10× Ligation Buffer, 1 µL of T4 DNA ligase, 1 µL of T4 Polynucleotide Kinase and 2 µL of linear DNA, and reaction was conducted at room temperature for 1 hour. The reaction mixture was used for transformation of *E. coli* DH5α, which was cultured overnight in ampicillin-added LB plate medium. Several of the obtained transformants were selected, and after culturing each overnight with ampicillin-added LB medium, the plasmids were extracted and nucleotide sequence analysis was performed to obtain a plasmid having the target mutation (Table 3: plasmid No. 31). A CpXI-N303T expression plasmid was constructed in the same manner using a primer set (oSS108 06_CpXI_N303T [SEQ ID NO: 55] and oSS109 06_CpXI_N303Tas [SEQ ID NO: 56]), to obtain a plasmid having the target mutation (Table 3: plasmid No. 32).

The created mutant CpXI-V162A gene expression plasmid (Table 3: plasmid No. 31) and CpXI-N303T gene expression plasmid (Table 3: plasmid No. 32) were cleaved with BsiWI and used for transformation of strain SS29. The obtained strains were designated as strain SS104 (Table 4: strain No. 29) and strain SS105 (Table 4: strain No. 30), respectively. A fermentation test was conducted under the same conditions as above, using a synthetic saccharified solution ($YPD_{85}X_{35}$ medium) under microaerobic conditions, and the xylose isomerase activity in the cells of both strains was measured 24 hours after the start of culturing.

As a result, each mutant CpXI exhibited a lower Km value than the wild type CpXI, at 29.5 mM and 19.1 mM, respectively, while the $V_{max}$ value of CpXI (N303T) was 0.03 μmol/mg protein/min, which was a lower value than the wild type CpXI (0.66 μmol/mg protein/min) (Table 8).

In addition, based on the results of the fermentation test, the strain SS104 expressing CpXI-V162A exhibited higher xylose metabolic capacity than strain SS81 expressing the wild type CpXI, but strain SS105 expressing CpXI-N303T had even lower xylose metabolic capacity than strain SS81 (FIG. 5 and Table 9). These results confirmed that the V162A mutation is effective for increasing xylose metabolic capacity of CpXI.

Table 9 below shows "Fermentation test results for CpXI gene-introduced strain using synthetic saccharified solution under microaerobic conditions".

The table shows the fermentation test results for the strain with only the expression vector introduced (SS36), the wild type CpXI gene genome-introduced strain (SS81) and the mutant CpXI gene genome-introduced strains (SS82, SS92, SS120), using the synthetic saccharified solution ($YPD_{85}X_{35}$) under microaerobic conditions. This table also shows the glucose, xylose, xylitol, glycerol, acetic acid and ethanol contents in the culture supernatants 72 hours after start of the fermentation test. Also shown are the produced ethanol yields (% theoretical yield) with respect to the amount of ethanol obtained from the added sugars (glucose and xylose). The data are mean values and standard deviations for three experiments. The notation "n.d." indicates cases below the detection limit in quantitation by HPLC.

position was 13.4 μL of PCR grade deionized water, 2 μL of 10×PCR Buffer for KOD-Plus-Neo, 2 μL of 2 mM dNTP Mix, 1.2 μL of 25 mM $MgSO_4$, 0.6 μL of 10 μM primer set, 0.4 μL of 1 ng/μL template DNA and 0.4 μL of 1 U/μL KOD-Plus-Neo DNA Polymerase, and 10 cycles of a reaction cycle of predenaturation at 94° C. for 2 minutes followed by denaturation at 98° C. for 10 seconds, annealing at 58° C. for 30 seconds and extension reaction at 68° C. for 5 minutes were carried out, after which a final extension reaction was carried out at 68° C. for 5 minutes. After adding 1.2 μL of DpnI to the obtained PCR product, the mixture was treated at 37° C. for 2 hours. The obtained linear vector fragments were subjected to ligation reaction of the blunt ends using T4 DNA Ligase (Takara Bio, Inc.). The composition of the reaction mixture was prepared as follows, according to the manufacturer's protocol. The composition was 14 μL of distilled water, 2 μL of 10× Ligation Buffer, 1 μL of T4 DNA ligase, 1 μL of T4 Polynucleotide Kinase and 2 μL of linear DNA, and reaction was conducted at room temperature for 1 hour. The reaction mixture was used for transformation of E. coli DH5α, which was cultured overnight in ampicillin-added LB plate medium. Several of the obtained transformants were selected, and after culturing each overnight with ampicillin-added LB medium, the plasmids were extracted and nucleotide sequence analysis was performed to obtain a plasmid having the target mutation (Table 3: plasmid No. 33).

The created CpXI (T63I, V162A) gene expression plasmid (Table 3: plasmid No. 33) was cleaved with BsiWI and used for transformation of strain SS29. The obtained double mutant CpXI gene-introduced strain was designated as strain SS120 (Table 4: strain No. 31).

(16-2) Evaluation of CpXI Double Variant

A fermentation test for strain SS120 was conducted under microaerobic conditions, under the same conditions as above, and the xylose isomerase activity in the SS120 cells was measured in the same manner 24 hours after start of the fermentation test. As a result, strain SS120 containing the mutant CpXI (T63I, V162A) gene had a slightly higher Km

TABLE 9

| Strain | Residual glucose (g/L) | Residual xylose (g/L) | Produced xylitol (g/L) | Produced glycerol (g/L) | Produced acetic acid (g/L) | Produced ethanol (g/L) | Theoretical ethanol yield (%) |
|---|---|---|---|---|---|---|---|
| SS36 | n.d. | 31.8 ± 1.2 | 1.2 ± 0.2 | 4.8 ± 0.3 | 1.3 ± 0.2 | 37.2 ± 1.0 | 61.2 ± 0.1 |
| SS81 | n.d. | 9.5 ± 3.5 | 2.2 ± 0.2 | 5.8 ± 0.2 | 1.5 ± 0.1 | 49.2 ± 2.4 | 80.3 ± 2.8 |
| SS82 | n.d. | 1.6 ± 0.5 | 2.1 ± 0.2 | 6.1 ± 0.2 | 1.6 ± 0.1 | 52.3 ± 0.6 | 85.5 ± 2.1 |
| SS92 | n.d. | 1.6 ± 1.0 | 2.1 ± 0.2 | 6.3 ± 0.3 | 1.5 ± 0.1 | 52.3 ± 0.9 | 84.3 ± 2.6 |
| SS120 | n.d. | 0.3 ± 0.3 | 2.2 ± 0.0 | 6.5 ± 0.2 | 1.6 ± 0.0 | 53.3 ± 0.9 | 85.7 ± 1.0 |

(Example 16) Creation and Evaluation of CpXI Double Variant (16-1) Creation of CpXI Double Variant A site-specific mutagenesis method was carried out to create a mutant CpXI (T63I, V162A) with introduction of two different mutations demonstrated to be effective for increasing CpXI xylose metabolic capacity. The specific method was as follows.

Inverse PCR was carried out using the mutant CpXI pAUR-kanMX6-EISP12p-CpXI (T63I)-CYC1t-PGK1p-XKS1-CYC1t (Table 3: plasmid No. 20) as template and a primer set (Table 2: oSS106 06_CpXI_V162A [SEQ ID NO: 53] and oSS107 06_CpXI_V162Aas [SEQ ID NO: 54]). The composition of the reaction mixture was prepared as follows, according to the manufacturer's protocol. The comvalue of 34.4 mM compared to strain SS82 and strain SS92, but the $V_{max}$ value was significantly improved at 0.104 μmol/mg protein/min (Table 8). In addition, the results of the fermentation test under microaerobic conditions also indicated that strain SS120 had the highest xylose metabolic capacity, ethanol production volume and ethanol yield compared to the other constructed strains (FIG. 6 and Table 9). Moreover, in the fermentation test under microaerobic conditions using strain SS120 with the synthetic saccharified solution ($YPD_{85}X_{35}$ medium), as a result of fermentation testing with an initial inoculation at a lower concentration of $OD_{600}=3$ and under higher temperature conditions with the culturing temperature changed to 38° C., most of the glucose and xylose in the synthetic saccharified solution ($YPD_{85}X_{35}$) were consumed within 120 hours, and approximately 53.3 g/L of ethanol was produced. The ethanol conversion efficiency was approximately 87% of the added sugars and approximately 92% of the consumed sugars, and therefore strain SS120 exhibited high xylose metabolic capacity and ethanol production volume even in fermentation with low inoculation concentration and high-temperature conditions.

These results demonstrated that the mutations contributing to increased xylose metabolic capacity in CpXI are the amino acid substitutions T63I and V162A, and in particular that the double mutant CpXI gene simultaneously having mutations at both locations (T63I and V162A) can confer high xylose metabolic capacity and ethanol productivity to host yeast strains.

(16-3) Evaluation on Laboratory Scale

In order to evaluate the double mutant CpXI gene-introduced strain SS120 obtained in (16-1) on the laboratory scale, a simultaneous saccharification and fermentation (SSF) experiment was conducted using NaOH-treated bagasse.

As a result, even in the SSF experiment on a laboratory scale it was possible to produce about 53 g/L of ethanol within 72 h under conditions with an estimated saccharification rate of approximately 85% and 120 g/L sugar production, and high ethanol productivity was demonstrated, with an estimated conversion efficiency of about 91%.

(Example 17) Creation and Evaluation of Saturated Mutation Libraries

Figure 8:
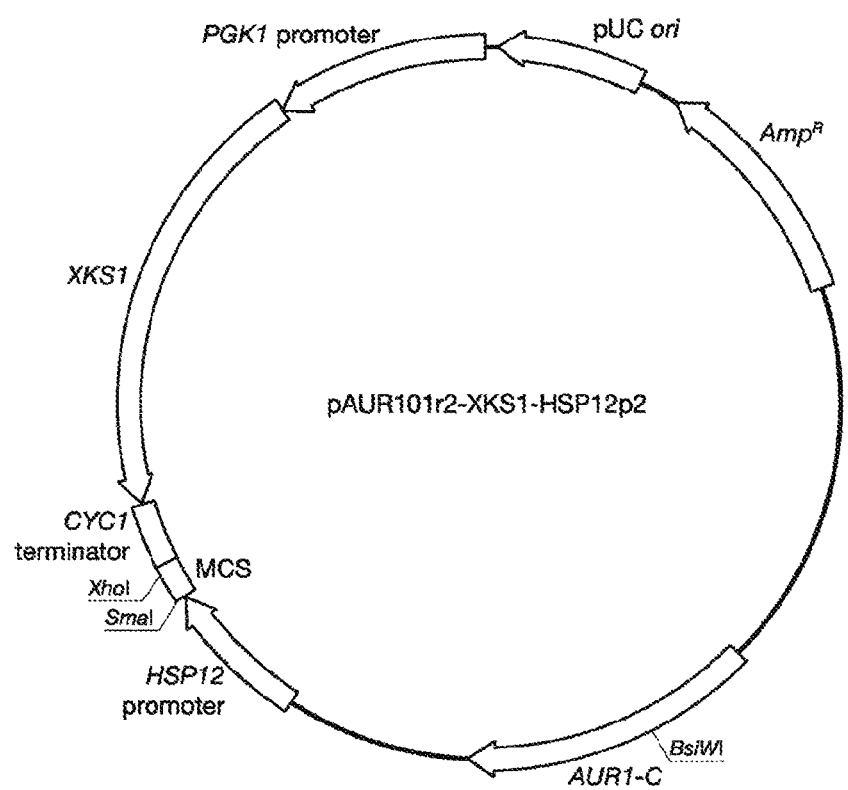
FIG. 8 shows physical maps for plasmids: pAUR101r2-XKS1-HSP12p2 is a plasmid having an XKS1 expression unit (PGK1 promoter, XKS1 gene and CYC1 terminator) and the HSP12 promoter and multicloning site (MCS) introduced into pAUR101 (Takara Bio, FIG. 9 shows growth of a mutant CpXI gene-expressing strain in xylose medium under aerobic conditions: Growth curve for wild type CpXI-expressing strain (T63T) and mutant CpXI-expressing strains (T63I, T63L, T63G, T63H), under aerobic conditions using $YPX_{50}$ medium with xylose as the carbon source. The data are mean values for three experiments.

In order to evaluate the xylose metabolic capacity of mutant CpXI substituted to other amino acid residues at the two mutations identified above (T63I and V162A), saturated mutation libraries for both mutation sites were created. The method was as follows. A vector fragment comprising the XKS1 expression unit, obtained by using SmaI and XhoI to cleave the expression vector pAUR101r2-XKS1-HSP12p2 (FIG. 8) which contained an expression unit comprising the HSP12 promoter, multicloning site and CYC1 terminator, and a mutant CpXI gene fragment having the amino acid residue at position 63 (threonine) or the amino acid residue at position 162 (valine) of CpXI substituted to 18 different amino acid residues (excluding cysteine) different from the wild type amino acid residues, were subjected to ligation reaction, to create a vector fragment-introduced saturated mutation library for each of the mutation sites (GenScript, Japan).

Both saturated mutation libraries were used for transformation of E. coli DH5α, which was cultured overnight in ampicillin-added LB plate medium. Several colonies were selected from the obtained transformants and cultured overnight in ampicillin-added LB medium, and the plasmids were extracted. Nucleotide sequence analysis was used to determine the nucleotide sequences of the mutation sites of the obtained plasmids, obtaining 19 different expression plasmids having threonine at position 63 or valine at position 162 substituted to other amino acid residues (excluding cysteine), comprising the wild type amino acid residues.

The obtained expression plasmids were cleaved with BsiWI (New England Biolabs), and each DNA fragment was used for transformation of strain SS29, which was cultured in aureobasidin A-added YPD plate medium at 30° C. for 3 days to obtain transformants.

Figure 9:
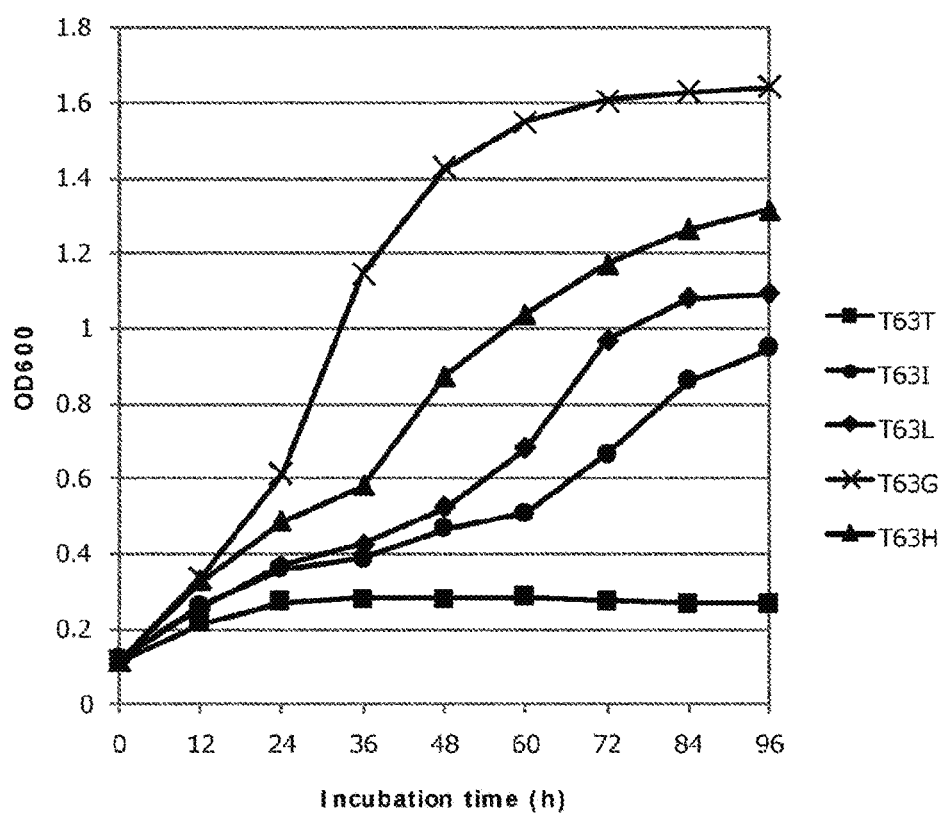

In order to evaluate the xylose metabolic capacity of the obtained transformants, a growth test was conducted in YPX50 medium with xylose as the carbon source, under aerobic conditions. After preculturing each of the transformants in the aureobasidin A-added YPD medium at 30° C. to the stationary phase, the preculturing solution was inoculated into a microplate (transparent, flat-bottom, Corning, Inc.) containing 100 μL of YPX50 medium dispensed in each well, to OD600=0.1 in each well. A microplate reader (Infinite® 200 PRO, Tecan Co.) was used for culturing at 30° C. for 96 hours on the microplate and periodic absorbance measurement (OD600), and a growth curve was obtained for each of the transformants. As a result of the growth test, the amino acid substitutions able to confer to the host yeast strain xylose assimilation equal to or greater than that of the mutant CpXI having the T63I mutation were found to be amino acid substitutions to leucine (T63L), glycine (T63G) and histidine (T63H) (FIG. 9: the nucleotide sequences of mutant CpXI having amino acid substitutions to T63L, T63G and T63H correspond to SEQ ID NO: 63-65, respectively).

INDUSTRIAL APPLICABILITY

According to the invention it is possible to construct yeast strains capable of producing ethanol from xylose at high efficiency, which are expected to be able to contribute to increased efficiency of second generation bioethanol production using biomass as starting material.

SEQUENCE LISTING

Sequence listing.txt

The invention claimed is:

1. A mutant xylose isomerase (CpXI) comprising,
 (a1) a protein consisting of an amino acid sequence wherein Thr63 is substituted to a member selected from the group consisting of isoleucine, leucine, glycine and histidine and/or Val162 is substituted to alanine in the amino acid sequence listed as SEQ ID NO: 11;
 (a2) a protein consisting of an amino acid sequence wherein 1 to 44 amino acids of the amino acid sequence of the protein in (a1) are deleted, substituted or added at a position other than the substituted amino acids at positions 63 and/or 162, or
 (a3) a protein consisting of an amino acid sequence having at least 90% identity to the amino acid sequence of the protein in (a1), wherein an amino acid corresponding to Thr63 is substituted to a member selected from the group consisting of isoleucine, leucine, glycine and histidine, and/or an amino add corresponding to Val162 in the amino acid sequence listed as SEQ ID NO: 11 is substituted to alanine, and
 wherein the mutant CpXI has higher xylose metabolic activity than the wild type CpXI.

2. The mutant CpXI according to claim 1, wherein the mutant CpXI comprises a protein consisting of an amino acid sequence wherein Thr63 is substituted to a member selected from the group consisting of isoleucine, leucine, glycine and histidine and/or Val162 is substituted to alanine in the amino acid sequence listed as SEQ ID NO: 11.

3. The mutant CpXI according to claim 1, wherein the mutant CpXI comprises a protein consisting of an amino acid sequence wherein Thr63 is substituted to a member selected from the group consisting of isoleucine, leucine, glycine and histidine and Val162 is substituted to alanine in the amino acid sequence listed as SEQ ID NO: 11.

4. A mutant CpXI gene encoding the mutant CpXI according to claim 1.

5. The mutant CpXI gene according to claim 4, comprising a nucleotide sequence having a codon mutation in which a codon corresponding to Thr63 is substituted to a codon corresponding to a member selected from the group consisting of isoleucine, leucine, glycine and histidine and/or a codon corresponding to Val162 is substituted to a codon corresponding to alanine in the nucleotide sequence listed as SEQ ID NO: 12.

6. A transformed yeast that has been transformed by the mutant CpXI gene according to claim 4, the yeast having higher xylose metabolic capacity than the parent yeast.

7. The transformed yeast according to claim 6, wherein the yeast is a yeast selected from the group consisting of *Saccharomyces, Kluyveromyces, Candida, Pichia, Schizosaccharomyces* and *Hansenula*.

8. The transformed yeast according to claim 6, wherein the yeast is *Saccharomyces* yeast.

9. A method of producing ethanol, comprising:
 contacting a solution comprising xylose with the transformed yeast according to claim 6 under fermentation conditions to thereby produce ethanol.

10. The mutant CpXI according to claim 1, wherein the proteins in a2 and (a3) have the same function as the protein in (a1).

* * * * *

SEQUENCE LISTING

```
<160> NUMBER OF SEQ ID NOS: 65

<210> SEQ ID NO 1
<211> LENGTH: 440
<212> TYPE: PRT
<213> ORGANISM: Burkholderia cenocepacia J2315

<400> SEQUENCE: 1

Met Ser Tyr Phe Glu His Ile Pro Ala Ile Arg Tyr Glu Gly Pro Gln
1               5                   10                  15

Ser Asp Asn Pro Leu Ala Tyr His His Tyr Asp Pro Asp Lys Arg Val
            20                  25                  30

Leu Gly Lys Thr Leu Ala Glu His Leu Arg Ile Ala Val Cys Tyr Trp
        35                  40                  45
```

His Thr Phe Val Trp Pro Gly His Asp Ile Phe Gly Gln Ala Ala Phe
 50                 55                  60

Arg Arg Pro Trp Gln Gln Pro Gly Asp Ala Leu Glu Arg Ala Arg Met
 65                  70                  75                  80

Lys Ala Asp Ala Ala Phe Glu Phe Phe Thr Lys Leu Gly Thr Pro Phe
                 85                  90                  95

Tyr Thr Phe His Asp Thr Asp Val Ala Pro Glu Gly Asp Ser Leu Arg
            100                 105                 110

Glu Tyr Ala Ala Asn Phe Ala Arg Met Val Asp Tyr Leu Gly Glu Arg
            115                 120                 125

Gln Gln Ala Ser Gly Val Arg Leu Leu Trp Gly Thr Ala Asn Leu Phe
        130                 135                 140

Ser His Pro Arg Phe Ala Ala Gly Ala Ala Thr Asn Pro Asn Pro Asp
145                 150                 155                 160

Val Phe Ala Trp Ala Ala Thr Gln Val Cys His Ala Leu Asp Ala Thr
                165                 170                 175

His Arg Leu Gly Gly Glu Asn Tyr Val Leu Trp Gly Gly Arg Glu Gly
            180                 185                 190

Tyr Glu Thr Leu Leu Asn Thr Asp Leu Lys Arg Glu Arg Asp Gln Phe
        195                 200                 205

Ala Arg Phe Leu Ser Met Val Val Glu His Lys His Arg Ile Gly Phe
210                 215                 220

Lys Gly Ala Leu Leu Ile Glu Pro Lys Pro Gln Glu Pro Thr Lys His
225                 230                 235                 240

Gln Tyr Asp Tyr Asp Val Ala Thr Val His Gly Phe Leu Val Gln Tyr
                245                 250                 255

Gly Leu Gln Asn Glu Ile Arg Val Asn Ile Glu Ala Asn His Ala Thr
            260                 265                 270

Leu Ala Gly His Ser Phe His His Glu Ile Ala Asn Ala Phe Ala Leu
        275                 280                 285

Gly Val Phe Gly Ser Val Asp Ala Asn Arg Gly Asp Pro Gln Asn Gly
290                 295                 300

Trp Asp Thr Asp Gln Phe Pro Asn Ser Val Glu Glu Leu Thr Leu Ala
305                 310                 315                 320

Phe Tyr Glu Ile Leu Arg His Gly Gly Phe Thr Thr Gly Gly Met Asn
                325                 330                 335

Phe Asp Ala Lys Val Arg Arg Gln Ser Ile Asp Pro Glu Asp Leu Phe
            340                 345                 350

Tyr Gly His Val Gly Ala Ile Asp Val Leu Ala Leu Ala Leu Glu Arg
        355                 360                 365

Ala Ala Val Leu Val Glu Asn Asp Arg Leu Asp Ala Leu Arg Arg Gln
370                 375                 380

Arg Tyr Ala Gln Trp Asp Asp Ala Phe Gly Arg Lys Ile Leu Ala Gly
385                 390                 395                 400

Gly Tyr Thr Leu Glu Ser Leu Ala Ala Asp Ala Leu Ala Arg Gly Val
                405                 410                 415

Asp Pro Gln His Ala Ser Gly Ala Gln Glu Arg Leu Glu Asn Ile Val
            420                 425                 430

Asn Gln Ala Ile Tyr Gly Leu Arg
        435                 440

<210> SEQ ID NO 2
<211> LENGTH: 1323

<212> TYPE: DNA
<213> ORGANISM: Burkholderia cenocepacia J2315

<400> SEQUENCE: 2

```
atgtcttact tcgaacacat cccagctatc cgttacgaag gtccacaatc tgacaaccca      60
ttggcttacc accactacga cccagacaag cgtgtcttgg gtaagacttt ggctgaacac     120
ttgcgtatcg ctgtctgtta ctggcacact ttcgtctggc caggtcacga catcttcggt     180
caagctgctt ccgtcgtcc atggcaacaa ccaggtgacg ctttggaacg tgctcgtatg     240
aaggctgacg ctgctttcga attcttcact aagttgggta ctccattcta cactttccac     300
gacactgacg tcgctccaga aggtgactct ttgcgtgaat acgctgctaa cttcgctcgt     360
atggtcgact acttgggtga acgtcaacaa gcttctggtg tccgtttgtt gtggggtact     420
gctaacttgt tctctcaccc acgtttcgct gctggtgctg ctactaaccc aaacccagac     480
gtcttcgctt gggctgctac tcaagtctgt cacgctttgg acgctactca ccgtttgggt     540
ggtgaaaact acgtcttgtg gggtggtcgt gaaggttacg aaactttgtt gaacactgac     600
ttgaagcgtg aacgtgacca attcgctcgt ttcttgtcta tggtcgtcga cacaagcac      660
cgtatcggtt caagggtgc tttgttgatc gaaccaaagc acaagaaacc aactaagcac     720
caatacgact acgacgtcgc tactgtccac ggtttcttgg tccaatacgg tttgcaaaac     780
gaaatccgtg tcaacatcga agctaaccac gctactttgg ctggtcactc tttccaccac     840
gaaatcgcta acgctttcgc tttgggtgtc ttcggttctg tcgacgctaa ccgtggtgac     900
ccacaaaacg gttgggacac tgaccaattc ccaaactctg tcgaagaatt gactttggct     960
ttctacgaaa tcttgcgtca cggtggtttc actactggtg gtatgaactt cgacgctaag    1020
gtccgtcgtc aatctatcga cccagaagac ttgttctacg gtcacgtcgg tgctatcgac    1080
gtcttggctt tggctttgga acgtgctgct gtcttggtcg aaaacgaccg tttggacgct    1140
ttgcgtcgtc aacgttacgc tcaatgggac gacgctttcg gtcgtaagat cttggctggt    1200
ggttacactt tggaatcttt ggctgctgac gctttggctc gtggtgtcga cccacaacac    1260
gcttctggtg ctcaagaacg tttggaaaac atcgtcaacc aagctatcta cggtttgcgt    1320
taa                                                                  1323
```

<210> SEQ ID NO 3
<211> LENGTH: 439
<212> TYPE: PRT
<213> ORGANISM: Prevotella ruminicola strain TC2-24

<400> SEQUENCE: 3

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
            100                 105                 110
```

Ile Ala Glu Tyr Glu Arg Arg Met Lys Glu Ile Thr Asp Tyr Ala Leu
            115                 120                 125
Val Lys Met Lys Glu Tyr Pro Asn Ile Lys Leu Leu Trp Gly Thr Ala
        130                 135                 140
Asn Val Phe Gly Asn Lys Arg Tyr Ala Asn Gly Ala Ser Thr Asn Pro
145                 150                 155                 160
Asp Phe Asp Val Val Ala Arg Ala Ile Val Gln Ile Lys Asn Ala Ile
                165                 170                 175
Asp Ala Thr Ile Lys Leu Gly Gly Thr Asn Tyr Val Phe Trp Gly Gly
            180                 185                 190
Arg Glu Gly Tyr Met Ser Leu Leu Asn Thr Asp Gln Lys Arg Glu Lys
        195                 200                 205
Glu His Met Ala Thr Met Leu Thr Met Ala Arg Asp Tyr Ala Arg Ala
    210                 215                 220
Lys Gly Phe Lys Gly Thr Phe Leu Ile Glu Pro Lys Pro Met Glu Pro
225                 230                 235                 240
Ser Lys His Gln Tyr Asp Val Asp Thr Glu Thr Val Cys Gly Phe Leu
                245                 250                 255
Arg Ala His Gly Leu Asp Lys Asp Phe Lys Val Asn Ile Glu Val Asn
            260                 265                 270
His Ala Thr Leu Ala Gly His Thr Phe Glu His Glu Leu Ala Cys Ala
        275                 280                 285
Val Asp Asn Gly Met Leu Gly Ser Ile Asp Ala Asn Arg Gly Asp Ala
    290                 295                 300
Gln Asn Gly Trp Asp Thr Asp Gln Phe Pro Ile Asp Asn Phe Glu Leu
305                 310                 315                 320
Thr Gln Ala Met Leu Glu Ile Ile Arg Asn Gly Gly Leu Gly Asn Gly
                325                 330                 335
Gly Thr Asn Phe Asp Ala Lys Ile Arg Arg Asn Ser Thr Asp Leu Glu
            340                 345                 350
Asp Leu Phe Ile Ala His Ile Ser Gly Met Asp Ala Met Ala Arg Ala
        355                 360                 365
Leu Met Asn Ala Ala Ala Ile Leu Glu Glu Ser Glu Leu Pro Lys Met
    370                 375                 380
Lys Lys Glu Arg Tyr Ala Ser Phe Asp Asn Gly Ile Gly Lys Asp Phe
385                 390                 395                 400
Glu Asp Gly Lys Leu Thr Leu Glu Gln Ala Tyr Glu Tyr Gly Lys Lys
                405                 410                 415
Val Glu Glu Pro Lys Gln Thr Ser Gly Lys Gln Glu Lys Tyr Glu Thr
            420                 425                 430
Thr Val Ala Leu Tyr Cys Lys
        435

<210> SEQ ID NO 4
<211> LENGTH: 1320
<212> TYPE: DNA
<213> ORGANISM: Prevotella ruminicola strain TC2-24

<400> SEQUENCE: 4
atggctaagg aatacttccc attcactggt aagatcccat tcgaaggtaa ggactctaag    60
aacgtcatgg ctttccacta ctacgaacca gaaaaggtcg tcatgggtaa gaagatgaag   120
gactggttga agttcgctat ggcttggtgg cacactttgg gtggtgcttc tgctgaccaa   180
ttcggtggtc aaactagatc ttacgaatgg gacaaggctg ctgacgctgt ccaaagagct   240

```
aaggacaaga tggacgctgg tttcgaaatc atggacaagt tgggtatcga atacttctgt    300
ttccacgacg tcgacttggt cgaagaaggt gaaactatcg ctgaatacga aagaagaatg    360
aaggaaatca ctgactacgc tttggtcaag atgaaggaat acccaaacat caagttgttg    420
tggggtactg ctaacgtctt cggtaacaag agatacgcta acggtgcttc tactaaccca    480
gacttcgacg tcgtcgctag agctatcgtc caaatcaaga acgctatcga cgctactatc    540
aagtggggtg gtactaacta cgtcttctgg ggtggtagag aaggttacat gtctttgttg    600
aacactgacc aaaagagaga aaggaacac atggctacta tgttgactat ggctagagac    660
tacgctagag ctaagggttt caagggtact ttcttgatcg aaccaaagcc aatggaacca    720
tctaagcacc aatacgacgt cgacactgaa actgtctgtg gtttcttgag agctcacggt    780
ttggacaagg acttcaaggt caacatcgaa gtcaaccacg ctactttggc tggtcacact    840
ttcgaacacg aattggcttg tgctgtcgac aacggtatgt tgggttctat cgacgctaac    900
agaggtgacc tcaaaacgg ttgggacact gaccaattcc caatcgacaa cttcgaattg    960
actcaagcta tgttggaaat catcagaaac ggtggtttgg gtaacggtgg tactaacttc   1020
gacgctaaga tcagaagaaa ctctactgac ttggaagact tgttcatcgc tcacatctct   1080
ggtatggacg ctatggctag agctttgatg aacgctgctg ctatcttgga agaatctgaa   1140
ttgccaaaga tgaagaagga agatacgct tctttcgaca acggtatcgg taaggacttc   1200
gaagacggta agttgacttt ggaacaagct tacgaatacg gtaagaaggt cgaagaacca   1260
aagcaaactt ctggtaagca agaaaagtac gaaactactg tcgctttgta ctgtaagtaa   1320
```

<210> SEQ ID NO 5
<211> LENGTH: 438
<212> TYPE: PRT
<213> ORGANISM: Ruminococcus flavefaciens 17

<400> SEQUENCE: 5

```
Met Glu Phe Phe Ser Asn Ile Gly Lys Ile Gln Tyr Gln Gly Pro Lys
 1               5                  10                  15

Ser Thr Asp Pro Leu Ser Phe Lys Tyr Tyr Asn Pro Glu Glu Val Ile
            20                  25                  30

Asn Gly Lys Thr Met Arg Glu His Leu Lys Phe Ala Leu Ser Trp Trp
        35                  40                  45

His Thr Met Gly Gly Asp Gly Thr Asp Met Phe Gly Cys Gly Thr Thr
    50                  55                  60

Asp Lys Thr Trp Gly Gln Ser Asp Pro Ala Ala Arg Ala Lys Ala Lys
65                  70                  75                  80

Val Asp Ala Ala Phe Glu Ile Met Asp Lys Leu Ser Ile Asp Tyr Tyr
                85                  90                  95

Cys Phe His Asp Arg Asp Leu Ser Pro Glu Tyr Gly Ser Leu Lys Ala
           100                 105                 110

Thr Asn Asp Gln Leu Asp Ile Val Thr Asp Tyr Ile Lys Glu Lys Gln
       115                 120                 125

Gly Asp Lys Phe Lys Cys Leu Trp Gly Thr Ala Lys Cys Phe Asp His
   130                 135                 140

Pro Arg Phe Met His Gly Ala Gly Thr Ser Pro Ser Ala Asp Val Phe
145                 150                 155                 160

Ala Phe Ser Ala Ala Gln Ile Lys Lys Ala Leu Glu Ser Thr Val Lys
               165                 170                 175

Leu Gly Gly Asn Gly Tyr Val Phe Trp Gly Gly Arg Glu Gly Tyr Glu
```

```
                180               185               190
Thr Leu Leu Asn Thr Asn Met Gly Leu Glu Leu Asp Asn Met Ala Arg
            195               200               205
Leu Met Lys Met Ala Val Glu Tyr Gly Arg Ser Ile Gly Phe Lys Gly
        210               215               220
Asp Phe Tyr Ile Glu Pro Lys Pro Lys Glu Pro Thr Lys His Gln Tyr
225               230               235               240
Asp Phe Asp Thr Ala Thr Val Leu Gly Phe Leu Arg Lys Tyr Gly Leu
                245               250               255
Asp Lys Asp Phe Lys Met Asn Ile Glu Ala Asn His Ala Thr Leu Ala
            260               265               270
Gln His Thr Phe Gln His Glu Leu Arg Val Ala Arg Asp Asn Gly Val
        275               280               285
Phe Gly Ser Ile Asp Ala Asn Gln Gly Asp Val Leu Leu Gly Trp Asp
        290               295               300
Thr Asp Gln Phe Pro Thr Asn Ile Tyr Asp Thr Thr Met Cys Met Tyr
305               310               315               320
Glu Val Ile Lys Ala Gly Gly Phe Thr Asn Gly Leu Asn Phe Asp
                325               330               335
Ala Lys Ala Arg Arg Gly Ser Phe Thr Pro Glu Asp Ile Phe Tyr Ser
            340               345               350
Tyr Ile Ala Gly Met Asp Ala Phe Ala Leu Gly Phe Arg Ala Ala Leu
        355               360               365
Lys Leu Ile Glu Asp Gly Arg Ile Asp Lys Phe Val Ala Asp Arg Tyr
    370               375               380
Ala Ser Trp Asn Thr Gly Ile Gly Ala Asp Ile Ile Ala Gly Lys Ala
385               390               395               400
Asp Phe Ala Ser Leu Glu Lys Tyr Ala Leu Glu Lys Gly Glu Val Thr
                405               410               415
Ala Ser Leu Ser Ser Gly Arg Gln Glu Met Leu Glu Ser Ile Val Asn
            420               425               430
Asn Val Leu Phe Ser Leu
        435

<210> SEQ ID NO 6
<211> LENGTH: 1317
<212> TYPE: DNA
<213> ORGANISM: Ruminococcus flavefaciens 17

<400> SEQUENCE: 6
atggaattct tctctaacat cggtaagatc caataccaag gtccaaagtc tactgaccca      60
ttgtctttca gtactacaa cccagaagaa gtcatcaacg gtaagactat gagagaacac     120
ttgaagttcg ctttgtcttg gtggcacact atgggtggtg acggtactga catgttcggt     180
tgtggtacta ctgacaagac ttggggtcaa tctgacccag ctgctagagc taaggctaag     240
gtcgacgctg ctttcgaaat catggacaag ttgtctatcg actactactg tttccacgac     300
agagacttgt ctccagaata cggttctttg aaggctacta cgaccaattt ggacatcgtc     360
actgactaca tcaaggaaaa gcaaggtgac aagttcaagt gtttgtgggg tactgctaag     420
tgtttcgacc acccaagatt catgcacggt gctggtactt ctccatctgc tgacgtcttc     480
gctttctctg ctgctcaaat caagaaggct ttggaatcta ctgtcaagtt gggtggtaac     540
ggttacgtct ctggggtgg tagagaaggt tacgaaactt gttgaacac taacatgggt     600 ttggaattgg acaacatggc tagattgatg aagatggctg tcgaatacgg tagatctatc     660
```

```
ggtttcaagg gtgacttcta catcgaacca aagccaaagg aaccaactaa gcaccaatac    720
gacttcgaca ctgctactgt cttgggtttc ttgagaaagt acggtttgga caaggacttc    780
aagatgaaca tcgaagctaa ccacgctact ttggctcaac acactttcca acacgaattg    840
agagtcgcta gagacaacgg tgtcttcggt tctatcgacg ctaaccaagg tgacgtcttg    900
ttgggttggg acactgacca attcccaact aacatctacg acactactat gtgtatgtac    960
gaagtcatca aggctggtgg tttcactaac ggtggtttga acttcgacgc taaggctaga   1020
agaggttctt tcactccaga agacatcttc tactcttaca tcgctggtat ggacgctttc   1080
gctttgggtt tcagagctgc tttgaagttg atcgaagacg tagaatcga caagttcgtc    1140 gctgacagat acgcttcttg aacactggt atcggtgctg acatcatcgc tggtaaggct    1200
gacttcgctt ctttggaaaa gtacgctttg gaaaagggtg aagtcactgc ttctttgtct   1260
tctggtagac aagaaatgtt ggaatctatc gtcaacaacg tcttgttctc tttgtaa      1317
```

<210> SEQ ID NO 7
<211> LENGTH: 437
<212> TYPE: PRT
<213> ORGANISM: Orpinomyces sp. ukk1

<400> SEQUENCE: 7

```
Met Thr Lys Glu Tyr Phe Pro Thr Ile Gly Lys Ile Arg Phe Glu Gly
1               5                   10                  15

Lys Asp Ser Lys Asn Pro Met Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Asp Gly Ala Asp Gln Phe Gly Val Gly
    50                  55                  60

Thr Lys Ser Phe Pro Trp Asn Glu Gly Thr Asp Pro Ile Ala Ile Ala
65                  70                  75                  80

Lys Gln Lys Val Asp Ala Gly Phe Glu Ile Met Thr Lys Leu Gly Ile
                85                  90                  95

Glu His Tyr Cys Phe His Asp Val Asp Leu Val Ser Glu Gly Asn Ser
            100                 105                 110

Ile Glu Glu Tyr Glu Ser Asn Leu Lys Gln Val Val Ala Tyr Leu Lys
        115                 120                 125

Gln Lys Gln Gln Glu Thr Gly Ile Lys Leu Leu Trp Ser Thr Ala Asn
    130                 135                 140

Val Phe Gly Asn Pro Arg Tyr Met Asn Gly Ala Ser Thr Asn Pro Asp
145                 150                 155                 160

Phe Asp Val Val Ala Arg Ala Ile Val Gln Ile Lys Asn Ala Met Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255
```

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Ile Ser Gly Met Asp Ala Met Ala Arg Ala Leu
        355                 360                 365

Glu Asn Ala Ala Lys Leu Leu Gln Glu Ser Pro Tyr Cys Asn Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Val Thr Ser Gly Lys Gln Glu Leu Tyr Glu Ala Ile
            420                 425                 430

Val Ala Met Tyr Gln
        435

<210> SEQ ID NO 8
<211> LENGTH: 1314
<212> TYPE: DNA
<213> ORGANISM: Orpinomyces sp. ukk1

<400> SEQUENCE: 8
atgactaagg aatacttccc aactatcggt aagatcagat tcgaaggtaa ggactctaag      60
aacccaatgg cttccacta ctacgacgct gaaaaggaag tcatgggtaa gagatgaag      120 gactggttga gattcgctat ggcttggtgg cacactttgt gtgctgacgg tgctgaccaa      180
ttcggtgtcg gtactaagtc tttcccatgg aacgaaggta ctgacccaat cgctatcgct      240
aagcaaaagg tcgacgctgg tttcgaaatc atgactaagt gggtatcga acactactgt      300 ttccacgacg tcgacttggt ctctgaaggt aactctatcg aagaatacga atctaacttg      360
aagcaagtcg tcgcttactt gaagcaaaag caacaagaaa ctggtatcaa gttgttgtgg      420
tctactgcta acgtcttcgg taacccaaga tacatgaacg gtcttctac taacccagac      480 ttcgacgtcg tcgctagagc tatcgtccaa atcaagaacg ctatggacgc tggtatcgaa      540 tgggtgctg aaaactacgt cttctggggt ggtagagaag gttacatgtc tttgttgaac      600
actgaccaaa agagagaaaa ggaacacatg gctactatgt tgactatggc tagagactac      660
gctagatcta agggtttcaa gggtactttc ttgatcgaac aaagccaat ggaaccaact      720 aagcaccaat acgacgtcga cactgaaact gtcatcggtt tcttgagagc tcacaacttg      780
gacaaggact tcaaggtcaa catcgaagtc aaccacgcta ctttggctgg tcacactttc      840
gaacacgaat ggcttgtgc tgtcgacgct ggtatgttgg ttctatcga cgctaacaga      900 ggtgactacc aaaacggttg gacactgac caattcccaa tcgaccaata cgaattggtc      960
caagcttgga tggaaatcat cagaggtggt ggtttcgtca ctggtggtac taacttcgac     1020
gctaagacta agagaaactc tactgacttg gaagacatca tcatcgctca catctctggt     1080

```
atggacgcta tggctagagc tttggaaaac gctgctaagt tgttgcaaga atctccatac    1140
tgtaacatga agaaggaaag atacgcttct ttcgactctg gtatcggtaa ggacttcgaa    1200
gacggtaagt tgactttgga acaagtctac gaatacggta agaagaacgg tgaaccaaag    1260
gtcacttctg gtaagcaaga attgtacgaa gctatcgtcg ctatgtacca ataa          1314
```

<210> SEQ ID NO 9
<211> LENGTH: 437
<212> TYPE: PRT
<213> ORGANISM: Piromyces sp. E2

<400> SEQUENCE: 9

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Phe Val Thr Gly Gly
                325                 330                 335
```

```
        Thr Asn Phe Asp Ala Lys Thr Arg Arg Asn Ser Thr Asp Leu Glu Asp
                        340                 345                 350

Ile Ile Ile Ala His Val Ser Gly Met Asp Ala Met Ala Arg Ala Leu
                        355                 360                 365

Glu Asn Ala Ala Lys Leu Leu Gln Glu Ser Pro Tyr Thr Lys Met Lys
                    370                 375                 380

Lys Glu Arg Tyr Ala Ser Phe Asp Ser Gly Ile Gly Lys Asp Phe Glu
        385                 390                 395                 400

Asp Gly Lys Leu Thr Leu Glu Gln Val Tyr Glu Tyr Gly Lys Lys Asn
                        405                 410                 415

Gly Glu Pro Lys Gln Thr Ser Gly Lys Gln Glu Leu Tyr Glu Ala Ile
                    420                 425                 430

Val Ala Met Tyr Gln
                    435

<210> SEQ ID NO 10
<211> LENGTH: 1314
<212> TYPE: DNA
<213> ORGANISM: Piromyces sp. E2

<400> SEQUENCE: 10
atggctaagg aatacttccc acaaatccaa aagatcaagt tcgaaggtaa ggactctaag      60
aacccattgg ctttccacta ctacgacgct gaaaaggaag tcatgggtaa agagatgaag     120
gactggttga gattcgctat ggcttggtgg cacactttgt gtgctgaagg tgctgaccaa     180
ttcggtggtg gtactaagtc tttcccatgg aacgaaggta ctgacgctat cgaaatcgct     240
aagcaaaagg tcgacgctgg tttcgaaatc atgcaaaagt gggtatccc atactactgt     300 ttccacgacg tcgacttggt ctctgaaggt aactctatcg aagaatacga atctaacttg     360
aaggctgtcg tcgcttactt gaaggaaaag caaaaggaaa ctggtatcaa gttgttgtgg     420
tctactgcta acgtcttcgg tcacaagaga tacatgaacg gtgcttctac taacccagac     480
ttcgacgtcg tcgctagagc tatcgtccaa atcaagaacg ctatcgacgc tggtatcgaa     540
ttgggtgctg aaaactacgt cttctggggt ggtagagaag gttacatgtc tttgttgaac     600
actgaccaaa agagagaaaa ggaacacatg gctactatgt tgactatggc tagagactac     660
gctagatcta agggtttcaa gggtactttc ttgatcgaac caaagccaat ggaaccaact     720
aagcaccaat acgacgtcga cactgaaact gctatcggtt tcttgaaggc tcacaacttg     780
gacaaggact caaggtcaa catcgaagtc aaccacgcta ctttggctgg tcacactttc     840
gaacacgaat tggcttgtgc tgtcgacgct ggtatgttgg ttctatcga cgctaacaga     900 ggtgactacc aaaacggttg gacactgac caattcccaa tcgaccaata cgaattggtc     960
caagcttgga tggaaatcat cagaggtggt ggtttcgtca ctggtggtac taacttcgac    1020
gctaagacta agagaaactc tactgacttg aagacatca tcatcgctca cgtctctggt    1080
atggacgcta tggctagagc tttggaaaac gctgctaagt tgttgcaaga atctccatac    1140
actaagatga agaaggaaag atacgcttct ttcgactctg gtatcggtaa ggacttcgaa    1200
gacggtaagt tgactttgga acaagtctac gaatacggta gaagaacgg tgaaccaaag    1260 caaacttctg gtaagcaaga attgtacgaa gctatcgtcg ctatgtacca ataa          1314

<210> SEQ ID NO 11
<211> LENGTH: 438
<212> TYPE: PRT
<213> ORGANISM: Clostridium phytofermentans ISDg
```

<400> SEQUENCE: 11

```
Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Ala Asp Pro Phe Gly Val Thr Thr
    50                  55                  60

Met Asp Arg Thr Tyr Gly Asn Ile Thr Asp Pro Met Glu Leu Ala Lys
65              70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
            115                 120                 125

Lys Met Asp Gln Thr Gly Ile Lys Leu Leu Trp Gly Thr Ala Asn Asn
130             135                 140

Phe Ser His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Lys Gly Tyr Val Phe Trp Gly Gly Arg Glu
            180                 185                 190

Gly Tyr Glu Thr Leu Leu Asn Thr Asp Leu Gly Leu Glu Leu Asp Asn
            195                 200                 205

Met Ala Arg Leu Met Lys Met Ala Val Glu Tyr Gly Arg Ala Asn Gly
210                 215                 220

Phe Asp Gly Asp Phe Tyr Ile Glu Pro Lys Pro Lys Glu Pro Thr Lys
225                 230                 235                 240

His Gln Tyr Asp Phe Asp Thr Ala Thr Val Leu Ala Phe Leu Arg Lys
                245                 250                 255

Tyr Gly Leu Glu Lys Asp Phe Lys Met Asn Ile Glu Ala Asn His Ala
            260                 265                 270

Thr Leu Ala Gly His Thr Phe Glu His Glu Leu Ala Met Ala Arg Val
            275                 280                 285

Asn Gly Ala Phe Gly Ser Val Asp Ala Asn Gln Gly Asp Pro Asn Leu
            290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Gly Phe Thr Asn Gly Gly Leu
                325                 330                 335

Asn Phe Asp Ala Lys Val Arg Arg Gly Ser Phe Glu Phe Asp Asp Ile
            340                 345                 350

Ala Tyr Gly Tyr Ile Ala Gly Met Asp Thr Phe Ala Leu Gly Leu Ile
            355                 360                 365

Lys Ala Ala Glu Ile Ile Asp Asp Gly Arg Ile Ala Lys Phe Val Asp
            370                 375                 380

Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Ser
```

```
                    405                 410                 415
Glu Pro Val Met Gln Ser Gly Arg Gln Glu Val Leu Glu Thr Ile Val
            420                 425                 430

Asn Asn Ile Leu Phe Arg
        435

<210> SEQ ID NO 12
<211> LENGTH: 1317
<212> TYPE: DNA
<213> ORGANISM: Clostridium phytofermentans ISDg

<400> SEQUENCE: 12
atgaagaact acttcccaaa cgtcccagaa gtcaagtacg aaggtccaaa ctctactaac        60
ccattcgctt tcaagtacta cgacgctaac aaggtcgtcg ctggtaagac tatgaaggaa       120
cactgtagat tcgctttgtc ttggtggcac actttgtgtg ctggtggtgc tgacccattc       180
ggtgtcacta ctatggacag aacttacggt aacatcactg acccaatgga attggctaag       240
gctaaggtcg acgctggttt cgaattgatg actaagttgg gtatcgaatt cttctgtttc       300
cacgacgctg acatcgctcc agaaggtgac actttcgaag aatctaagaa gaacttgttc       360
gaaatcgtcg actacatcaa ggaaagatg accaaactg gtatcaagtt gttgtggggt        420
actgctaaca acttctctca cccaagattc atgcacggtg cttctacttc ttgtaacgct       480
gacgtcttcg cttacgctgc tgctaagatc aagaacgctt ggacgctac tatcaagttg        540 ggtggtaagg gttacgtctt ctggggtggt agagaaggtt acgaaacttt gttgaacact       600
gacttgggtt tggaattgga caacatggct agattgatga agatggctgt cgaatacggt       660
agagctaacg gtttcgacgg tgacttctac atcgaaccaa agccaaagga accaactaag       720
caccaatacg acttcgacac tgctactgtc ttggctttct tgagaaagta cggtttggaa       780
aaggacttca agatgaacat cgaagctaac cacgctactt tggctggtca cactttcgaa       840
cacgaattgg ctatggctag agtcaacggt gctttcggtt ctgtcgacgc taaccaaggt       900
gacccaaact tgggttggga cactgaccaa ttcccaactg acgtccactc tgctactttg       960
gctatgttgg aagtcttgaa ggctggtggt ttcactaacg gtggtttgaa cttcgacgct      1020
aaggtcagaa gaggttcttt cgaattcgac gacatcgctt acggttacat cgctggtatg      1080
gacactttcg ctttgggttt gatcaaggct gctgaaatca tcgacgacgg tagaatcgct      1140
aagttcgtcg acgacagata cgcttcttac aagactggta tcggtaaggc tatcgtcgac      1200
ggtactactt ctttggaaga attgaacaa tacgtcttga ctcactctga accagtcatg      1260
caatctggta gacaagaagt cttggaaact atcgtcaaca acatcttgtt cagataa         1317

<210> SEQ ID NO 13
<211> LENGTH: 439
<212> TYPE: PRT
<213> ORGANISM: Clostridium cellulolyticum H10

<400> SEQUENCE: 13

Met Ser Glu Val Phe Ser Gly Ile Ser Asn Ile Lys Phe Glu Gly Ser
1               5                   10                  15

Gly Ser Asp Asn Pro Leu Ala Phe Lys Tyr Tyr Asp Pro Lys Ala Val
            20                  25                  30

Ile Gly Gly Lys Thr Met Glu Glu His Leu Arg Phe Ala Val Ala Tyr
        35                  40                  45

Trp His Thr Phe Ala Ala Pro Gly Ala Asp Met Phe Gly Ala Gly Ser
    50                  55                  60
```

Tyr Val Arg Pro Trp Asn Thr Met Ser Asp Pro Leu Glu Ile Ala Lys
65                  70                  75                  80

Tyr Lys Val Glu Ala Asn Phe Glu Phe Ile Glu Lys Leu Gly Ala Pro
            85                  90                  95

Phe Phe Ala Phe His Asp Arg Asp Ile Ala Pro Glu Gly Asp Thr Leu
        100                 105                 110

Ala Glu Thr Asn Lys Asn Leu Asp Thr Ile Val Ser Val Ile Lys Asp
        115                 120                 125

Arg Met Lys Ser Ser Pro Val Lys Leu Leu Trp Gly Thr Thr Asn Ala
        130                 135                 140

Phe Gly Asn Pro Arg Phe Met His Gly Ala Ser Thr Ser Pro Asn Ala
145                 150                 155                 160

Asp Ile Phe Ala Tyr Ala Ala Ala Gln Val Lys Lys Ala Met Glu Ile
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Met Lys Leu Glu Leu Asp Asn
            195                 200                 205

Leu Ala Arg Phe Leu Lys Met Ala Val Asp Tyr Ala Lys Glu Ile Gly
210                 215                 220

Phe Asp Gly Gln Phe Leu Ile Glu Pro Lys Pro Lys Glu Pro Thr Lys
225                 230                 235                 240

His Gln Tyr Asp Phe Asp Thr Ala Thr Val Ile Gly Phe Leu Lys Thr
                245                 250                 255

Tyr Gly Leu Asp Pro Tyr Phe Lys Met Asn Ile Glu Ala Asn His Ala
            260                 265                 270

Thr Leu Ala Gly His Thr Phe Gln His Glu Leu Ala Met Cys Arg Ile
            275                 280                 285

Asn Asp Met Leu Gly Ser Ile Asp Ala Asn Gln Gly Asp Val Met Leu
290                 295                 300

Gly Trp Asp Thr Asp Gln Phe Pro Thr Asn Leu Tyr Asp Ala Thr Leu
305                 310                 315                 320

Ala Met Val Glu Val Leu Lys Ala Gly Leu Lys Lys Gly Gly Leu
                325                 330                 335

Asn Phe Asp Ser Lys Val Arg Arg Gly Ser Phe Glu Pro Ser Asp Leu
            340                 345                 350

Phe Tyr Gly His Ile Ala Gly Met Asp Thr Phe Ala Lys Gly Leu Ile
            355                 360                 365

Ile Ala Asn Lys Ile Val Glu Asp Gly Lys Phe Asp Ala Phe Val Ala
        370                 375                 380

Asp Arg Tyr Ser Ser Tyr Thr Asn Gly Ile Gly Lys Asp Ile Val Glu
385                 390                 395                 400

Gly Lys Val Gly Phe Lys Glu Leu Glu Gln Tyr Ala Leu Thr Ala Lys
            405                 410                 415

Ile Gln Asn Lys Ser Gly Arg Gln Glu Met Leu Glu Ala Leu Leu Asn
            420                 425                 430

Gln Tyr Ile Leu Glu Thr Lys
            435

<210> SEQ ID NO 14
<211> LENGTH: 1320
<212> TYPE: DNA
<213> ORGANISM: Clostridium cellulolyticum H10

<400> SEQUENCE: 14

```
atgtctgaag tcttctctgg tatctctaac atcaagttcg aaggttctgg ttctgacaac    60
ccattggctt tcaagtacta cgacccaaag gctgtcatcg gtggtaagac tatggaagaa   120
cacttgagat cgctgtcgc ttactggcac actttcgctg ctccaggtgc tgacatgttc   180
ggtgctggtt cttacgtcag accatggaac actatgtctg acccattgga aatcgctaag   240
tacaaggtcg aagctaactt cgaattcatc gaaaagttgg gtgctccatt cttcgctttc   300
cacgacagag acatcgctcc agaaggtgac actttggctg aaactaacaa gaacttggac   360
actatcgtct ctgtcatcaa ggacagaatg aagtcttctc cagtcaagtt gttgtggggt   420
actactaacg ctttcggtaa cccaagattc atgcacggtg cttctacttc tccaaacgct   480
gacatcttcg cttacgctgc tgctcaagtc aagaaggcta tggaaatcac taaggaattg   540
ggtggtgaaa actacgtctt ctggggtggt agagaaggtt acgaaacttt gttgaacact   600
gacatgaagt tggaattgga caacttggct agattcttga gatggctgt cgactacgct   660
aaggaaatcg gttcgacgg tcaattcttg atcgaaccaa agccaaagga accaactaag   720
caccaatacg acttcgacac tgctactgtc atcggttctct gaagactta cggtttggac   780
ccatacttca agatgaacat cgaagctaac acgctactgt ggctggtca cactttccaa   840
cacgaattgg ctatgtgtag aatcaacgac atgttgggtt ctatcgacgc taaccaaggt   900
gacgtcatgt tgggttggga cactgaccaa ttcccaacta acttgtacga cgctactttg   960
gctatggtcg aagtcttgaa ggctggtggt ttgaagaagg gtggtttgaa cttcgactct  1020
aaggtcagaa gaggttcttt cgaaccatct gacttgttct acggtcacat cgctggtatg  1080
gacactttcg ctaagggttt tgatcatcgct aacaagatcg tcgaagacgg taagttcgac  1140
gctttcgtcg ctgacagata ctcttcttac actaacggta tcggtaagga catcgtcgaa  1200
ggtaaggtcg gtttcaagga attggaacaa tacgctttga ctgctaagat ccaaaacaag  1260
tctggtagac aagaaatgtt ggaagctttg ttgaaccaat acatcttgga aactaagtaa  1320
```

<210> SEQ ID NO 15
<211> LENGTH: 388
<212> TYPE: PRT
<213> ORGANISM: Streptomyces rubiginosus

<400> SEQUENCE: 15

```
Met Asn Tyr Gln Pro Thr Pro Glu Asp Arg Phe Thr Phe Gly Leu Trp
  1               5                  10                  15

Thr Val Gly Trp Gln Gly Arg Asp Pro Phe Gly Asp Ala Thr Arg Arg
             20                  25                  30

Ala Leu Asp Pro Val Glu Ser Val Arg Arg Leu Ala Glu Leu Gly Ala
         35                  40                  45

His Gly Val Thr Phe His Asp Asp Leu Ile Pro Phe Gly Ser Ser
     50                  55                  60

Asp Ser Glu Arg Glu Glu His Val Lys Arg Phe Arg Gln Ala Leu Asp
 65                  70                  75                  80

Asp Thr Gly Met Lys Val Pro Met Ala Thr Thr Asn Leu Phe Thr His
                 85                  90                  95

Pro Val Phe Lys Asp Gly Phe Thr Ala Asn Asp Arg Asp Val Arg
                100                 105                 110

Arg Tyr Ala Leu Arg Lys Thr Ile Arg Asn Ile Asp Leu Ala Val Glu
            115                 120                 125

Leu Gly Ala Glu Thr Tyr Val Ala Trp Gly Gly Arg Glu Gly Ala Glu
```

Ser Gly Gly Ala Lys Asp Val Arg Asp Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Asn Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Tyr Ser Gly Pro Arg His Phe Asp Phe
        275                 280                 285

Lys Pro Pro Arg Thr Glu Asp Phe Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ser Arg Leu Asp
                325                 330                 335

Glu Leu Ala Arg Pro Thr Ala Ala Asp Gly Leu Gln Ala Leu Leu Asp
            340                 345                 350

Asp Arg Ser Ala Phe Glu Glu Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg Gly
385

<210> SEQ ID NO 16
<211> LENGTH: 1167
<212> TYPE: DNA
<213> ORGANISM: Streptomyces rubiginosus

<400> SEQUENCE: 16
atgaactacc aaccaactcc agaagacaga ttcactttcg gtttgtggac tgtcggttgg     60
caaggtagag acccattcgg tgacgctact agaagagctt tggacccagt cgaatctgtc    120
agaagattgg ctgaattggg tgctcacggt gtcactttcc acgacgacga cttgatccca    180
ttcggttctt ctgactctga agagaagaa cacgtcaaga gattcagaca agctttggac    240
gacactggta tgaaggtccc aatggctact actaacttgt tcactcaccc agtcttcaag    300
gacggtggtt tcactgctaa cgacagagac gtcagaagat acgctttgag aaagactatc    360
agaaacatcg acttggctgt cgaattgggt gctgaaactt acgtcgcttg ggtggtagaa    420
gaaggtgctg aatctggtgg tgctaaggac gtcagagacg ctttggacag aatgaaggaa    480
gctttcgact tgttgggtga atacgtcact tctcaaggtt acgacatcag attcgctatc    540
gaaccaaagc caaacgaacc aagaggtgac atcttgttgc caactgtcgg tcacgctttg    600
gctttcatcg aaagattgga aagaccagaa ttgtacggtg tcaacccaga agtcggtcac    660

```
gaacaaatgg ctggtttgaa cttcccacac ggtatcgctc aagctttgtg ggctggtaag    720
ttgttccaca tcgacttgaa cggtcaaaac ggtatcaagt acgaccaaga cttgagattc    780
ggtgctggtg acttgagagc tgctttctgg ttggtcgact tgttggaatc tgctggttac    840
tctggtccaa gacacttcga cttcaagcca ccaagaactg aagacttcga cggtgtctgg    900
gcttctgctg ctggttgtat gagaaactac ttgatcttga aggaaagagc tgctgctttc    960
agagctgacc cagaagtcca agaagctttg agagcttcta gattggacga attggctaga   1020
ccaactgctg ctgacggttt gcaagctttg ttggacgaca gatctgcttt cgaagaattc   1080
gacgtcgacg ctgctgctgc tagaggtatg gctttcgaaa gattggacca attggctatg   1140
gaccacttgt tgggtgctag aggttaa                                       1167
```

<210> SEQ ID NO 17
<211> LENGTH: 46
<212> TYPE: DNA
<213> ORGANISM: Artificial Sequence
<220> FEATURE:
<223> OTHER INFORMATION: synthetic IR2_dHO_F1

<400> SEQUENCE: 17

```
cagcaatcaa ttccatctat actttaaaca gctgaagctt cgtacg                    46
```

<210> SEQ ID NO 18
<211> LENGTH: 49
<212> TYPE: DNA
<213> ORGANISM: Artificial Sequence
<220> FEATURE:
<223> OTHER INFORMATION: synthetic IR2_dHO_R1

<400> SEQUENCE: 18

```
acaactttt taaactaata tacacattgc ataggccact agtggatct                  49
```

<210> SEQ ID NO 19
<211> LENGTH: 48
<212> TYPE: DNA
<213> ORGANISM: Artificial Sequence
<220> FEATURE:
<223> OTHER INFORMATION: synthetic TS_KO_HO_F2

<400> SEQUENCE: 19

```
tctaaatcca tatccttata agcagcaatc aattccatct atacttta                  48
```

<210> SEQ ID NO 20
<211> LENGTH: 49
<212> TYPE: DNA
<213> ORGANISM: Artificial Sequence
<220> FEATURE:
<223> OTHER INFORMATION: synthetic TS_KO_HO_R2

<400> SEQUENCE: 20

```
ttaaatttta cttttattac atacaacttt tttaaactaa tatacacat                 49
```

<210> SEQ ID NO 21
<211> LENGTH: 23
<212> TYPE: DNA
<213> ORGANISM: Artificial Sequence
<220> FEATURE:
<223> OTHER INFORMATION: synthetic TS_IR-2_dHO_checkF2

<400> SEQUENCE: 21

```
attaggtgtg aaaccacgaa aaa                                             23
```

```
<210> SEQ ID NO 22
<211> LENGTH: 23
<212> TYPE: DNA
<213> ORGANISM: Artificial Sequence
<220> FEATURE:
<223> OTHER INFORMATION: synthetic TS_IR-2_dHO_checkR2

<400> SEQUENCE: 22
aggaaagttg atcaagaccc aat                                           23

<210> SEQ ID NO 23
<211> LENGTH: 44
<212> TYPE: DNA
<213> ORGANISM: Artificial Sequence
<220> FEATURE:
<223> OTHER INFORMATION: synthetic KO13_IR-2_GRE3_KO_F1

<400> SEQUENCE: 23
cttcaagacg attgggaaaa tactcagctg aagcttcgta cgct                    44

<210> SEQ ID NO 24
<211> LENGTH: 48
<212> TYPE: DNA
<213> ORGANISM: Artificial Sequence
<220> FEATURE:
<223> OTHER INFORMATION: synthetic KO15_IR-2_GRE3_KO_R1

<400> SEQUENCE: 24
ctccgttaaa gtgaactttt tttcgagcat aggccactag tggatctg                48

<210> SEQ ID NO 25
<211> LENGTH: 49
<212> TYPE: DNA
<213> ORGANISM: Artificial Sequence
<220> FEATURE:
<223> OTHER INFORMATION: synthetic KO14_IR-2_GRE3_KO_F2

<400> SEQUENCE: 25
gaagcaaata gttgtcagtg caatccttca agacgattgg gaaaatact               49

<210> SEQ ID NO 26
<211> LENGTH: 51
<212> TYPE: DNA
<213> ORGANISM: Artificial Sequence
<220> FEATURE:
<223> OTHER INFORMATION: synthetic KO16_IR-2_GRE3_KO_R2

<400> SEQUENCE: 26
gtgcagaaat atccttcaat tcttgctccg ttaaagtgaa cttttttttcg a           51

<210> SEQ ID NO 27
<211> LENGTH: 24
<212> TYPE: DNA
<213> ORGANISM: Artificial Sequence
<220> FEATURE:
<223> OTHER INFORMATION: synthetic PK47_Check_GRE3_F

<400> SEQUENCE: 27
acatgcggaa gaattttatg gaaa                                          24

<210> SEQ ID NO 28
<211> LENGTH: 24
<212> TYPE: DNA
<213> ORGANISM: Artificial Sequence
<220> FEATURE:
<223> OTHER INFORMATION: synthetic PK48_Check_GRE3_R
```

<400> SEQUENCE: 28
aaccaggtcc atggatcatt aaat                                              24

<210> SEQ ID NO 29
<211> LENGTH: 23
<212> TYPE: DNA
<213> ORGANISM: Artificial Sequence
<220> FEATURE:
<223> OTHER INFORMATION: synthetic BcXIopt_F1

<400> SEQUENCE: 29
atgtcttact tcgaacacat ccc                                               23

<210> SEQ ID NO 30
<211> LENGTH: 31
<212> TYPE: DNA
<213> ORGANISM: Artificial Sequence
<220> FEATURE:
<223> OTHER INFORMATION: synthetic BcXIopt_R1

<400> SEQUENCE: 30
gcgcctcgag acgcaaaccg tagatagctt g                                      31

<210> SEQ ID NO 31
<211> LENGTH: 21
<212> TYPE: DNA
<213> ORGANISM: Artificial Sequence
<220> FEATURE:
<223> OTHER INFORMATION: synthetic PrXIopt_F1

<400> SEQUENCE: 31
atggctaagg aatacttccc a                                                 21

<210> SEQ ID NO 32
<211> LENGTH: 35
<212> TYPE: DNA
<213> ORGANISM: Artificial Sequence
<220> FEATURE:
<223> OTHER INFORMATION: synthetic PrXIopt_R1

<400> SEQUENCE: 32
gcctcgagct tacagtacaa agcgacagta gtttc                                  35

<210> SEQ ID NO 33
<211> LENGTH: 23
<212> TYPE: DNA
<213> ORGANISM: Artificial Sequence
<220> FEATURE:
<223> OTHER INFORMATION: synthetic RfXIopt_F1

<400> SEQUENCE: 33
atggaattct tctctaacat cgg                                               23

<210> SEQ ID NO 34
<211> LENGTH: 34
<212> TYPE: DNA
<213> ORGANISM: Artificial Sequence
<220> FEATURE:
<223> OTHER INFORMATION: synthetic RfXIopt_R1

<400> SEQUENCE: 34
gcgcctcgag caaagagaac aagacgttgt tgac                                   34

<210> SEQ ID NO 35

<211> LENGTH: 26
<212> TYPE: DNA
<213> ORGANISM: Artificial Sequence
<220> FEATURE:
<223> OTHER INFORMATION: synthetic 04_OspXIopt_F1

<400> SEQUENCE: 35
atgactaagg aatacttccc aactat                                          26

<210> SEQ ID NO 36
<211> LENGTH: 33
<212> TYPE: DNA
<213> ORGANISM: Artificial Sequence
<220> FEATURE:
<223> OTHER INFORMATION: synthetic 04_OspXIopt_R1

<400> SEQUENCE: 36
gcgcctcgag ttggtacata gcgacgatag ctt                                  33

<210> SEQ ID NO 37
<211> LENGTH: 22
<212> TYPE: DNA
<213> ORGANISM: Artificial Sequence
<220> FEATURE:
<223> OTHER INFORMATION: synthetic 05_PspXIopt_F1

<400> SEQUENCE: 37
atggctaagg aatacttccc ac                                              22

<210> SEQ ID NO 38
<211> LENGTH: 33
<212> TYPE: DNA
<213> ORGANISM: Artificial Sequence
<220> FEATURE:
<223> OTHER INFORMATION: synthetic 05_PspXIopt_R1

<400> SEQUENCE: 38
gcgcctcgag ttggtacata gcgacgatag ctt                                  33

<210> SEQ ID NO 39
<211> LENGTH: 25
<212> TYPE: DNA
<213> ORGANISM: Artificial Sequence
<220> FEATURE:
<223> OTHER INFORMATION: synthetic 06_CpXIopt_F1

<400> SEQUENCE: 39
atgaagaact acttcccaaa cgtcc                                           25

<210> SEQ ID NO 40
<211> LENGTH: 33
<212> TYPE: DNA
<213> ORGANISM: Artificial Sequence
<220> FEATURE:
<223> OTHER INFORMATION: synthetic 06_CpXIopt_R1

<400> SEQUENCE: 40
gcgcctcgag tctgaacaag atgttgttga cga                                  33

<210> SEQ ID NO 41
<211> LENGTH: 26
<212> TYPE: DNA
<213> ORGANISM: Artificial Sequence
<220> FEATURE:
<223> OTHER INFORMATION: synthetic 07_CcXIopt_F1

<400> SEQUENCE: 41

-continued

```
atgtctgaag tcttctctgg tatctc                                          26

<210> SEQ ID NO 42
<211> LENGTH: 35
<212> TYPE: DNA
<213> ORGANISM: Artificial Sequence
<220> FEATURE:
<223> OTHER INFORMATION: synthetic 07_CcXIopt_R1

<400> SEQUENCE: 42
gcgcctcgag cttagtttcc aagatgtatt ggttc                                35

<210> SEQ ID NO 43
<211> LENGTH: 23
<212> TYPE: DNA
<213> ORGANISM: Artificial Sequence
<220> FEATURE:
<223> OTHER INFORMATION: synthetic 08_SrXIopt_F1

<400> SEQUENCE: 43
atgaactacc aaccaactcc aga                                             23

<210> SEQ ID NO 44
<211> LENGTH: 31
<212> TYPE: DNA
<213> ORGANISM: Artificial Sequence
<220> FEATURE:
<223> OTHER INFORMATION: synthetic 08_SrXIopt_R1

<400> SEQUENCE: 44
gcgcctcgag acctctagca cccaacaagt g                                    31

<210> SEQ ID NO 45
<211> LENGTH: 35
<212> TYPE: DNA
<213> ORGANISM: Artificial Sequence
<220> FEATURE:
<223> OTHER INFORMATION: synthetic TCYC1-PPGK1 F

<400> SEQUENCE: 45
tttgcggccg gtaccactag tactgtaatt gcttt                                35

<210> SEQ ID NO 46
<211> LENGTH: 35
<212> TYPE: DNA
<213> ORGANISM: Artificial Sequence
<220> FEATURE:
<223> OTHER INFORMATION: synthetic pUG35-TCYC1R

<400> SEQUENCE: 46
tcgagaaccc ttaatggtac cggccgcaaa ttaaa                                35

<210> SEQ ID NO 47
<211> LENGTH: 34
<212> TYPE: DNA
<213> ORGANISM: Artificial Sequence
<220> FEATURE:
<223> OTHER INFORMATION: synthetic oSS62 XI-F_HSP12s

<400> SEQUENCE: 47
actcaaaaca aaaaaaacta aatacaacac ccat                                 34

<210> SEQ ID NO 48
<211> LENGTH: 24
<212> TYPE: DNA
```

```
<213> ORGANISM: Artificial Sequence
<220> FEATURE:
<223> OTHER INFORMATION: synthetic oSS74 XI-Rc

<400> SEQUENCE: 48
ttgggaattg gtcagtgtcc caac                                             24

<210> SEQ ID NO 49
<211> LENGTH: 34
<212> TYPE: DNA
<213> ORGANISM: Artificial Sequence
<220> FEATURE:
<223> OTHER INFORMATION: synthetic oSS63 XI-R_HSP12as

<400> SEQUENCE: 49 agttttttt gttttgagtt gtttgtttga gatt                                   34

<210> SEQ ID NO 50
<211> LENGTH: 23
<212> TYPE: DNA
<213> ORGANISM: Artificial Sequence
<220> FEATURE:
<223> OTHER INFORMATION: synthetic oSS83 06_CpXI-Fc

<400> SEQUENCE: 50
ctgaccaatt cccaactgac gtc                                              23

<210> SEQ ID NO 51
<211> LENGTH: 18
<212> TYPE: DNA
<213> ORGANISM: Artificial Sequence
<220> FEATURE:
<223> OTHER INFORMATION: synthetic 06_CpXIopt_Seq_F1

<400> SEQUENCE: 51
ttggctttct tgagaaag                                                    18

<210> SEQ ID NO 52
<211> LENGTH: 18
<212> TYPE: DNA
<213> ORGANISM: Artificial Sequence
<220> FEATURE:
<223> OTHER INFORMATION: synthetic 06_CpXIopt_Seq_R1

<400> SEQUENCE: 52
tagcgtggtt agcttcga                                                    18

<210> SEQ ID NO 53
<211> LENGTH: 27
<212> TYPE: DNA
<213> ORGANISM: Artificial Sequence
<220> FEATURE:
<223> OTHER INFORMATION: synthetic oSS106 06_CpXI_V162A

<400> SEQUENCE: 53
tgtaacgctg acgctttcgc ttacgct                                          27

<210> SEQ ID NO 54
<211> LENGTH: 30
<212> TYPE: DNA
<213> ORGANISM: Artificial Sequence
<220> FEATURE:
<223> OTHER INFORMATION: synthetic oSS107 06_CpXI_V162Aas

<400> SEQUENCE: 54
agaagtagaa gcaccgtgca tgaatcttgg                                       30
```

<210> SEQ ID NO 55
<211> LENGTH: 27
<212> TYPE: DNA
<213> ORGANISM: Artificial Sequence
<220> FEATURE:
<223> OTHER INFORMATION: synthetic oSS108 06_CpXI_N303T

<400> SEQUENCE: 55
caaggtgacc caactttggg ttgggac                                        27

<210> SEQ ID NO 56
<211> LENGTH: 27
<212> TYPE: DNA
<213> ORGANISM: Artificial Sequence
<220> FEATURE:
<223> OTHER INFORMATION: synthetic oSS109 06_CpXI_N303Tas

<400> SEQUENCE: 56
gttagcgtcg acagaaccga aagcacc                                        27

<210> SEQ ID NO 57
<211> LENGTH: 30
<212> TYPE: DNA
<213> ORGANISM: Artificial Sequence
<220> FEATURE:
<223> OTHER INFORMATION: synthetic RfXI(Opt)(G179A)

<400> SEQUENCE: 57
gtcaagttgg gtgctaacgg ttacgtcttc                                     30

<210> SEQ ID NO 58
<211> LENGTH: 25
<212> TYPE: DNA
<213> ORGANISM: Artificial Sequence
<220> FEATURE:
<223> OTHER INFORMATION: synthetic RfXI(Opt)(G179A)as

<400> SEQUENCE: 58
agtagattcc aaagccttct tgatt                                          25

<210> SEQ ID NO 59
<211> LENGTH: 30
<212> TYPE: DNA
<213> ORGANISM: Artificial Sequence
<220> FEATURE:
<223> OTHER INFORMATION: synthetic PspXI(Opt)(E15D)

<400> SEQUENCE: 59
aagatcaagt tcgacggtaa ggactctaag                                     30

<210> SEQ ID NO 60
<211> LENGTH: 25
<212> TYPE: DNA
<213> ORGANISM: Artificial Sequence
<220> FEATURE:
<223> OTHER INFORMATION: synthetic PspXI(Opt)(E15D)as

<400> SEQUENCE: 60
ttggatttgt gggaagtatt cctta                                          25

<210> SEQ ID NO 61
<211> LENGTH: 30
<212> TYPE: DNA
<213> ORGANISM: Artificial Sequence
<220> FEATURE:

<223> OTHER INFORMATION: synthetic PspXI(Opt)(T142S)

<400> SEQUENCE: 61
gttgttgtgg tcttctgcta acgtcttcgg 30

<210> SEQ ID NO 62
<211> LENGTH: 25
<212> TYPE: DNA
<213> ORGANISM: Artificial Sequence
<220> FEATURE:
<223> OTHER INFORMATION: synthetic PspXI(Opt)(T142S)as

<400> SEQUENCE: 62
ttgataccag tttccttttg ctttt 25

<210> SEQ ID NO 63
<211> LENGTH: 1320
<212> TYPE: DNA
<213> ORGANISM: artificial sequence
<220> FEATURE:
<223> OTHER INFORMATION: synthetic CpXIopt2 having a mutation of T63L

<400> SEQUENCE: 63
atgaagaatt actttccaaa tgttcctgaa gttaaatacg aaggtcctaa ctctacaaat       60
ccttttgctt ttaaatacta cgatgctaat aaggttgttg ctggtaaaac tatgaaggaa     120
cattgtcgtt ttgctttatc ttggtggcat acactttgcg caggtggagc tgatcctttt     180
ggtgttctga caatggatag aacttacgga acattacag atccaatgga attggcaaaa      240
gctaaggttg atgctggttt tgaacttatg actaagttgg gaattgaatt tttctgtttt     300
catgatgcag atattgctcc tgaaggagat acatttgaag aatctaagaa aaatcttttt     360
gaaattgttg attacattaa agaaagatg gatcaaactg gtattaaaact tctttgggga    420 acagctaaca acttttcaca tccacgtttt atgcatggtg cttctacttc atgcaatgct     480 gatgttttg catatgctgc agctaaaatt aagaacgcat ggatgctac tattaaactt       540 ggtggaaagg gttacgtttt ctggggtgga cgtgaaggat acgaaacttt gcttaacaca    600
gatcttggtt tggaattaga taacatggct agacttatga gatggcagt tgaatatgga     660 cgagctaacg gttttgatgg agattttac attgaaccta aaccaaagga acctactaag      720
catcaatacg attttgatac tgctacagtt ttagcatttc ttcgaaagta cggtttggaa    780 aaggattta agatgaacat tgaagcaaac catgctactc ttgcaggaca tacatttgaa     840
catgaattgg caatggctag agttaatggt gcatttggat ctgttgatgc taatcaagga    900
gatcctaact aggatggga tactgatcaa tttccaacag atgttcattc agctactttg      960
gcaatgttag aagttcttaa agctggtggt tttactaatg gtggacttaa ctttgatgct    1020
aaggttcgta gaggttcttt tgaatttgat gatattgctt acggttacat tgcaggaatg    1080
gatacttttg ctcttggttt gattaaagca gctgaaatta ttgatgatgg acgaattgct    1140
aagtttgttg atgatcgtta tgcttcatac aaaactggta ttggaaaggc tattgttgat    1200
ggtactacat cttttggaaga attagaacaa tacgttctta ctcattcaga acctgttatg    1260
caatcaggtc gtcaagaagt tttggaaaact attgttaata acattctttt tagactcgag    1320

<210> SEQ ID NO 64
<211> LENGTH: 1320
<212> TYPE: DNA
<213> ORGANISM: artificial sequence
<220> FEATURE:
<223> OTHER INFORMATION: synthetic CpXIopt2 having a mutation of T63G

<400> SEQUENCE: 64

```
atgaagaatt actttccaaa tgttcctgaa gttaaatacg aaggtcctaa ctctacaaat    60
cctttttgctt ttaaatacta cgatgctaat aaggttgttg ctggtaaaac tatgaaggaa   120
cattgtcgtt ttgctttatc ttggtggcat acactttgcg caggtggagc tgatcctttt   180
ggtgttggta caatggatag aacttacgga acattacag atccaatgga attggcaaaa    240
gctaaggttg atgctggttt tgaacttatg actaagttgg gaattgaatt tttctgtttt   300
catgatgcag atattgctcc tgaaggagat acatttgaag aatctaagaa aaatcttttt   360
gaaattgttg attacattaa agaaagatg gatcaaactg gtattaaaact tctttgggga   420
acagctaaca acttttcaca tccacgtttt atgcatggtg cttctacttc atgcaatgct   480
gatgtttttg catatgctgc agctaaaatt aagaacgcat ggatgctac tattaaactt    540
ggtggaaagg gttacgtttt ctggggtgga cgtgaaggat acgaaacttt gcttaacaca   600
gatcttggtt tggaattaga taacatggct agacttatga agatggcagt tgaatatgga   660
cgagctaacg ttttgatgg agattttttac attgaaccta accaaagga acctactaag    720
catcaatacg atttgatac tgctacagtt ttagcatttc ttcgaaagta cggtttggaa    780
aaggattttta agatgaacat tgaagcaaac catgctactc ttgcaggaca tacatttgaa   840
catgaattgg caatggctag agttaatggt gcatttggat ctgttgatgc taatcaagga   900
gatcctaact taggatggga tactgatcaa tttccaacag atgttcattc agctactttg   960
gcaatgttag aagttcttaa agctggtggt tttactaatg gtggacttaa ctttgatgct  1020
aaggttcgta gaggttcttt tgaatttgat gatattgctt acggttacat tgcaggaatg  1080
gatacttttg ctcttggttt gattaaagca gctgaaatta ttgatgatgg acgaattgct  1140
aagtttgttg atgatcgtta tgcttcatac aaaactggta ttggaaaggc tattgttgat  1200
ggtactacat ctttggaaga attagaacaa tacgttctta ctcattcaga acctgttatg  1260
caatcaggtc gtcaagaagt tttggaaact attgttaata acattctttt tagactcgag  1320
```

<210> SEQ ID NO 65
<211> LENGTH: 1320
<212> TYPE: DNA
<213> ORGANISM: artificial sequence
<220> FEATURE:
<223> OTHER INFORMATION: synthetic CpXIopt2 having a mutation of T63H

<400> SEQUENCE: 65

```
atgaagaatt actttccaaa tgttcctgaa gttaaatacg aaggtcctaa ctctacaaat    60
cctttttgctt ttaaatacta cgatgctaat aaggttgttg ctggtaaaac tatgaaggaa   120
cattgtcgtt ttgctttatc ttggtggcat acactttgcg caggtggagc tgatcctttt   180
ggtgttcata caatggatag aacttacgga acattacag atccaatgga attggcaaaa    240
gctaaggttg atgctggttt tgaacttatg actaagttgg gaattgaatt tttctgtttt   300
catgatgcag atattgctcc tgaaggagat acatttgaag aatctaagaa aaatcttttt   360
gaaattgttg attacattaa agaaagatg gatcaaactg gtattaaaact tctttgggga   420
acagctaaca acttttcaca tccacgtttt atgcatggtg cttctacttc atgcaatgct   480
gatgtttttg catatgctgc agctaaaatt aagaacgcat ggatgctac tattaaactt    540
ggtggaaagg gttacgtttt ctggggtgga cgtgaaggat acgaaacttt gcttaacaca   600
gatcttggtt tggaattaga taacatggct agacttatga agatggcagt tgaatatgga   660
```

| | | | | | |
|---|---|---|---|---|---|
| cgagctaacg | gttttgatgg | agatttttac | attgaaccta | aaccaaagga | acctactaag | 720
| catcaatacg | attttgatac | tgctacagtt | ttagcatttc | ttcgaaagta | cggtttggaa | 780
| aaggatttta | agatgaacat | tgaagcaaac | catgctactc | ttgcaggaca | tacatttgaa | 840
| catgaattgg | caatggctag | agttaatggt | gcatttggat | ctgttgatgc | taatcaagga | 900
| gatcctaact | taggatggga | tactgatcaa | tttccaacag | atgttcattc | agctactttg | 960
| gcaatgttag | aagttcttaa | agctggtggt | tttactaatg | gtggacttaa | ctttgatgct | 1020
| aaggttcgta | gaggttcttt | tgaatttgat | gatattgctt | acggttacat | tgcaggaatg | 1080
| gatactttg | ctcttggttt | gattaaagca | gctgaaatta | ttgatgatgg | acgaattgct | 1140
| aagtttgttg | atgatcgtta | tgcttcatac | aaaactggta | ttggaaaggc | tattgttgat | 1200
| ggtactacat | ctttggaaga | attagaacaa | tacgttctta | ctcattcaga | acctgttatg | 1260
| caatcaggtc | gtcaagaagt | tttggaaact | attgttaata | acattctttt | tagactcgag | 1320